(12) United States Patent
Menchen et al.

(10) Patent No.: US 10,344,325 B2
(45) Date of Patent: Jul. 9, 2019

(54) THIOLATED NUCLEOTIDE ANALOGUES FOR NUCLEIC ACID SYNTHESIS

(71) Applicant: LIFE TECHNOLOGIES CORPORATION, Carlsbad, CA (US)

(72) Inventors: Steven Menchen, Fremont, CA (US); Theo Nikiforov, Carlsbad, CA (US); Barnett Rosenblum, San Jose, CA (US)

(73) Assignee: Life Technologies Corporation, Carlsbad, CA (US)

( * ) Notice: Subject to any disclaimer, the term of this patent is extended or adjusted under 35 U.S.C. 154(b) by 526 days.

(21) Appl. No.: 14/937,211

(22) Filed: Nov. 10, 2015

(65) Prior Publication Data

US 2016/0130644 A1    May 12, 2016

Related U.S. Application Data

(60) Provisional application No. 62/078,323, filed on Nov. 11, 2014.

(51) Int. Cl.
  *C12Q 1/68* (2018.01)
  *C12Q 1/6869* (2018.01)
  *G01N 27/414* (2006.01)

(52) U.S. Cl.
  CPC ....... *C12Q 1/6869* (2013.01); *G01N 27/4145* (2013.01)

(58) Field of Classification Search
  None
  See application file for complete search history.

(56) References Cited

U.S. PATENT DOCUMENTS

| 2001/0018184 | A1 | 8/2001 | Williams |
| 2009/0026082 | A1 | 1/2009 | Rothberg et al. |
| 2009/0286245 | A1* | 11/2009 | Bjornson ............. C12Q 1/6869 435/6.18 |

(Continued)

FOREIGN PATENT DOCUMENTS

| CN | 103205357.8 | 7/2013 |
| EP | 0866070 | 9/1998 |

(Continued)

OTHER PUBLICATIONS

Brennan, J. Components of Lysis Buffers [online] Apr. 25, 2017 [retrieved on Jan. 31, 2018] retrieved from https://sciencing.com/components-lysis-buffers-8148370.html (Year: 2017).*

(Continued)

*Primary Examiner* — Samuel C Woolwine

(57) ABSTRACT

The present disclosure provide systems, compositions, methods, reagents, kits and products for extending a nucleic acid that includes incorporating a nucleotide residue at a terminus of a nucleic acid using a polymerase enzyme and at least one nucleotide, wherein the at least one nucleotide includes a thiophosphate moiety, and wherein the at least one nucleotide is resistant to hydrolysis by phosphatase. In some embodiments, the nucleotide incorporation can be conducted in the presence of a phosphatase. In some embodiments, the nucleotide incorporation can be conducted in the presence of at least on chelation moiety that is configured to bind an orthophosphate moiety.

19 Claims, 5 Drawing Sheets

Specification includes a Sequence Listing.

(56) References Cited

U.S. PATENT DOCUMENTS

| | | | |
|---|---|---|---|
| 2012/0202276 A1* | 8/2012 | Davidson | C12N 9/1252 435/287.2 |
| 2013/0189699 A1* | 7/2013 | Ou | C12Q 1/6825 435/6.11 |
| 2014/0274732 A1* | 9/2014 | Hanes | C12Q 1/6869 506/2 |

FOREIGN PATENT DOCUMENTS

| WO | WO-2000/036152 | 6/2000 |
|---|---|---|
| WO | WO-2011/106629 | 9/2011 |
| WO | WO-2012/045889 | 4/2012 |

OTHER PUBLICATIONS

Amer, S. Simplified Removal of Chelated Metals. Metal Finishing 102(4) Apr. 2004 (5 pages). (Year: 2004).*

NEB Bst DNA Polymerase, Large Fragment (product information sheet). Sep. 2014. (Year: 2014).*

Sims et al. Fluorogenic DNA sequencing in PDMS microreactors. Nature Methods 8(7):575-580 (2011). (Year: 2011).*

Mathemeier & Morita. Influence of substrate-cofactor ratios on partially purified inorganic pyrophosphatase activity at elevated temperatures. Journal of Bacteriology 88(6): 1661-1666. (Year: 1964).*

Hargrove, Amanda et al., "Artificial Receptors for the Recognition of Phosphorylated Molecules", *Chem. Rev.*, 111, dx.doi.org/10.1021/cr100242s, 2011, 6603-6782.

Lee, Semin et al., "A pentagonal cyanostar macrocycle with cyanostilbene CH donors binds anions and forms dialkylphosphate [3] rotaxanes", *Nature Chemistry*, Jun. 2013, 1-7.

PCT/US2015/059921, International Search Report and Written Opinion dated Feb. 16, 2016, 1-14 pages.

* cited by examiner

SEQUENCE LISTING

<160> NUMBER OF SEQ ID NOS: 84

<210> SEQ ID NO 1
<211> LENGTH: 581
<212> TYPE: PRT
<213> ORGANISM: Bacillus stearothermophilus

<400> SEQUENCE: 1

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu His Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
            165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
```

```
            225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Glu Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr His Tyr Gly Ser Thr
                565                 570                 575

Trp Tyr Asp Ala Lys
            580

<210> SEQ ID NO 2
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Asn Glu Arg Gly Arg
            35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
    195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
    275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
    355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
```

Ser Arg Lys Glu Ala Ala Glu Phe Ile Glu Arg Tyr Phe Gln Ser Phe
            420                 425                 430

Pro Gly Val Lys Arg Tyr Met Glu Asn Ile Val Gln Glu Ala Lys Gln
        435                 440                 445

Lys Gly Tyr Val Thr Thr Leu Leu His Arg Arg Tyr Leu Pro Asp
450                 455                 460

Ile Thr Ser Arg Asn Phe Asn Val Arg Ser Phe Ala Glu Arg Met Ala
465                 470                 475                 480

Met Asn Thr Pro Ile Gln Gly Ser Ala Ala Asp Ile Ile Lys Lys Ala
            485                 490                 495

Met Ile Asp Leu Asn Ala Arg Leu Lys Glu Glu Arg Leu Gln Ala His
            500                 505                 510

Leu Leu Leu Gln Val His Asp Glu Leu Ile Leu Glu Ala Pro Lys Glu
        515                 520                 525

Glu Met Glu Arg Leu Cys Arg Leu Val Pro Glu Val Met Glu Gln Ala
    530                 535                 540

Val Thr Leu Arg Val Pro Leu Lys Val Asp Tyr Arg Tyr Gly Ser Thr
545                 550                 555                 560

Trp Tyr Asp Ala Lys
            565                 570                 575

580

<210> SEQ ID NO 3
<211> LENGTH: 581
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 3

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

```
Met Glu Phe Ala Gly Val Lys Val Asp Thr Lys Arg Leu Glu Gln Met
            195                 200                 205
Gly Lys Glu Leu Ala Glu Gln Leu Gly Thr Val Glu Gln Arg Ile Tyr
210                 215                 220
Glu Leu Ala Gly Gln Glu Phe Asn Ile Asn Ser Pro Lys Gln Leu Gly
225                 230                 235                 240
Val Ile Leu Phe Glu Lys Leu Gln Leu Pro Val Leu Lys Lys Thr Lys
                245                 250                 255
Thr Gly Tyr Ser Thr Ser Ala Asp Val Leu Glu Lys Leu Ala Pro Tyr
                260                 265                 270
His Glu Ile Val Glu Asn Ile Leu His Tyr Arg Gln Leu Gly Lys Leu
                275                 280                 285
Gln Ser Thr Tyr Ile Glu Gly Leu Leu Lys Val Val Arg Pro Asp Thr
290                 295                 300
Lys Lys Val His Thr Ile Phe Asn Gln Ala Leu Thr Gln Thr Gly Arg
305                 310                 315                 320
Leu Ser Ser Thr Glu Pro Asn Leu Gln Asn Ile Pro Ile Arg Leu Glu
                325                 330                 335
Glu Gly Arg Lys Ile Arg Gln Ala Phe Val Pro Ser Glu Ser Asp Trp
                340                 345                 350
Leu Ile Phe Ala Ala Asp Tyr Ser Gln Ile Glu Leu Arg Val Leu Ala
                355                 360                 365
His Ile Ala Glu Asp Asp Asn Leu Met Glu Ala Phe Arg Arg Asp Leu
                370                 375                 380
Asp Ile His Thr Lys Thr Ala Met Asp Ile Phe Gln Val Ser Glu Asp
385                 390                 395                 400
Glu Val Thr Pro Asn Met Arg Arg Gln Ala Lys Ala Val Asn Phe Gly
                405                 410                 415
Ile Val Tyr Gly Ile Ser Asp Tyr Gly Leu Ala Gln Asn Leu Asn Ile
                420                 425                 430
Ser Arg Lys Glu Ala Ala Glu Phe Ile Glu Arg Tyr Phe Gln Ser Phe
                435                 440                 445
Pro Gly Val Lys Arg Tyr Met Glu Asn Ile Val Gln Glu Ala Lys Gln
450                 455                 460
Lys Gly Tyr Val Thr Thr Leu Leu Arg Arg Arg Arg Tyr Leu Pro Asp
465                 470                 475                 480
Ile Thr Ser Arg Asn Phe Asn Val Arg Ser Phe Ala Glu Arg Met Ala
                485                 490                 495
Met Asn Thr Pro Ile Gln Gly Ser Ala Ala Asp Ile Ile Lys Lys Ala
                500                 505                 510
Met Ile Asp Leu Asn Ala Arg Leu Lys Glu Glu Arg Leu Gln Ala Ala
                515                 520                 525
Leu Leu Leu Gln Val His Asp Glu Leu Ile Leu Glu Ala Pro Lys Glu
530                 535                 540
Glu Met Glu Arg Leu Cys Arg Leu Val Pro Glu Val Met Glu Gln Ala
545                 550                 555                 560
Val Thr Leu Arg Val Pro Leu Lys Val Asp Tyr Arg Tyr Gly Ser Thr
                565                 570                 575
Trp Tyr Asp Ala Lys
            580

<210> SEQ ID NO 4
<211> LENGTH: 581
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 4

```
Met Ala Lys Met Ala Phe Thr Leu Ala Asp Arg Val Thr Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu Arg Gly Arg
            35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
                100                 105                 110

Asp Asp Val Ala Ala Ala Lys Met Lys Gln Tyr Glu Ala Val Arg
                115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
                180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

Arg Glu Ile Val Glu Asn Ile Leu Ala Tyr Arg Gln Leu Gly Lys Leu
                275                 280                 285

Gln Ser Thr Tyr Ile Glu Gly Leu Leu Lys Val Val Arg Pro Asp Thr
        290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
    370                 375                 380
```

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
            405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
            435                 440                 445

Pro Gly Val Lys Arg Tyr Met Glu Asn Ile Val Gln Glu Ala Lys Gln
            450                 455                 460

Lys Gly Tyr Val Thr Thr Leu Leu Arg Arg Arg Phe Leu Pro Asp
465                 470                 475                 480

Ile Thr Ser Arg Asn Phe Asn Val Arg Ser Phe Ala Glu Arg Met Ala
            485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
            515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
            565                 570                 575

Trp Tyr Asp Ala Lys
            580

<210> SEQ ID NO 5
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
130                 135                 140

Leu Tyr His Glu Gly Glu Glu Phe Gly Thr Gly Pro Ile Leu Met Ile
145                 150                 155                 160

```
Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575
```

```
Leu Glu Tyr Glu Gly Phe Tyr Val Arg Gly Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys
770                 775

<210> SEQ ID NO 6
<211> LENGTH: 774
<212> TYPE: PRT
<213> ORGANISM: Thermococcus kodakaraensis

<400> SEQUENCE: 6

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
            85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175
```

```
Asp Leu Pro Tyr Val Asp Val Ser Thr Glu Arg Glu Met Ile Lys
            180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
            210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Thr Ala Trp Glu Thr Gly Glu Asn
            290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590
```

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 7
<211> LENGTH: 572
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 7

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Arg Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 8
<211> LENGTH: 572

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Phe Asp
    370                 375                 380
```

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
        450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
            515                 520                 525

Gly Met Thr Asp Thr Ile Lys Lys Lys Val Thr Phe Asp Asn Phe Arg
530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 9
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Ala Ile Glu Ile Ile Ala Arg Ala Leu Asp Ile

```
                165                 170                 175
Gln Phe Lys Gln Gly Leu Asp Arg Met Thr Ala Gly Ser Asp Ser Leu
            180                 185                 190

Lys Gly Phe Lys Asp Ile Leu Ser Thr Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Lys Phe Ser Val Lys Cys Ala
        515                 520                 525

Gly Met Thr Asp Thr Ile Lys Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570
```

<210> SEQ ID NO 10

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 10

Asp Xaa Ser Xaa Xaa Glu
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(7)
<223> OTHER INFORMATION: Any amino acid

<400> SEQUENCE: 11

Lys Xaa Xaa Xaa Xaa Xaa Xaa Tyr Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus

<400> SEQUENCE: 12

Val His Asp Glu
1

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(3)
<223> OTHER INFORMATION: Any amino acid

<400> SEQUENCE: 13

Asp Xaa Xaa Ser Leu Tyr Pro Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus
<220> FEATURE:
```

```
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 14

Lys Xaa Xaa Xaa Asn Ser Xaa Tyr Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus

<400> SEQUENCE: 15

Tyr Gly Asp Thr Asp Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (6)..(6)
<223> OTHER INFORMATION: Phe or Tyr

<400> SEQUENCE: 16

Asp Xaa Xaa Xaa Xaa Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (7)..(7)
<223> OTHER INFORMATION: Ser or Ala

<400> SEQUENCE: 17

Phe Xaa Gly Xaa Xaa Xaa Xaa
1               5

<210> SEQ ID NO 18
<211> LENGTH: 575
<212> TYPE: PRT
```

<213> ORGANISM: Bacillus sp.
<220> FEATURE:
<221> NAME/KEY: misc_feature
<223> OTHER INFORMATION: Bacteriophage Phi29

<400> SEQUENCE: 18

| Met | Lys | His | Met | Pro | Arg | Lys | Met | Tyr | Ser | Cys | Ala | Phe | Glu | Thr | Thr |
|---|---|---|---|---|---|---|---|---|---|---|---|---|---|---|---|
| 1 | | | | 5 | | | | | 10 | | | | | 15 | |

| Thr | Lys | Val | Glu | Asp | Cys | Arg | Val | Trp | Ala | Tyr | Gly | Tyr | Met | Asn | Ile |
|---|---|---|---|---|---|---|---|---|---|---|---|---|---|---|---|
| | | | 20 | | | | | 25 | | | | | 30 | | |

| Glu | Asp | His | Ser | Glu | Tyr | Lys | Ile | Gly | Asn | Ser | Leu | Asp | Glu | Phe | Met |
|---|---|---|---|---|---|---|---|---|---|---|---|---|---|---|---|
| | | | 35 | | | | | 40 | | | | | 45 | | |

| Ala | Trp | Val | Leu | Lys | Val | Gln | Ala | Asp | Leu | Tyr | Phe | His | Asn | Leu | Lys |
|---|---|---|---|---|---|---|---|---|---|---|---|---|---|---|---|
| | 50 | | | | | 55 | | | | | 60 | | | | |

| Phe | Ala | Gly | Ala | Phe | Ile | Ile | Asn | Trp | Leu | Glu | Arg | Asn | Gly | Phe | Lys |
|---|---|---|---|---|---|---|---|---|---|---|---|---|---|---|---|
| 65 | | | | | 70 | | | | | 75 | | | | | 80 |

| Trp | Ser | Ala | Asp | Gly | Leu | Pro | Asn | Thr | Tyr | Asn | Thr | Ile | Ile | Ser | Arg |
|---|---|---|---|---|---|---|---|---|---|---|---|---|---|---|---|
| | | | | 85 | | | | | 90 | | | | | 95 | |

| Met | Gly | Gln | Trp | Tyr | Met | Ile | Asp | Ile | Cys | Leu | Gly | Tyr | Lys | Gly | Lys |
|---|---|---|---|---|---|---|---|---|---|---|---|---|---|---|---|
| | | | 100 | | | | | 105 | | | | | 110 | | |

| Arg | Lys | Ile | His | Thr | Val | Ile | Tyr | Asp | Ser | Leu | Lys | Lys | Leu | Pro | Phe |
|---|---|---|---|---|---|---|---|---|---|---|---|---|---|---|---|
| | | | 115 | | | | | 120 | | | | | 125 | | |

| Pro | Val | Lys | Lys | Ile | Ala | Lys | Asp | Phe | Lys | Leu | Thr | Val | Leu | Lys | Gly |
|---|---|---|---|---|---|---|---|---|---|---|---|---|---|---|---|
| | 130 | | | | | 135 | | | | | 140 | | | | |

| Asp | Ile | Asp | Tyr | His | Lys | Glu | Arg | Pro | Val | Gly | Tyr | Lys | Ile | Thr | Pro |
|---|---|---|---|---|---|---|---|---|---|---|---|---|---|---|---|
| 145 | | | | | 150 | | | | | 155 | | | | | 160 |

| Glu | Glu | Tyr | Ala | Tyr | Ile | Lys | Asn | Asp | Ile | Gln | Ile | Ile | Ala | Glu | Ala |
|---|---|---|---|---|---|---|---|---|---|---|---|---|---|---|---|
| | | | | 165 | | | | | 170 | | | | | 175 | |

| Leu | Leu | Ile | Gln | Phe | Lys | Gln | Gly | Leu | Asp | Arg | Met | Thr | Ala | Gly | Ser |
|---|---|---|---|---|---|---|---|---|---|---|---|---|---|---|---|
| | | | 180 | | | | | 185 | | | | | 190 | | |

| Asp | Ser | Leu | Lys | Gly | Phe | Lys | Asp | Ile | Ile | Thr | Thr | Lys | Lys | Phe | Lys |
|---|---|---|---|---|---|---|---|---|---|---|---|---|---|---|---|
| | | | 195 | | | | | 200 | | | | | 205 | | |

| Lys | Val | Phe | Pro | Thr | Leu | Ser | Leu | Gly | Leu | Asp | Lys | Glu | Val | Arg | Tyr |
|---|---|---|---|---|---|---|---|---|---|---|---|---|---|---|---|
| | 210 | | | | | 215 | | | | | 220 | | | | |

| Ala | Tyr | Arg | Gly | Gly | Phe | Thr | Trp | Leu | Asn | Asp | Arg | Phe | Lys | Glu | Lys |
|---|---|---|---|---|---|---|---|---|---|---|---|---|---|---|---|
| 225 | | | | | 230 | | | | | 235 | | | | | 240 |

| Glu | Ile | Gly | Glu | Gly | Met | Val | Phe | Asp | Val | Asn | Ser | Leu | Tyr | Pro | Ala |
|---|---|---|---|---|---|---|---|---|---|---|---|---|---|---|---|
| | | | | 245 | | | | | 250 | | | | | 255 | |

| Gln | Met | Tyr | Ser | Arg | Leu | Leu | Pro | Tyr | Gly | Glu | Pro | Ile | Val | Phe | Glu |
|---|---|---|---|---|---|---|---|---|---|---|---|---|---|---|---|
| | | | 260 | | | | | 265 | | | | | 270 | | |

| Gly | Lys | Tyr | Val | Trp | Asp | Glu | Asp | Tyr | Pro | Leu | His | Ile | Gln | His | Ile |
|---|---|---|---|---|---|---|---|---|---|---|---|---|---|---|---|
| | | | 275 | | | | | 280 | | | | | 285 | | |

| Arg | Cys | Glu | Phe | Glu | Leu | Lys | Glu | Gly | Tyr | Ile | Pro | Thr | Ile | Gln | Ile |
|---|---|---|---|---|---|---|---|---|---|---|---|---|---|---|---|
| | 290 | | | | | 295 | | | | | 300 | | | | |

| Lys | Arg | Ser | Arg | Phe | Tyr | Lys | Gly | Asn | Glu | Tyr | Leu | Lys | Ser | Ser | Gly |
|---|---|---|---|---|---|---|---|---|---|---|---|---|---|---|---|
| 305 | | | | | 310 | | | | | 315 | | | | | 320 |

| Gly | Glu | Ile | Ala | Asp | Leu | Trp | Leu | Ser | Asn | Val | Asp | Leu | Glu | Leu | Met |
|---|---|---|---|---|---|---|---|---|---|---|---|---|---|---|---|
| | | | | 325 | | | | | 330 | | | | | 335 | |

| Lys | Glu | His | Tyr | Asp | Leu | Tyr | Asn | Val | Glu | Tyr | Ile | Ser | Gly | Leu | Lys |
|---|---|---|---|---|---|---|---|---|---|---|---|---|---|---|---|
| | | | 340 | | | | | 345 | | | | | 350 | | |

| Phe | Lys | Ala | Thr | Thr | Gly | Leu | Phe | Lys | Asp | Phe | Ile | Asp | Lys | Trp | Thr |
|---|---|---|---|---|---|---|---|---|---|---|---|---|---|---|---|
| | | 355 | | | | | 360 | | | | | 365 | | | |

| Tyr | Ile | Lys | Thr | Thr | Ser | Glu | Gly | Ala | Ile | Lys | Gln | Leu | Ala | Lys | Leu |
|---|---|---|---|---|---|---|---|---|---|---|---|---|---|---|---|
| | 370 | | | | | 375 | | | | | 380 | | | | |

```
Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Thr Lys Asp Pro Val Tyr Thr Pro Met Gly Val Phe
        420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
        500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Leu Val Asp Asp Thr Phe Thr Ile Lys
            565                 570                 575

<210> SEQ ID NO 19
<211> LENGTH: 145
<212> TYPE: PRT
<213> ORGANISM: Escherichia coli

<400> SEQUENCE: 19

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
            85                  90                  95

Tyr Thr Thr Glu Val Val Val Asn Val Gly Gly Thr Met Gln Met Leu
        100                 105                 110

Gly Gly Arg Gln Gly Gly Ala Pro Ala Gly Gly Asn Ile Gly Gly
        115                 120                 125

Gly Gln Pro Gln Gly Gly Trp Gly Gln Pro Gln Gln Pro Gln Gly Gly
    130                 135                 140

Asn
145

<210> SEQ ID NO 20
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(2)
<223> OTHER INFORMATION: Any amino acid

<400> SEQUENCE: 20

Tyr Xaa Asp Asp
1

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus
<220> FEATURE:
<221> NAME/KEY: MOD_RES
<222> LOCATION: (2)..(8)
<223> OTHER INFORMATION: Any amino acid

<400> SEQUENCE: 21

Gly Xaa Xaa Xaa Xaa Xaa Xaa Xaa Lys
1               5

<210> SEQ ID NO 22
<211> LENGTH: 581
<212> TYPE: PRT
<213> ORGANISM: Bacillus stearothermophilus

<400> SEQUENCE: 22

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu His Gly Arg
            35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
```

```
            210                 215                 220
Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
                260                 265                 270

His Glu Ile Val Glu Asn Ile Leu His Tyr Arg Gln Leu Gly Lys Leu
                275                 280                 285

Gln Ser Thr Tyr Ile Glu Gly Leu Leu Lys Val Val Arg Pro Asp Thr
        290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
                340                 345                 350

Leu Ile Phe Ala Ala Asp Tyr Ser Gln Ile Glu Leu Arg Val Leu Ala
                355                 360                 365

His Ile Ala Glu Asp Asp Asn Leu Met Glu Ala Phe Arg Arg Asp Leu
                370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
                420                 425                 430

Ser Arg Lys Glu Ala Ala Glu Phe Ile Glu Arg Tyr Phe Glu Ser Phe
                435                 440                 445

Pro Gly Val Lys Arg Tyr Met Glu Asn Ile Val Gln Glu Ala Lys Gln
                450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
                500                 505                 510

Met Ile Asp Leu Asn Ala Arg Leu Lys Glu Glu Arg Leu Gln Ala His
                515                 520                 525

Leu Leu Leu Gln Val His Asp Glu Leu Ile Leu Glu Ala Pro Lys Glu
                530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr His Tyr Gly Ser Thr
                565                 570                 575

Trp Tyr Asp Ala Lys
            580

<210> SEQ ID NO 23
<211> LENGTH: 581
<212> TYPE: PRT
<213> ORGANISM: Bacillus stearothermophilus

<400> SEQUENCE: 23
```

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
        100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
```

```
                420            425            430
Ser Arg Lys Glu Ala Ala Glu Phe Ile Glu Arg Tyr Phe Gln Ser Phe
            435                440                445

Pro Gly Val Lys Arg Tyr Met Glu Asn Ile Val Gln Glu Ala Lys Gln
        450                455                460

Lys Gly Tyr Val Thr Thr Leu Leu His Arg Arg Tyr Leu Pro Asp
465                470                475                480

Ile Thr Ser Arg Asn Phe Asn Val Arg Ser Phe Ala Glu Arg Met Ala
            485                490                495

Met Asn Thr Pro Ile Gln Gly Ser Ala Ala Asp Ile Ile Lys Lys Ala
            500                505                510

Met Ile Asp Leu Asn Ala Arg Leu Lys Glu Glu Arg Leu Gln Ala His
        515                520                525

Leu Leu Leu Gln Val His Asp Glu Leu Ile Leu Glu Ala Pro Lys Glu
        530                535                540

Glu Met Glu Arg Leu Cys Arg Leu Val Pro Glu Val Met Glu Gln Ala
545                550                555                560

Val Thr Leu Arg Val Pro Leu Lys Val Asp Tyr Arg Tyr Gly Ser Thr
            565                570                575

Trp Tyr Asp Ala Lys
            580

<210> SEQ ID NO 24
<211> LENGTH: 581
<212> TYPE: PRT
<213> ORGANISM: Bacillus stearothermophilus

<400> SEQUENCE: 24

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
        130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205
```

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
450                 455                 460

Lys Gly Tyr Val Thr Thr Leu Leu Arg Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
        515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 25
<211> LENGTH: 581
<212> TYPE: PRT
<213> ORGANISM: Bacillus stearothermophilus

<400> SEQUENCE: 25

-continued

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu Arg Gly Arg
                35                  40                  45

Phe Phe Leu Arg Pro Glu Thr Ala Leu Ala Asp Pro Gln Phe Val Ala
50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
                100                 105                 110

Asp Asp Val Ala Ala Ala Lys Met Lys Gln Tyr Glu Ala Val Arg
                115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
                180                 185                 190

Met Glu Phe Ala Gly Val Lys Val Asp Thr Lys Arg Leu Glu Gln Met
                195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
                260                 265                 270

Arg Glu Ile Val Glu Asn Ile Leu Ala Tyr Arg Gln Leu Gly Lys Leu
                275                 280                 285

Gln Ser Thr Tyr Ile Glu Gly Leu Leu Lys Val Val Arg Pro Asp Thr
                290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
                340                 345                 350

Leu Ile Phe Ala Ala Asp Tyr Ser Gln Ile Glu Leu Arg Val Leu Ala
                355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415
```

```
Ile Val Tyr Gly Ile Ser Asp Tyr Gly Leu Ala Gln Asn Leu Asn Ile
                420                 425                 430

Ser Arg Lys Glu Ala Ala Glu Phe Ile Glu Arg Tyr Phe Gln Ser Phe
            435                 440                 445

Pro Gly Val Lys Arg Tyr Met Glu Asn Ile Val Gln Glu Ala Lys Gln
            450                 455                 460

Lys Gly Tyr Val Thr Thr Leu Leu Arg Arg Arg Phe Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
            515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 26
<211> LENGTH: 6
<212> TYPE: PRT
<213> ORGANISM: Artificial Sequence
<220> FEATURE:
<223> OTHER INFORMATION: consensus sequence for motif A family A
      polymerase
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 26

Asp Xaa Ser Xaa Xaa Glu
1               5

<210> SEQ ID NO 27
<211> LENGTH: 9
<212> TYPE: PRT
<213> ORGANISM: Artificial Sequence
<220> FEATURE:
<223> OTHER INFORMATION: consensus sequence for motif B family A
      polymerase
<220> FEATURE:
<221> NAME/KEY: misc_feature
<222> LOCATION: (2)..(7)
<223> OTHER INFORMATION: Xaa can be any naturally occurring amino acid

<400> SEQUENCE: 27

Lys Xaa Xaa Xaa Xaa Xaa Xaa Tyr Gly
1               5

<210> SEQ ID NO 28
<211> LENGTH: 4
<212> TYPE: PRT
<213> ORGANISM: Artificial Sequence
<220> FEATURE:
```

```
<223> OTHER INFORMATION: consensus sequence for motif C family A
      polymerase

<400> SEQUENCE: 28

Val His Asp Glu
1

<210> SEQ ID NO 29
<211> LENGTH: 8
<212> TYPE: PRT
<213> ORGANISM: Artificial Sequence
<220> FEATURE:
<223> OTHER INFORMATION: consensus sequence for motif A family B
      polymerase
<220> FEATURE:
<221> NAME/KEY: misc_feature
<222> LOCATION: (2)..(3)
<223> OTHER INFORMATION: Xaa can be any naturally occurring amino acid

<400> SEQUENCE: 29

Asp Xaa Xaa Ser Leu Tyr Pro Ser
1               5

<210> SEQ ID NO 30
<211> LENGTH: 9
<212> TYPE: PRT
<213> ORGANISM: Artificial Sequence
<220> FEATURE:
<223> OTHER INFORMATION: consensus sequence for motif B family B
      polymerase
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 30

Lys Xaa Xaa Xaa Asn Ser Xaa Tyr Gly
1               5

<210> SEQ ID NO 31
<211> LENGTH: 6
<212> TYPE: PRT
<213> ORGANISM: Artificial Sequence
<220> FEATURE:
<223> OTHER INFORMATION: consensus sequence for motif C family B
      polymerase

<400> SEQUENCE: 31

Tyr Gly Asp Thr Asp Ser
1               5

<210> SEQ ID NO 32
<211> LENGTH: 7
<212> TYPE: PRT
<213> ORGANISM: Artificial Sequence
<220> FEATURE:
<223> OTHER INFORMATION: consensus sequence for motif A
<220> FEATURE:
<221> NAME/KEY: misc_feature
<222> LOCATION: (2)..(5)
<223> OTHER INFORMATION: Xaa can be any naturally occurring amino acid

<400> SEQUENCE: 32

Asp Xaa Xaa Xaa Xaa Phe Tyr
1               5
```

-continued

<210> SEQ ID NO 33
<211> LENGTH: 8
<212> TYPE: PRT
<213> ORGANISM: Artificial Sequence
<220> FEATURE:
<223> OTHER INFORMATION: consensus sequence for motif B
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 33

Phe Xaa Gly Xaa Xaa Xaa Ser Ala
1               5

<210> SEQ ID NO 34
<211> LENGTH: 4
<212> TYPE: PRT
<213> ORGANISM: Artificial Sequence
<220> FEATURE:
<223> OTHER INFORMATION: consensus sequence for motif C
<220> FEATURE:
<221> NAME/KEY: misc_feature
<222> LOCATION: (2)..(2)
<223> OTHER INFORMATION: Xaa can be any naturally occurring amino acid

<400> SEQUENCE: 34

Tyr Xaa Asp Asp
1

<210> SEQ ID NO 35
<211> LENGTH: 9
<212> TYPE: PRT
<213> ORGANISM: Artificial Sequence
<220> FEATURE:
<223> OTHER INFORMATION: consensus sequence for motif D
<220> FEATURE:
<221> NAME/KEY: misc_feature
<222> LOCATION: (2)..(8)
<223> OTHER INFORMATION: Xaa can be any naturally occurring amino acid

<400> SEQUENCE: 35

Gly Xaa Xaa Xaa Xaa Xaa Xaa Xaa Lys
1               5

<210> SEQ ID NO 36
<211> LENGTH: 832
<212> TYPE: PRT
<213> ORGANISM: Thermus aquaticus

<400> SEQUENCE: 36

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu

-continued

```
                85                  90                  95
Ala Leu Ile Lys Glu Leu Val Asp Leu Gly Leu Ala Arg Leu Glu
            100                 105                 110

Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510
```

```
Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 37
<211> LENGTH: 876
<212> TYPE: PRT
<213> ORGANISM: Bacillus stearothermophilus

<400> SEQUENCE: 37

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
```

```
               50                  55                  60
Phe Arg His Glu Ala Phe Gln Glu Tyr Lys Gly Gly Arg Gln Gln Thr
 65                  70                  75                  80

Pro Pro Glu Leu Ser Glu Gln Phe Pro Leu Leu Arg Glu Leu Leu Arg
                     85                  90                  95

Ala Tyr Arg Ile Pro Ala Tyr Glu Leu Glu Asn Tyr Glu Ala Asp Asp
                    100                 105                 110

Ile Ile Gly Thr Leu Ala Ala Arg Ala Glu Gln Glu Gly Phe Glu Val
                    115                 120                 125

Lys Val Ile Ser Gly Asp Arg Asp Leu Thr Gln Leu Ala Ser Pro His
                    130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                    165                 170                 175

Val Asp Leu Lys Gly Leu Met Gly Asp Lys Ser Asp Asn Ile Pro Gly
                    180                 185                 190

Val Pro Gly Ile Gly Glu Lys Thr Ala Val Lys Leu Leu Arg Gln Phe
                    195                 200                 205

Gly Thr Val Glu Asn Val Leu Ala Ser Ile Asp Glu Ile Lys Gly Glu
                    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                    245                 250                 255

Asp Asp Ile Ala Tyr Gln Gly Glu Asp Arg Glu Lys Val Val Ala Leu
                    260                 265                 270

Phe Lys Glu Leu Gly Phe Gln Ser Phe Leu Glu Lys Met Glu Ser Pro
                    275                 280                 285

Ser Ser Glu Glu Glu Lys Pro Leu Ala Lys Met Ala Phe Thr Leu Ala
                    290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                    325                 330                 335

Val Val Asn Glu His Gly Arg Phe Phe Leu Arg Pro Glu Thr Ala Leu
                    340                 345                 350

Ala Asp Pro Gln Phe Val Ala Trp Leu Gly Asp Glu Thr Lys Lys Lys
                    355                 360                 365

Ser Met Phe Asp Ser Lys Arg Ala Ala Val Ala Leu Lys Trp Lys Gly
                    370                 375                 380

Ile Glu Leu Cys Gly Val Ser Phe Asp Leu Leu Ala Ala Tyr Leu
385                 390                 395                 400

Leu Asp Pro Ala Gln Gly Val Asp Asp Val Ala Ala Ala Lys Met
                    405                 410                 415

Lys Gln Tyr Glu Ala Val Arg Pro Asp Glu Ala Val Tyr Gly Lys Gly
                    420                 425                 430

Ala Lys Arg Ala Val Pro Asp Glu Pro Val Leu Ala Glu His Leu Val
                    435                 440                 445

Arg Lys Ala Ala Ala Ile Trp Glu Leu Glu Arg Pro Phe Leu Asp Glu
450                 455                 460

Leu Arg Arg Asn Glu Gln Asp Arg Leu Leu Val Glu Leu Glu Gln Pro
465                 470                 475                 480
```

```
Leu Ser Ser Ile Leu Ala Glu Met Glu Phe Ala Gly Val Lys Val Asp
            485                 490                 495

Thr Lys Arg Leu Glu Gln Met Gly Lys Glu Leu Ala Glu Gln Leu Gly
                500                 505                 510

Thr Val Glu Gln Arg Ile Tyr Glu Leu Ala Gly Gln Glu Phe Asn Ile
                515                 520                 525

Asn Ser Pro Lys Gln Leu Gly Val Ile Leu Phe Glu Lys Leu Gln Leu
            530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
                565                 570                 575

Tyr Arg Gln Leu Gly Lys Leu Gln Ser Thr Tyr Ile Glu Gly Leu Leu
                580                 585                 590

Lys Val Val Arg Pro Asp Thr Lys Val His Thr Ile Phe Asn Gln
                595                 600                 605

Ala Leu Thr Gln Thr Gly Arg Leu Ser Ser Thr Glu Pro Asn Leu Gln
            610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
                645                 650                 655

Ile Glu Leu Arg Val Leu Ala His Ile Ala Glu Asp Asp Asn Leu Met
                660                 665                 670

Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
            690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
                740                 745                 750

Ile Val Gln Glu Ala Lys Gln Lys Gly Tyr Val Thr Thr Leu Leu His
                755                 760                 765

Arg Arg Arg Tyr Leu Pro Asp Ile Thr Ser Arg Asn Phe Asn Val Arg
            770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
                805                 810                 815

Glu Glu Arg Leu Gln Ala His Leu Leu Leu Gln Val His Asp Glu Leu
                820                 825                 830

Ile Leu Glu Ala Pro Lys Glu Glu Met Glu Arg Leu Cys Arg Leu Val
            835                 840                 845

Pro Glu Val Met Glu Gln Ala Val Thr Leu Arg Val Pro Leu Lys Val
            850                 855                 860

Asp Tyr His Tyr Gly Ser Thr Trp Tyr Asp Ala Lys
865                 870                 875

<210> SEQ ID NO 38
<211> LENGTH: 1746
```

```
<212> TYPE: DNA
<213> ORGANISM: Bacillus stearothermophilus

<400> SEQUENCE: 38
atggcaaaaa tggcatttac cctggcagat cgtgttaccg aagaaatgct ggcagataaa      60
gcagcactgg ttgttgaagt tgtggaagaa aactatcatg atgcaccgat tgttggtatt     120
gccgttgtta tgaacgcgg tcgtttttt ctgcgtccgg aaaccgcact ggcagatccg       180
cagtttgttg catggctggg tgatgaaacc aaaaagaaaa gcatgttcga cagcaaacgt     240
gcagcagttg cactgaaatg gaaaggtatt gaactgtgcg gtgtgtcatt tgatctgctg     300
ctggcagcat atctgctgga tccggcacag ggtgttgatg atgttgcagc agcagcaaaa     360
atgaaacagt atgaagcagt tcgtccggat gaagcagttt atggtaaagg tgcaaaacgt     420
gcagttccgg atgaaccggt tctggcagaa catctggttc gtaaagcagc agcaatttgg     480
gaactggaac gtccgtttct ggatgaactg cgtcgtaatg aacaggatcg tctgctggtt     540
gaactggaac agccgctgag cagcattctg gcagaaatgg aatttgccgg tgttaaagtt     600
gataccaaac gtctggaaca aatgggtaaa gaactggccg aacaactggg caccgttgaa     660
cagcgtattt atgaactggc aggccaagaa tttaacatta tagcccgaa acagctgggc      720
gttatcctgt ttgaaaaact gcagctgccg gttctgaaaa aaccaaaac cggttatagc      780
accagcgcag atgttctgga aaactggca ccgtatcatg aaattgtgga aaacattctg      840
cactatcgtc agctgggtaa actgcagagc acctatattg aaggtctgct gaaagttgtg     900
cgtccggata ccaaaaagt gcataccatt tttaaccagg cactgaccca gaccggtcgt      960
ctgagcagca ccgaaccgaa tctgcagaat attccgattc gtctggaaga aggtcgtaaa    1020
attcgtcagg catttgttcc gagcgaaagc gattggctga ttttgcagc agattatagc     1080
cagattgaac tgcgtgttct ggcacatatt gccgaagatg ataatctgat ggaagcattt    1140
cgtcgcgatc tggatattca taccaaaaac gccatggata tttttcaggt tagcgaagat    1200
gaagtgaccc cgaatatgcg tcgtcaggca aaagcagtta attttggtat tgtgtatggc    1260
atcagcgatt atggtctggc acagaatctg aatattagcc gtaaagaagc agccgaattt    1320
atcgaacgtt actttcagag ctttccgggt gttaaacgct atatggaaaa cattgtccaa    1380
gaagccaaac agaaaggtta tgttaccacc ctgctgcatc gtcgtcgtta tctgccgcgt    1440
attaccagcc gtaactttaa tgttcgtagc tttcagaaac gcatggcaat gaataccccg    1500
attcagggta gcgcagcaga tattatcaaa aaagccatga tcgatctgaa cgcacgtctg    1560
aaagaagaac gtctgcaggc acatttactg ctgcaggttc atgatgaact gattctggaa    1620
gcaccgaaag aagaaatgga acgtctttgt cgtctggttc cggaagttat ggaacaggca    1680
gttaccctgc gtgttccgct gaaagttgat tatcgttatg gtagcacctg gtatgatgcc    1740
aaataa                                                               1746

<210> SEQ ID NO 39
<211> LENGTH: 606
<212> TYPE: PRT
<213> ORGANISM: Escherichia coli

<400> SEQUENCE: 39

Met Val Ile Ser Tyr Asp Asn Tyr Val Thr Ile Leu Asp Glu Glu Thr
1               5                   10                  15

Leu Lys Ala Trp Ile Ala Lys Leu Glu Lys Ala Pro Val Phe Ala Phe
            20                  25                  30
```

```
Asp Thr Glu Thr Asp Ser Leu Asp Asn Ile Ser Ala Asn Leu Val Gly
            35                  40                  45

Leu Ser Phe Ala Ile Glu Pro Gly Val Ala Ala Tyr Ile Pro Val Ala
 50                      55                  60

His Asp Tyr Leu Asp Ala Pro Asp Gln Ile Ser Arg Glu Arg Ala Leu
 65                  70                  75                  80

Glu Leu Leu Lys Pro Leu Leu Glu Asp Glu Lys Ala Leu Lys Val Gly
                 85                  90                  95

Gln Asn Leu Lys Tyr Asp Arg Gly Ile Leu Ala Asn Tyr Gly Ile Glu
            100                 105                 110

Leu Arg Gly Ile Ala Phe Asp Thr Met Leu Glu Ser Tyr Ile Leu Asn
        115                 120                 125

Ser Val Ala Gly Arg His Asp Met Asp Ser Leu Ala Glu Arg Trp Leu
    130                 135                 140

Lys His Lys Thr Ile Thr Phe Glu Glu Ile Ala Gly Lys Gly Lys Asn
145                 150                 155                 160

Gln Leu Thr Phe Asn Gln Ile Ala Leu Glu Ala Gly Arg Tyr Ala
                165                 170                 175

Ala Glu Asp Ala Asp Val Thr Leu Gln Leu His Leu Lys Met Trp Pro
            180                 185                 190

Asp Leu Gln Lys His Lys Gly Pro Leu Asn Val Phe Glu Asn Ile Glu
        195                 200                 205

Met Pro Leu Val Pro Val Leu Ser Arg Ile Glu Arg Asn Gly Val Lys
    210                 215                 220

Ile Asp Pro Lys Val Leu His Asn His Ser Glu Glu Leu Thr Leu Arg
225                 230                 235                 240

Leu Ala Glu Leu Glu Lys Lys Ala His Glu Ile Ala Gly Glu Glu Phe
                245                 250                 255

Asn Leu Ser Ser Thr Lys Gln Leu Gln Thr Ile Leu Phe Glu Lys Gln
            260                 265                 270

Gly Ile Lys Pro Leu Lys Lys Thr Pro Gly Gly Ala Pro Ser Thr Ser
        275                 280                 285

Glu Glu Val Leu Glu Glu Leu Ala Leu Asp Tyr Pro Leu Pro Lys Val
    290                 295                 300

Ile Leu Glu Tyr Arg Gly Leu Ala Lys Leu Lys Ser Thr Tyr Thr Asp
305                 310                 315                 320

Lys Leu Pro Leu Met Ile Asn Pro Lys Thr Gly Arg Val His Thr Ser
                325                 330                 335

Tyr His Gln Ala Val Thr Ala Thr Gly Arg Leu Ser Ser Thr Asp Pro
            340                 345                 350

Asn Leu Gln Asn Ile Pro Val Arg Asn Glu Glu Gly Arg Arg Ile Arg
        355                 360                 365

Gln Ala Phe Ile Ala Pro Glu Asp Tyr Val Ile Val Ser Ala Asp Tyr
    370                 375                 380

Ser Gln Ile Glu Leu Arg Ile Met Ala His Leu Ser Arg Asp Lys Gly
385                 390                 395                 400

Leu Leu Thr Ala Phe Ala Glu Gly Lys Asp Ile His Arg Ala Thr Ala
                405                 410                 415

Ala Glu Val Phe Gly Leu Pro Leu Glu Thr Val Thr Ser Glu Gln Arg
            420                 425                 430

Arg Ser Ala Lys Ala Ile Asn Phe Gly Leu Ile Tyr Gly Met Ser Ala
        435                 440                 445

Phe Gly Leu Ala Arg Gln Leu Asn Ile Pro Arg Lys Glu Ala Gln Lys
```

```
            450                 455                 460

Tyr Met Asp Leu Tyr Phe Glu Arg Tyr Pro Gly Val Leu Glu Tyr Met
465                 470                 475                 480

Glu Arg Thr Arg Ala Gln Ala Lys Glu Gln Gly Tyr Val Glu Thr Leu
                485                 490                 495

Asp Gly Arg Arg Leu Tyr Leu Pro Asp Ile Lys Ser Ser Asn Gly Ala
                500                 505                 510

Arg Arg Ala Ala Ala Glu Arg Ala Ala Ile Asn Ala Pro Met Gln Gly
                515                 520                 525

Thr Ala Ala Asp Ile Ile Lys Arg Ala Met Ile Ala Val Asp Ala Trp
                530                 535                 540

Leu Gln Ala Glu Gln Pro Arg Val Arg Met Ile Met Gln Val His Asp
545                 550                 555                 560

Glu Leu Val Phe Glu Val His Lys Asp Val Asp Ala Val Ala Lys
                565                 570                 575

Gln Ile His Gln Leu Met Glu Asn Cys Thr Arg Leu Asp Val Pro Leu
                580                 585                 590

Leu Val Glu Val Gly Ser Gly Glu Asn Trp Asp Gln Ala His
                595                 600                 605

<210> SEQ ID NO 40
<211> LENGTH: 581
<212> TYPE: PRT
<213> ORGANISM: Bacillus stearothermophilus

<400> SEQUENCE: 40

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Asn Glu Arg Gly Arg
                35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
        100                 105                 110

Asp Asp Val Ala Ala Ala Lys Met Lys Gln Tyr Glu Ala Val Arg
                115                 120                 125

Pro Asp Glu Ala Val Tyr Gly Lys Gly Ala Lys Arg Ala Val Pro Asp
                130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
                180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Lys Gln Arg Ile Tyr
        210                 215                 220
```

Glu Leu Ala Gly Gln Glu Phe Asn Ile Arg Ser Pro Lys Gln Leu Gly
225                 230                 235                 240

Val Ile Leu Phe Glu Lys Leu Gln Leu Pro Val Leu Lys Lys Thr Lys
            245                 250                 255

Thr Gly Tyr Ser Thr Ser Ala Asp Val Leu Glu Lys Leu Ala Pro Tyr
        260                 265                 270

His Glu Ile Val Glu Asn Ile Leu His Tyr Arg Gln Leu Gly Lys Leu
    275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
            325                 330                 335

Glu Gly Arg Lys Ile Arg Gln Ala Phe Val Pro Ser Glu Ser Asp Trp
        340                 345                 350

Leu Ile Phe Ala Ala Asp Tyr Ser Gln Ile Glu Leu Arg Val Leu Ala
    355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
            405                 410                 415

Ile Val Tyr Gly Ile Ser Lys Tyr Gly Leu Ala Gln Asn Leu Asn Ile
        420                 425                 430

Ser Arg Lys Glu Ala Ala Glu Phe Ile Glu Arg Tyr Phe Gln Ser Phe
    435                 440                 445

Pro Gly Val Lys Arg Tyr Met Glu Asn Ile Val Gln Glu Ala Lys Gln
450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
            485                 490                 495

Met Asn Thr Pro Ile Gln Gly Ser Ala Ala Asp Ile Ile Lys Lys Ala
        500                 505                 510

Met Ile Asp Leu Asn Ala Arg Leu Lys Glu Glu Arg Leu Gln Ala His
    515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
            565                 570                 575

Trp Tyr Asp Ala Lys
        580

<210> SEQ ID NO 41
<211> LENGTH: 581
<212> TYPE: PRT
<213> ORGANISM: Bacillus stearothermophilus

<400> SEQUENCE: 41

Met Ala Lys Met Ala Phe Thr Leu Ala Asp Arg Val Thr Glu Glu Met
1               5                   10                  15

```
Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
            35                  40                  45

Phe Phe Leu Arg Pro Glu Thr Ala Leu Ala Asp Pro Gln Phe Val Ala
 50                  55                  60

Trp Leu Gly Asp Glu Thr Lys Lys Ser Met Phe Asp Ser Lys Arg
 65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
            130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Lys Gln Arg Ile Tyr
210                 215                 220

Glu Leu Ala Gly Gln Glu Phe Asn Ile Arg Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
            275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
            370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Lys Tyr Gly Leu Ala Gln Asn Leu Asn Ile
            420                 425                 430
```

```
Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu Arg Arg Arg Tyr Leu Pro Asp
465             470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
            515                 520                 525

Leu Leu Leu Gln Val His Asp Glu Leu Ile Leu Glu Ala Pro Lys Glu
        530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
        580
```

```
<210> SEQ ID NO 42
<211> LENGTH: 36
<212> TYPE: DNA
<213> ORGANISM: Artificial Sequence
<220> FEATURE:
<223> OTHER INFORMATION: DNA oligonucleotide
<220> FEATURE:
<221> NAME/KEY: misc_feature
<222> LOCATION: (34)..(34)
<223> OTHER INFORMATION: N = fluorescein-dT

<400> SEQUENCE: 42
tttttttgca ggtgacaggt ttttcctgtc accngc                         36

<210> SEQ ID NO 43
<211> LENGTH: 44
<212> TYPE: DNA
<213> ORGANISM: Artificial Sequence
<220> FEATURE:
<223> OTHER INFORMATION: DNA oligonucleotide

<400> SEQUENCE: 43
tttttttccc tttcctttcg ggtgacaggt ttttcctgtc accc                 44

<210> SEQ ID NO 44
<211> LENGTH: 1743
<212> TYPE: DNA
<213> ORGANISM: Bacillus stearothermophilus

<400> SEQUENCE: 44
atggctaaaa tggcttttac tcttgctgat cgtgttactg aagaaatgct tgctgataaa   60
gctgctcttg ttgttgaagt tgttgaagaa aattatcatg atgctcctat tgttggtatt  120
gctgttgtta atgaacgtgg tcgttttttt cttcgtcctg aaactgctct tgctgatcct  180
caatttgttg cttggcttgg tgatgaaact aaaaaaaaat ctatgtttga ttctaaacgt  240
gctgctgttg ctcttaaatg gaaaggtatt gaactttgtg gtgtttcttt tgatcttctt  300
cttgctgctt atcttcttga tcctgctcaa ggtgttgatg atgttgctgc tgctgctaaa  360
atgaaacaat atgaagctgt tcgtcctgat gaagctgttt atggtaaagg tgctaaacgt  420
```

```
gctgttcctg atgaacctgt tcttgctgaa catcttgttc gtaaagctgc tgctatttgg    480
gaacttgaac gtccttttct tgatgaactt cgtcgtaatg aacaagatcg tcttcttgtt    540
gaacttgaac aacctctttc ttctattctt gctgaaatgg aatttgctgg tgttaaagtt    600
gatactaaac gtcttgaaca atgggtaaa gaacttgctg aacaacttgg tactgttaaa    660
caacgtattt atgaacttgc tggtcaagaa tttaatattc gttctcctaa acaacttggt    720
gttattcttt tgaaaaaact tcaacttcct gttcttaaaa aaactaaaac tggttattct    780
acttctgctg atgttcttga aaaacttgct ccttatcatg aaattgttga aatattctt    840 cattatcgtc aacttggtaa acttcaatct acttatattg aaggtcttct taaagttgtt    900
cgtcctgata ctaaaaaagt tcatactatt tttaatcaag ctcttactca aactggtcgt    960 cttcttcta ctgaacctaa tcttcaaaat attcctattc gtcttgaaga aggtcgtaaa   1020
attcgtcaag ctttttgttcc ttctgaatct gattggctta tttttgctgc tgattattct   1080
caaattgaac ttcgtgttct tgctcatatt gctgaagatg ataatcttat ggaagctttt   1140
cgtcgtgatc ttgatattca tactaaaact gctatggata tttttcaagt ttctgaagat   1200
gaagttactc ctaatatgcg tcgtcaagct aaagctgtta attttggtat tgtttatggt   1260
atttctaaat atggtcttgc tcaaaatctt aatatttctc gtaaagaagc tgctgaattt   1320
attgaacgtt atttttcaatc ttttcctggt gttaaacgtt atatggaaaa tattgttcaa   1380
gaagctaaac aaaaaggtta tgttactact cttcttcatc gtcgtcgtta tcttcctgat   1440
attacttctc gtaattttaa tgttcgttct tttgctgaac gtatggctat gaatactcct   1500
attcaaggtt ctgctgctga tattattaaa aaagctatga ttgatcttaa tgctcgtctt   1560
aaagaagaac gtcttcaagc tcatcttctt cttcaagttc atgatgaact tattcttgaa   1620
gctcctaaag aagaaatgga acgtctttgt cgtcttgttc ctgaagttat ggaacaagct   1680
gttactcttc gtgttcctct taaagttgat tatcgttatg gttctacttg gtatgatgct   1740
aaa                                                                  1743
```

<210> SEQ ID NO 45
<211> LENGTH: 832
<212> TYPE: PRT
<213> ORGANISM: Thermus aquaticus

<400> SEQUENCE: 45

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125
```

```
Ala Glu Lys Glu Gly Tyr Glu Val Arg Ile Leu Thr Ala Asp Lys Asp
            130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
            210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
            275                 280                 285
Glu Ser Pro Lys Ala Leu Glu Glu Ala Pro Trp Pro Pro Pro Glu Gly
            290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
```

```
                545                 550                 555                 560
His Thr Arg Phe Asn Gln Thr Ala Thr Ala Thr Gly Arg Leu Ser Ser
                    565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                    645                 650                 655

Leu Met Arg Arg Ala Ala Lys Thr Ile Asn Phe Gly Val Leu Tyr Gly
                    660                 665                 670

Met Ser Ala His Arg Leu Ser Gln Glu Leu Ala Ile Pro Tyr Glu Glu
                    675                 680                 685

Ala Gln Ala Phe Ile Glu Arg Tyr Phe Gln Ser Phe Pro Lys Val Arg
                690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Arg Leu Glu Ala Arg
                    725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
                    755                 760                 765

Phe Pro Arg Leu Glu Glu Met Gly Ala Arg Met Leu Leu Gln Val His
                    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                    805                 810                 815

Leu Glu Val Glu Val Gly Ile Gly Glu Asp Trp Leu Ser Ala Lys Glu
                    820                 825                 830

<210> SEQ ID NO 46
<211> LENGTH: 581
<212> TYPE: PRT
<213> ORGANISM: Artificial Sequence
<220> FEATURE:
<223> OTHER INFORMATION: Synthetic: large fragment of Bst DNA polymerase

<400> SEQUENCE: 46

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu His Gly Arg
            35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
```

-continued

```
                85                  90                  95
Phe Asp Leu Leu Leu Ala Ala Tyr Leu Leu Asp Pro Ala Gln Gly Val
            100                 105                 110
Asp Asp Val Ala Ala Ala Lys Met Lys Gln Tyr Glu Ala Val Arg
            115                 120                 125
Pro Asp Glu Ala Val Tyr Gly Lys Gly Ala Lys Arg Ala Val Pro Asp
            130                 135                 140
Glu Pro Val Leu Ala Glu His Leu Val Arg Lys Ala Ala Ala Ile Trp
145                 150                 155                 160
Glu Leu Glu Arg Pro Phe Leu Asp Glu Leu Arg Arg Asn Glu Gln Asp
                165                 170                 175
Arg Leu Leu Val Glu Leu Glu Gln Pro Leu Ser Ser Ile Leu Ala Glu
                180                 185                 190
Met Glu Phe Ala Gly Val Lys Val Asp Thr Lys Arg Leu Glu Gln Met
                195                 200                 205
Gly Lys Glu Leu Ala Glu Gln Leu Gly Thr Val Glu Gln Arg Ile Tyr
            210                 215                 220
Glu Leu Ala Gly Gln Glu Phe Asn Ile Asn Ser Pro Lys Gln Leu Gly
225                 230                 235                 240
Val Ile Leu Phe Glu Lys Leu Gln Leu Pro Val Leu Lys Lys Thr Lys
                245                 250                 255
Thr Gly Tyr Ser Thr Ser Ala Asp Val Leu Glu Lys Leu Ala Pro Tyr
            260                 265                 270
His Glu Ile Val Glu Asn Ile Leu His Tyr Arg Gln Leu Gly Lys Leu
            275                 280                 285
Gln Ser Thr Tyr Ile Glu Gly Leu Leu Lys Val Val Arg Pro Asp Thr
            290                 295                 300
Lys Lys Val His Thr Ile Phe Asn Gln Ala Leu Thr Gln Thr Gly Arg
305                 310                 315                 320
Leu Ser Ser Thr Glu Pro Asn Leu Gln Asn Ile Pro Ile Arg Leu Glu
                325                 330                 335
Glu Gly Arg Lys Ile Arg Gln Ala Phe Val Pro Ser Glu Ser Asp Trp
            340                 345                 350
Leu Ile Phe Ala Ala Asp Tyr Ser Gln Ile Glu Leu Arg Val Leu Ala
            355                 360                 365
His Ile Ala Glu Asp Asp Asn Leu Met Glu Ala Phe Arg Arg Asp Leu
            370                 375                 380
Asp Ile His Thr Lys Thr Ala Met Asp Ile Phe Gln Val Ser Glu Asp
385                 390                 395                 400
Glu Val Thr Pro Asn Met Arg Arg Gln Ala Lys Ala Val Asn Phe Gly
                405                 410                 415
Ile Val Tyr Gly Ile Ser Asp Tyr Gly Leu Ala Gln Asn Leu Asn Ile
            420                 425                 430
Ser Arg Lys Glu Ala Ala Glu Phe Ile Glu Arg Tyr Phe Glu Ser Phe
            435                 440                 445
Pro Gly Val Lys Arg Tyr Met Glu Asn Ile Val Gln Glu Ala Lys Gln
            450                 455                 460
Lys Gly Tyr Val Thr Thr Leu Leu His Arg Arg Arg Tyr Leu Pro Asp
465                 470                 475                 480
Ile Thr Ser Arg Asn Phe Asn Val Arg Ser Phe Ala Glu Arg Met Ala
                485                 490                 495
Met Asn Thr Pro Ile Gln Gly Ser Ala Ala Asp Ile Ile Lys Lys Ala
            500                 505                 510
```

```
Met Ile Asp Leu Asn Ala Arg Leu Lys Glu Arg Leu Gln Ala His
        515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr His Tyr Gly Ser Thr
                565                 570                 575

Trp Tyr Asp Ala Lys
            580

<210> SEQ ID NO 47
<211> LENGTH: 581
<212> TYPE: PRT
<213> ORGANISM: Artificial Sequence
<220> FEATURE:
<223> OTHER INFORMATION: Synthetic: large fragment Bst DNA polymerase

<400> SEQUENCE: 47

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285
```

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 48
<211> LENGTH: 581
<212> TYPE: PRT
<213> ORGANISM: Artificial Sequence
<220> FEATURE:
<223> OTHER INFORMATION: Synthetic

<400> SEQUENCE: 48

Met Ala Lys Met Ala Phe Thr Leu Ala Asp Arg Val Thr Glu Glu Met
1               5                   10                  15

Leu Ala Asp Lys Ala Ala Leu Val Val Glu Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

```
Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
            85                  90                  95

Phe Asp Leu Leu Leu Ala Ala Tyr Leu Leu Asp Pro Ala Gln Gly Val
                100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
            130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
                180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
            275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
            370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
            435                 440                 445

Pro Gly Val Lys Arg Tyr Met Glu Asn Ile Val Gln Glu Ala Lys Gln
            450                 455                 460

Lys Gly Tyr Val Thr Thr Leu Leu Arg Arg Arg Arg Tyr Leu Pro Asp
465                 470                 475                 480
```

```
Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 49
<211> LENGTH: 581
<212> TYPE: PRT
<213> ORGANISM: Artificial Sequence
<220> FEATURE:
<223> OTHER INFORMATION: Synthetic

<400> SEQUENCE: 49

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255
```

Thr Gly Tyr Ser Thr Ser Ala Asp Val Leu Glu Lys Leu Ala Pro Tyr
                260                 265                 270

Arg Glu Ile Val Glu Asn Ile Leu Ala Tyr Arg Gln Leu Gly Lys Leu
            275                 280                 285

Gln Ser Thr Tyr Ile Glu Gly Leu Leu Lys Val Val Arg Pro Asp Thr
        290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
450                 455                 460

Lys Gly Tyr Val Thr Thr Leu Leu Arg Arg Arg Phe Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
        515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 50
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

```
<400> SEQUENCE: 50

Asp Xaa Ser Xaa Xaa Glu
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(7)
<223> OTHER INFORMATION: Xaa can be any naturally occurring amino acid

<400> SEQUENCE: 51

Lys Xaa Xaa Xaa Xaa Xaa Xaa Tyr Gly
1               5

<210> SEQ ID NO 52
<211> LENGTH: 4
<212> TYPE: PRT
<213> ORGANISM: Artificial Sequence
<220> FEATURE:
<223> OTHER INFORMATION: Synthetic

<400> SEQUENCE: 52

Val His Asp Glu
1

<210> SEQ ID NO 53
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 53

Asp Xaa Xaa Ser Leu Tyr Pro Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 54

Lys Xaa Xaa Xaa Asn Ser Xaa Tyr Gly
1               5

<210> SEQ ID NO 55
<211> LENGTH: 6
<212> TYPE: PRT
<213> ORGANISM: Artificial Sequence
<220> FEATURE:
```

<223> OTHER INFORMATION: Synthetic

<400> SEQUENCE: 55

Tyr Gly Asp Thr Asp Ser
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is Phe or Tyr

<400> SEQUENCE: 56

Asp Xaa Xaa Xaa Xaa Xaa
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is Ser or Ala

<400> SEQUENCE: 57

Phe Xaa Gly Xaa Xaa Xaa Xaa
1               5

<210> SEQ ID NO 58
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 58

Tyr Xaa Asp Asp
1

<210> SEQ ID NO 59
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(8)
<223> OTHER INFORMATION: Xaa can be any naturally occurring amino acid

<400> SEQUENCE: 59

Gly Xaa Xaa Xaa Xaa Xaa Xaa Lys
1               5

<210> SEQ ID NO 60
<211> LENGTH: 832
<212> TYPE: PRT
<213> ORGANISM: Artificial Sequence
<220> FEATURE:
<223> OTHER INFORMATION: Synthetic

<400> SEQUENCE: 60

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro

-continued

```
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
                450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
                675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
```

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 61
<211> LENGTH: 876
<212> TYPE: PRT
<213> ORGANISM: Artificial Sequence
<220> FEATURE:
<223> OTHER INFORMATION: Synthetic

<400> SEQUENCE: 61

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
            35                  40                  45

Glu Glu Pro Thr His Met Leu Val Ala Phe Asp Ala Gly Lys Thr Thr
        50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
                100                 105                 110

Ile Ile Gly Thr Leu Ala Ala Arg Ala Glu Gln Glu Gly Phe Glu Val
            115                 120                 125

Lys Val Ile Ser Gly Asp Arg Asp Leu Thr Gln Leu Ala Ser Pro His
    130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
                180                 185                 190

Val Pro Gly Ile Gly Glu Lys Thr Ala Val Lys Leu Leu Arg Gln Phe
            195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
                260                 265                 270

Phe Lys Glu Leu Gly Phe Gln Ser Phe Leu Glu Lys Met Glu Ser Pro
            275                 280                 285

```
Ser Ser Glu Glu Lys Pro Leu Ala Lys Met Ala Phe Thr Leu Ala
290             295             300

Asp Arg Val Thr Glu Met Leu Ala Asp Lys Ala Ala Leu Val Val
305             310             315             320

Glu Val Val Glu Glu Asn Tyr His Asp Ala Pro Ile Val Gly Ile Ala
                325             330             335

Val Val Asn Glu His Gly Arg Phe Phe Leu Arg Pro Glu Thr Ala Leu
        340             345             350

Ala Asp Pro Gln Phe Val Ala Trp Leu Gly Asp Glu Thr Lys Lys Lys
        355             360             365

Ser Met Phe Asp Ser Lys Arg Ala Ala Val Ala Leu Lys Trp Lys Gly
        370             375             380

Ile Glu Leu Cys Gly Val Ser Phe Asp Leu Leu Ala Ala Tyr Leu
385             390             395             400

Leu Asp Pro Ala Gln Gly Val Asp Val Ala Ala Ala Lys Met
                405             410             415

Lys Gln Tyr Glu Ala Val Arg Pro Asp Glu Ala Val Tyr Gly Lys Gly
            420             425             430

Ala Lys Arg Ala Val Pro Asp Glu Pro Val Leu Ala Glu His Leu Val
        435             440             445

Arg Lys Ala Ala Ala Ile Trp Glu Leu Glu Arg Pro Phe Leu Asp Glu
450             455             460

Leu Arg Arg Asn Glu Gln Asp Arg Leu Leu Val Glu Leu Glu Gln Pro
465             470             475             480

Leu Ser Ser Ile Leu Ala Glu Met Glu Phe Ala Gly Val Lys Val Asp
                485             490             495

Thr Lys Arg Leu Glu Gln Met Gly Lys Glu Leu Ala Glu Gln Leu Gly
            500             505             510

Thr Val Glu Gln Arg Ile Tyr Glu Leu Ala Gly Gln Glu Phe Asn Ile
        515             520             525

Asn Ser Pro Lys Gln Leu Gly Val Ile Leu Phe Glu Lys Leu Gln Leu
530             535             540

Pro Val Leu Lys Lys Thr Lys Thr Gly Tyr Ser Thr Ser Ala Asp Val
545             550             555             560

Leu Glu Lys Leu Ala Pro Tyr His Glu Ile Val Glu Asn Ile Leu His
                565             570             575

Tyr Arg Gln Leu Gly Lys Leu Gln Ser Thr Tyr Ile Glu Gly Leu Leu
            580             585             590

Lys Val Val Arg Pro Asp Thr Lys Lys Val His Thr Ile Phe Asn Gln
        595             600             605

Ala Leu Thr Gln Thr Gly Arg Leu Ser Ser Thr Glu Pro Asn Leu Gln
610             615             620

Asn Ile Pro Ile Arg Leu Glu Glu Gly Arg Lys Ile Arg Gln Ala Phe
625             630             635             640

Val Pro Ser Glu Ser Asp Trp Leu Ile Phe Ala Ala Asp Tyr Ser Gln
                645             650             655

Ile Glu Leu Arg Val Leu Ala His Ile Ala Glu Asp Asp Asn Leu Met
            660             665             670

Glu Ala Phe Arg Arg Asp Leu Asp Ile His Thr Lys Thr Ala Met Asp
        675             680             685

Ile Phe Gln Val Ser Glu Asp Glu Val Thr Pro Asn Met Arg Arg Gln
690             695             700
```

```
Ala Lys Ala Val Asn Phe Gly Ile Val Tyr Gly Ile Ser Asp Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Asn Val Arg
770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
                805                 810                 815

Glu Glu Arg Leu Gln Ala His Leu Leu Leu Gln Val His Asp Glu Leu
            820                 825                 830

Ile Leu Glu Ala Pro Lys Glu Glu Met Glu Arg Leu Cys Arg Leu Val
        835                 840                 845

Pro Glu Val Met Glu Gln Ala Val Thr Leu Arg Val Pro Leu Lys Val
850                 855                 860

Asp Tyr His Tyr Gly Ser Thr Trp Tyr Asp Ala Lys
865                 870                 875

<210> SEQ ID NO 62
<211> LENGTH: 1746
<212> TYPE: DNA
<213> ORGANISM: Artificial Sequence
<220> FEATURE:
<223> OTHER INFORMATION: Synthetic

<400> SEQUENCE: 62
atggcaaaaa tggcatttac cctggcagat cgtgttaccg aagaaatgct ggcagataaa      60
gcagcactgg ttgttgaagt tgtggaagaa aactatcatg atgcaccgat tgttggtatt     120
gccgttgtta atgaacgcgg tcgttttttt ctgcgtccgg aaaccgcact ggcagatccg     180
cagtttgttg catggctggg tgatgaaacc aaaagaaaa gcatgttcga cagcaaacgt     240
gcagcagttg cactgaaatg gaaaggtatt gaactgtgcg gtgtgtcatt tgatctgctg     300
ctggcagcat atctgctgga tccggcacag ggtgttgatg atgttgcagc agcagcaaaa     360
atgaaacagt atgaagcagt tcgtccggat gaagcagttt atggtaaagg tgcaaaacgt     420
gcagttccgg atgaaccggt tctggcagaa catctggttc gtaaagcagc agcaatttgg     480
gaactggaac gtccgtttct ggatgaactg cgtcgtaatg aacaggatcg tctgctggtt     540
gaactggaac agccgctgag cagcattctg cagaaatgga atttgccgg tgttaaagtt     600 gataccaaac gtctggaaca atgggtaaa gaactggccg aacaactggg caccgttgaa     660
cagcgtattt atgaactggc aggccaagaa tttaacatta tagcccgaa acagctgggc     720 gttatcctgt ttgaaaaact gcagctgccg gttctgaaaa aaccaaaac cggttatagc     780 accagcgcag atgttctgga aaactggca ccgtatcatg aaattgtgga aacattctg     840 cactatcgtc agctgggtaa actgcagagc acctatattg aaggtctgct gaaagttgtg     900
cgtccggata ccaaaaaagt gcataccatt tttaaccagg cactgaccca gaccggtcgt     960
ctgagcagca ccgaaccgaa tctgcagaat attccgattc gtctggaaga aggtcgtaaa    1020
attcgtcagg catttgttcc gagcgaaagc gattggctga ttttgcagc agattatagc    1080
```

```
cagattgaac tgcgtgttct ggcacatatt gccgaagatg ataatctgat ggaagcattt    1140
cgtcgcgatc tggatattca taccaaaacc gccatggata tttttcaggt tagcgaagat    1200
gaagtgaccc cgaatatgcg tcgtcaggca aaagcagtta attttggtat tgtgtatggc    1260
atcagcgatt atggtctggc acagaatctg aatattagcc gtaaagaagc agccgaattt    1320
atcgaacgtt actttcagag ctttccgggt gttaaacgct atatggaaaa cattgtccaa    1380
gaagccaaac agaaaggtta tgttaccacc ctgctgcatc gtcgtcgtta tctgccgcgt    1440
attaccagcc gtaactttaa tgttcgtagc tttgcagaac gcatggcaat gaataccccg    1500
attcagggta gcgcagcaga tattatcaaa aaagccatga tcgatctgaa cgcacgtctg    1560
aaagaagaac gtctgcaggc acatttactg ctgcaggttc atgatgaact gattctggaa    1620
gcaccgaaag aagaaatgga acgtctttgt cgtctggttc cggaagttat ggaacaggca    1680
gttaccctgc gtgttccgct gaaagttgat tatcgttatg gtagcacctg gtatgatgcc    1740
aaataa                                                               1746
```

<210> SEQ ID NO 63
<211> LENGTH: 606
<212> TYPE: PRT
<213> ORGANISM: Artificial Sequence
<220> FEATURE:
<223> OTHER INFORMATION: Synthetic

<400> SEQUENCE: 63

```
Met Val Ile Ser Tyr Asp Asn Tyr Val Thr Ile Leu Asp Glu Glu Thr
1               5                   10                  15

Leu Lys Ala Trp Ile Ala Lys Leu Glu Lys Ala Pro Val Phe Ala Phe
            20                  25                  30

Asp Thr Glu Thr Asp Ser Leu Asp Asn Ile Ser Ala Asn Leu Val Gly
        35                  40                  45

Leu Ser Phe Ala Ile Glu Pro Gly Val Ala Ala Tyr Ile Pro Val Ala
    50                  55                  60

His Asp Tyr Leu Asp Ala Pro Asp Gln Ile Ser Arg Glu Arg Ala Leu
65                  70                  75                  80

Glu Leu Leu Lys Pro Leu Leu Glu Asp Glu Lys Ala Leu Lys Val Gly
                85                  90                  95

Gln Asn Leu Lys Tyr Asp Arg Gly Ile Leu Ala Asn Tyr Gly Ile Glu
            100                 105                 110

Leu Arg Gly Ile Ala Phe Asp Thr Met Leu Glu Ser Tyr Ile Leu Asn
        115                 120                 125

Ser Val Ala Gly Arg His Asp Met Asp Ser Leu Ala Glu Arg Trp Leu
    130                 135                 140

Lys His Lys Thr Ile Thr Phe Glu Glu Ile Ala Gly Lys Gly Lys Asn
145                 150                 155                 160

Gln Leu Thr Phe Asn Gln Ile Ala Leu Glu Glu Ala Gly Arg Tyr Ala
                165                 170                 175

Ala Glu Asp Ala Asp Val Thr Leu Gln Leu His Leu Lys Met Trp Pro
            180                 185                 190

Asp Leu Gln Lys His Lys Gly Pro Leu Asn Val Phe Glu Asn Ile Glu
        195                 200                 205

Met Pro Leu Val Pro Val Leu Ser Arg Ile Glu Arg Asn Gly Val Lys
    210                 215                 220

Ile Asp Pro Lys Val Leu His Asn His Ser Glu Glu Leu Thr Leu Arg
225                 230                 235                 240
```

```
Leu Ala Glu Leu Glu Lys Lys Ala His Glu Ile Ala Gly Glu Glu Phe
                245                 250                 255

Asn Leu Ser Ser Thr Lys Gln Leu Gln Thr Ile Leu Phe Glu Lys Gln
            260                 265                 270

Gly Ile Lys Pro Leu Lys Lys Thr Pro Gly Gly Ala Pro Ser Thr Ser
        275                 280                 285

Glu Glu Val Leu Glu Glu Leu Ala Leu Asp Tyr Pro Leu Pro Lys Val
    290                 295                 300

Ile Leu Glu Tyr Arg Gly Leu Ala Lys Leu Lys Ser Thr Tyr Thr Asp
305                 310                 315                 320

Lys Leu Pro Leu Met Ile Asn Pro Lys Thr Gly Arg Val His Thr Ser
                325                 330                 335

Tyr His Gln Ala Val Thr Ala Thr Gly Arg Leu Ser Ser Thr Asp Pro
            340                 345                 350

Asn Leu Gln Asn Ile Pro Val Arg Asn Glu Glu Gly Arg Arg Ile Arg
        355                 360                 365

Gln Ala Phe Ile Ala Pro Glu Asp Tyr Val Ile Val Ser Ala Asp Tyr
    370                 375                 380

Ser Gln Ile Glu Leu Arg Ile Met Ala His Leu Ser Arg Asp Lys Gly
385                 390                 395                 400

Leu Leu Thr Ala Phe Ala Glu Gly Lys Asp Ile His Arg Ala Thr Ala
                405                 410                 415

Ala Glu Val Phe Gly Leu Pro Leu Glu Thr Val Thr Ser Glu Gln Arg
            420                 425                 430

Arg Ser Ala Lys Ala Ile Asn Phe Gly Leu Ile Tyr Gly Met Ser Ala
        435                 440                 445

Phe Gly Leu Ala Arg Gln Leu Asn Ile Pro Arg Lys Glu Ala Gln Lys
    450                 455                 460

Tyr Met Asp Leu Tyr Phe Glu Arg Tyr Pro Gly Val Leu Glu Tyr Met
465                 470                 475                 480

Glu Arg Thr Arg Ala Gln Ala Lys Glu Gln Gly Tyr Val Glu Thr Leu
                485                 490                 495

Asp Gly Arg Arg Leu Tyr Leu Pro Asp Ile Lys Ser Ser Asn Gly Ala
            500                 505                 510

Arg Arg Ala Ala Ala Glu Arg Ala Ala Ile Asn Ala Pro Met Gln Gly
        515                 520                 525

Thr Ala Ala Asp Ile Ile Lys Arg Ala Met Ile Ala Val Asp Ala Trp
    530                 535                 540

Leu Gln Ala Glu Gln Pro Arg Val Arg Met Ile Met Gln Val His Asp
545                 550                 555                 560

Glu Leu Val Phe Glu Val His Lys Asp Asp Val Asp Ala Val Ala Lys
                565                 570                 575

Gln Ile His Gln Leu Met Glu Asn Cys Thr Arg Leu Asp Val Pro Leu
            580                 585                 590

Leu Val Glu Val Gly Ser Gly Glu Asn Trp Asp Gln Ala His
        595                 600                 605

<210> SEQ ID NO 64
<211> LENGTH: 581
<212> TYPE: PRT
<213> ORGANISM: Artificial Sequence
<220> FEATURE:
<223> OTHER INFORMATION: Synthetic

<400> SEQUENCE: 64
```

```
Met Ala Lys Met Ala Phe Thr Leu Ala Asp Arg Val Thr Glu Glu Met
 1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Asn Glu Arg Gly Arg
            35                  40                  45

Phe Phe Leu Arg Pro Glu Thr Ala Leu Ala Asp Pro Gln Phe Val Ala
 50                  55                  60

Trp Leu Gly Asp Glu Thr Lys Lys Ser Met Phe Asp Ser Lys Arg
 65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Lys Gln Arg Ile Tyr
210                 215                 220

Glu Leu Ala Gly Gln Glu Phe Asn Ile Arg Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
            275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Lys Tyr Gly Leu Ala Gln Asn Leu Asn Ile
```

```
                        420                 425                 430
Ser Arg Lys Glu Ala Ala Glu Phe Ile Glu Arg Tyr Phe Gln Ser Phe
                435                 440                 445

Pro Gly Val Lys Arg Tyr Met Glu Asn Ile Val Gln Glu Ala Lys Gln
            450                 455                 460

Lys Gly Tyr Val Thr Thr Leu Leu His Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
        530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 65
<211> LENGTH: 581
<212> TYPE: PRT
<213> ORGANISM: Artificial Sequence
<220> FEATURE:
<223> OTHER INFORMATION: Synthetic

<400> SEQUENCE: 65

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu Arg Gly Arg
            35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
```

```
                195                 200                 205
Gly Lys Glu Leu Ala Glu Gln Leu Gly Thr Val Lys Gln Arg Ile Tyr
210                 215                 220
Glu Leu Ala Gly Gln Glu Phe Asn Ile Arg Ser Pro Lys Gln Leu Gly
225                 230                 235                 240
Val Ile Leu Phe Glu Lys Leu Gln Leu Pro Val Leu Lys Lys Thr Lys
                245                 250                 255
Thr Gly Tyr Ser Thr Ser Ala Asp Val Leu Glu Lys Leu Ala Pro Tyr
            260                 265                 270
His Glu Ile Val Glu Asn Ile Leu His Tyr Arg Gln Leu Gly Lys Leu
                275                 280                 285
Gln Ser Thr Tyr Ile Glu Gly Leu Leu Lys Val Val Arg Pro Asp Thr
290                 295                 300
Lys Lys Val His Thr Ile Phe Asn Gln Ala Leu Thr Gln Thr Gly Arg
305                 310                 315                 320
Leu Ser Ser Thr Glu Pro Asn Leu Gln Asn Ile Pro Ile Arg Leu Glu
                325                 330                 335
Glu Gly Arg Lys Ile Arg Gln Ala Phe Val Pro Ser Glu Ser Asp Trp
            340                 345                 350
Leu Ile Phe Ala Ala Asp Tyr Ser Gln Ile Glu Leu Arg Val Leu Ala
                355                 360                 365
His Ile Ala Glu Asp Asp Asn Leu Met Glu Ala Phe Arg Arg Asp Leu
370                 375                 380
Asp Ile His Thr Lys Thr Ala Met Asp Ile Phe Gln Val Ser Glu Asp
385                 390                 395                 400
Glu Val Thr Pro Asn Met Arg Arg Gln Ala Lys Ala Val Asn Phe Gly
                405                 410                 415
Ile Val Tyr Gly Ile Ser Lys Tyr Gly Leu Ala Gln Asn Leu Asn Ile
            420                 425                 430
Ser Arg Lys Glu Ala Ala Glu Phe Ile Glu Arg Tyr Phe Gln Ser Phe
                435                 440                 445
Pro Gly Val Lys Arg Tyr Met Glu Asn Ile Val Gln Glu Ala Lys Gln
450                 455                 460
Lys Gly Tyr Val Thr Thr Leu Leu Arg Arg Arg Tyr Leu Pro Asp
465                 470                 475                 480
Ile Thr Ser Arg Asn Phe Asn Val Arg Ser Phe Ala Glu Arg Met Ala
                485                 490                 495
Met Asn Thr Pro Ile Gln Gly Ser Ala Ala Asp Ile Ile Lys Lys Ala
            500                 505                 510
Met Ile Asp Leu Asn Ala Arg Leu Lys Glu Glu Arg Leu Gln Ala Ala
                515                 520                 525
Leu Leu Leu Gln Val His Asp Glu Leu Ile Leu Glu Ala Pro Lys Glu
                535                 540
Glu Met Glu Arg Leu Cys Arg Leu Val Pro Glu Val Met Glu Gln Ala
545                 550                 555                 560
Val Thr Leu Arg Val Pro Leu Lys Val Asp Tyr Arg Tyr Gly Ser Thr
                565                 570                 575
Trp Tyr Asp Ala Lys
            580

<210> SEQ ID NO 66
<211> LENGTH: 36
<212> TYPE: DNA
<213> ORGANISM: Artificial Sequence
```

```
<220> FEATURE:
<223> OTHER INFORMATION: Synthetic: Oligo 221
<220> FEATURE:
<221> NAME/KEY: misc_feature
<222> LOCATION: (34)..(34)
<223> OTHER INFORMATION: n is flourescein-dT

<400> SEQUENCE: 66 ttttttttgca ggtgacaggt ttttcctgtc accngc                          36

<210> SEQ ID NO 67
<211> LENGTH: 44
<212> TYPE: DNA
<213> ORGANISM: Artificial Sequence
<220> FEATURE:
<223> OTHER INFORMATION: Synthetic: Hairpin oligo

<400> SEQUENCE: 67
tttttttccc tttcctttcg ggtgacaggt ttttcctgtc accc                  44

<210> SEQ ID NO 68
<211> LENGTH: 1740
<212> TYPE: DNA
<213> ORGANISM: Artificial Sequence
<220> FEATURE:
<223> OTHER INFORMATION: Synthetic

<400> SEQUENCE: 68
atggctaaaa tggcttttac tcttgctgat cgtgttactg aagaaatgct tgctgataaa    60
gctgctcttg ttgttgaagt tgttgaagaa aattatcatg atgctcctat tgttggtatt   120
gctgttgtta atgaacgtgg tcgttttttt cttcgtcctg aaactgctct tgctgatcct   180
caatttgttg cttggcttgg tgatgaaact aaaaaaaaat ctatgtttga ttctaaacgt   240
gctgctgttg ctcttaaatg gaaggtatt gaactttgtg gtgtttcttt tgatcttctt   300
cttgctgctt atcttcttga tcctgctcaa ggtgttgatg atgttgctgc tgctgctaaa   360
atgaaacaat atgaagctgt tcgtcctgat gaagctgttt atggtaaagg tgctaaacgt   420
gctgttcctg atgaacctgt tcttgctgaa catcttgttc gtaaagctgc tgctatttgg   480
gaacttgaac gtccttttct tgatgaactt cgtcgtaatg aacaagatcg tcttcttgtt   540
gaacttgaac aacctctttc ttctattctt gctgaaatgg aatttgctgg tgttaaagtt   600
gatactaaac gtcttgaaca atgggtaaa gaacttgctg aacaacttgg tactgttaaa   660
caacgtattt atgaacttgc tggtcaagaa tttaatattc gttctcctaa acaacttggt   720
gttattcttt ttgaaaaact tcaacttcct gttcttaaaa aaactaaaac tggttattct   780
acttctgctg atgttcttga aaaacttgct ccttatcatg aaattgttga aaatattctt   840
cattatcgtc aacttggtaa acttcaatct acttatattg aaggtcttct taagttgtt    900 cgtcctgata ctaaaaaagt tcatactatt tttaatcaag ctcttactca aactggtcgt   960
ctttcttcta ctgaacctaa tcttcaaaat attcctattc gtcttgaaga aggtcgtaaa  1020
attcgtcaag cttttgttcc ttctgaatct gattggctta ttttgctgc tgattattct  1080 caaattgaac ttcgtgttct tgctcatatt gctgaagatg ataatcttat ggaagctttt  1140
cgtcgtgatc ttgatattca tactaaaact gctatggata ttttttcaagt ttctgaagat  1200 gaagttactc ctaatatgcg tcgtcaagct aaagctgtta attttggtat tgtttatggt  1260
atttctaaat atggtcttgc tcaaaatctt aatatttctc gtaaagaagc tgctgaattt  1320
attgaacgtt attttcaatc ttttcctggt gttaaacgtt atatggaaaa tattgttcaa  1380
```

-continued

```
gaagctaaac aaaaaggtta tgttactact cttcttcatc gtcgtcgtta tcttcctgat    1440
attacttctc gtaattttaa tgttcgttct tttgctgaac gtatggctat gaatactcct    1500
attcaaggtt ctgctgctga tattattaaa aaagctatga ttgatcttaa tgctcgtctt    1560
aaagaagaac gtcttcaagc tcatcttctt cttcaagttc atgatgaact tattcttgaa    1620
gctcctaaag aagaaatgga acgtctttgt cgtcttgttc ctgaagttat ggaacaagct    1680
gttactcttc gtgttcctct taaagttgat tatcgttatg gttctacttg gtatgatgct    1740
```

<210> SEQ ID NO 69
<211> LENGTH: 832
<212> TYPE: PRT
<213> ORGANISM: Artificial Sequence
<220> FEATURE:
<223> OTHER INFORMATION: Synthetic

<400> SEQUENCE: 69

| Met | Arg | Gly | Met | Leu | Pro | Leu | Phe | Glu | Pro | Lys | Gly | Arg | Val | Leu | Leu |
|---|---|---|---|---|---|---|---|---|---|---|---|---|---|---|---|
| 1 | | | | 5 | | | | | 10 | | | | | 15 | |

| Val | Asp | Gly | His | His | Leu | Ala | Tyr | Arg | Thr | Phe | His | Ala | Leu | Lys | Gly |
|---|---|---|---|---|---|---|---|---|---|---|---|---|---|---|---|
| | | | 20 | | | | | 25 | | | | | 30 | | |

| Leu | Thr | Thr | Ser | Arg | Gly | Glu | Pro | Val | Gln | Ala | Val | Tyr | Gly | Phe | Ala |
|---|---|---|---|---|---|---|---|---|---|---|---|---|---|---|---|
| | | 35 | | | | | 40 | | | | | 45 | | | |

| Lys | Ser | Leu | Leu | Lys | Ala | Leu | Lys | Glu | Asp | Gly | Asp | Ala | Val | Ile | Val |
|---|---|---|---|---|---|---|---|---|---|---|---|---|---|---|---|
| 50 | | | | | 55 | | | | | 60 | | | | | |

| Val | Phe | Asp | Ala | Lys | Ala | Pro | Ser | Phe | Arg | His | Glu | Ala | Tyr | Gly | Gly |
|---|---|---|---|---|---|---|---|---|---|---|---|---|---|---|---|
| 65 | | | | | 70 | | | | | 75 | | | | | 80 |

| Tyr | Lys | Ala | Gly | Arg | Ala | Pro | Thr | Pro | Glu | Asp | Phe | Pro | Arg | Gln | Leu |
|---|---|---|---|---|---|---|---|---|---|---|---|---|---|---|---|
| | | | | 85 | | | | | 90 | | | | | 95 | |

| Ala | Leu | Ile | Lys | Glu | Leu | Val | Asp | Leu | Leu | Gly | Leu | Ala | Arg | Leu | Glu |
|---|---|---|---|---|---|---|---|---|---|---|---|---|---|---|---|
| | | | 100 | | | | | 105 | | | | | 110 | | |

| Val | Pro | Gly | Tyr | Glu | Ala | Asp | Asp | Val | Leu | Ala | Ser | Leu | Ala | Lys | Lys |
|---|---|---|---|---|---|---|---|---|---|---|---|---|---|---|---|
| | | 115 | | | | | 120 | | | | | 125 | | | |

| Ala | Glu | Lys | Glu | Gly | Tyr | Glu | Val | Arg | Ile | Leu | Thr | Ala | Asp | Lys | Asp |
|---|---|---|---|---|---|---|---|---|---|---|---|---|---|---|---|
| | 130 | | | | | 135 | | | | | 140 | | | | |

| Leu | Tyr | Gln | Leu | Leu | Ser | Asp | Arg | Ile | His | Val | Leu | His | Pro | Glu | Gly |
|---|---|---|---|---|---|---|---|---|---|---|---|---|---|---|---|
| 145 | | | | | 150 | | | | | 155 | | | | | 160 |

| Tyr | Leu | Ile | Thr | Pro | Ala | Trp | Leu | Trp | Glu | Lys | Tyr | Gly | Leu | Arg | Pro |
|---|---|---|---|---|---|---|---|---|---|---|---|---|---|---|---|
| | | | | 165 | | | | | 170 | | | | | 175 | |

| Asp | Gln | Trp | Ala | Asp | Tyr | Arg | Ala | Leu | Thr | Gly | Asp | Glu | Ser | Asp | Asn |
|---|---|---|---|---|---|---|---|---|---|---|---|---|---|---|---|
| | | | 180 | | | | | 185 | | | | | 190 | | |

| Leu | Pro | Gly | Val | Lys | Gly | Ile | Gly | Glu | Lys | Thr | Ala | Arg | Lys | Leu | Leu |
|---|---|---|---|---|---|---|---|---|---|---|---|---|---|---|---|
| | | 195 | | | | | 200 | | | | | 205 | | | |

| Glu | Glu | Trp | Gly | Ser | Leu | Glu | Ala | Leu | Leu | Lys | Asn | Leu | Asp | Arg | Leu |
|---|---|---|---|---|---|---|---|---|---|---|---|---|---|---|---|
| | 210 | | | | | 215 | | | | | 220 | | | | |

| Lys | Pro | Ala | Ile | Arg | Glu | Lys | Ile | Leu | Ala | His | Met | Asp | Asp | Leu | Lys |
|---|---|---|---|---|---|---|---|---|---|---|---|---|---|---|---|
| 225 | | | | | 230 | | | | | 235 | | | | | 240 |

| Leu | Ser | Trp | Asp | Leu | Ala | Lys | Val | Arg | Thr | Asp | Leu | Pro | Leu | Glu | Val |
|---|---|---|---|---|---|---|---|---|---|---|---|---|---|---|---|
| | | | | 245 | | | | | 250 | | | | | 255 | |

| Asp | Phe | Ala | Lys | Arg | Arg | Glu | Pro | Asp | Arg | Glu | Arg | Leu | Arg | Ala | Phe |
|---|---|---|---|---|---|---|---|---|---|---|---|---|---|---|---|
| | | | 260 | | | | | 265 | | | | | 270 | | |

| Leu | Glu | Arg | Leu | Glu | Phe | Gly | Ser | Leu | Leu | His | Glu | Phe | Gly | Leu | Leu |
|---|---|---|---|---|---|---|---|---|---|---|---|---|---|---|---|
| | | 275 | | | | | 280 | | | | | 285 | | | |

| Glu | Ser | Pro | Lys | Ala | Leu | Glu | Glu | Ala | Pro | Trp | Pro | Pro | Pro | Glu | Gly |
|---|---|---|---|---|---|---|---|---|---|---|---|---|---|---|---|
| | 290 | | | | | 295 | | | | | 300 | | | | |

```
Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Arg Tyr Val Pro Arg Leu Glu Ala Arg
```

```
            725                 730                 735
Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 70
<211> LENGTH: 876
<212> TYPE: PRT
<213> ORGANISM: Artificial Sequence
<220> FEATURE:
<223> OTHER INFORMATION: Synthetic

<400> SEQUENCE: 70

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
            35                  40                  45

Glu Glu Pro Thr His Met Leu Val Ala Phe Asp Ala Gly Lys Thr Thr
        50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
            85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
            115                 120                 125

Lys Val Ile Ser Gly Asp Arg Asp Leu Thr Gln Leu Ala Ser Pro His
            130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
            165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
            195                 200                 205

Gly Thr Val Glu Asn Val Leu Ala Ser Ile Asp Glu Ile Lys Gly Glu
            210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
            245                 250                 255

Asp Asp Ile Ala Tyr Gln Gly Glu Asp Arg Glu Lys Val Val Ala Leu
```

```
                260                 265                 270
Phe Lys Glu Leu Gly Phe Gln Ser Phe Leu Glu Lys Met Glu Ser Pro
            275                 280                 285

Ser Ser Glu Glu Glu Lys Pro Leu Ala Lys Met Ala Phe Thr Leu Ala
        290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Ala Ala Tyr Leu
385                 390                 395                 400

Leu Asp Pro Ala Gln Gly Val Asp Val Ala Ala Ala Lys Met
                405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
        435                 440                 445

Arg Lys Ala Ala Ala Ile Trp Glu Leu Glu Arg Pro Phe Leu Asp Glu
    450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
        515                 520                 525

Asn Ser Pro Lys Gln Leu Gly Val Ile Leu Phe Glu Lys Leu Gln Leu
    530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
                565                 570                 575

Tyr Arg Gln Leu Gly Lys Leu Gln Ser Thr Tyr Ile Glu Gly Leu Leu
            580                 585                 590

Lys Val Val Arg Pro Asp Thr Lys Lys Val His Thr Ile Phe Asn Gln
        595                 600                 605

Ala Leu Thr Gln Thr Gly Arg Leu Ser Ser Thr Glu Pro Asn Leu Gln
    610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
                645                 650                 655

Ile Glu Leu Arg Val Leu Ala His Ile Ala Glu Asp Asp Asn Leu Met
            660                 665                 670

Glu Ala Phe Arg Arg Asp Leu Asp Ile His Thr Lys Thr Ala Met Asp
        675                 680                 685
```

-continued

```
Ile Phe Gln Val Ser Glu Asp Glu Val Thr Pro Asn Met Arg Arg Gln
    690             695                 700
Ala Lys Ala Val Asn Phe Gly Ile Val Tyr Gly Ile Ser Asp Tyr Gly
705                 710                 715                 720
Leu Ala Gln Asn Leu Asn Ile Ser Arg Lys Glu Ala Ala Glu Phe Ile
                725                 730                 735
Glu Arg Tyr Phe Glu Ser Phe Pro Gly Val Lys Arg Tyr Met Glu Asn
                740                 745                 750
Ile Val Gln Glu Ala Lys Gln Lys Gly Tyr Val Thr Thr Leu Leu His
            755                 760                 765
Arg Arg Arg Tyr Leu Pro Asp Ile Thr Ser Arg Asn Phe Arg Val Arg
    770                 775                 780
Ser Phe Ala Glu Arg Met Ala Met Asn Thr Pro Ile Gln Gly Ser Ala
785                 790                 795                 800
Ala Asp Ile Ile Lys Lys Ala Met Ile Asp Leu Asn Ala Arg Leu Lys
                805                 810                 815
Glu Glu Arg Leu Gln Ala His Leu Leu Leu Gln Val His Asp Glu Leu
                820                 825                 830
Ile Leu Glu Ala Pro Lys Glu Met Glu Arg Leu Cys Arg Leu Val
            835                 840                 845
Pro Glu Val Met Glu Gln Ala Val Thr Leu Arg Val Pro Leu Lys Val
    850                 855                 860
Asp Tyr His Tyr Gly Ser Thr Trp Tyr Asp Ala Lys
865                 870                 875
```

<210> SEQ ID NO 71
<211> LENGTH: 876
<212> TYPE: PRT
<213> ORGANISM: Artificial Sequence
<220> FEATURE:
<223> OTHER INFORMATION: Synthetic

<400> SEQUENCE: 71

```
Met Lys Lys Lys Leu Val Leu Ile Asp Gly Ser Ser Val Ala Tyr Arg
1               5                   10                  15
Ala Phe Phe Ala Leu Pro Leu Leu His Asn Asp Lys Gly Ile His Thr
                20                  25                  30
Asn Ala Val Tyr Gly Phe Thr Met Met Leu Asn Lys Ile Leu Ala Glu
                35                  40                  45
Glu Glu Pro Thr His Met Leu Val Ala Phe Asp Ala Gly Lys Thr Thr
    50                  55                  60
Phe Arg His Glu Ala Phe Gln Glu Tyr Lys Gly Gly Arg Gln Gln Thr
65                  70                  75                  80
Pro Pro Glu Leu Ser Glu Gln Phe Pro Leu Leu Arg Glu Leu Leu Arg
                85                  90                  95
Ala Tyr Arg Ile Pro Ala Tyr Glu Leu Glu Asn Tyr Glu Ala Asp Asp
                100                 105                 110
Ile Ile Gly Thr Leu Ala Ala Arg Ala Glu Gln Glu Gly Phe Glu Val
            115                 120                 125
Lys Val Ile Ser Gly Asp Arg Asp Leu Thr Gln Leu Ala Ser Pro His
    130                 135                 140
Val Thr Val Asp Ile Thr Lys Lys Gly Ile Thr Asp Ile Glu Pro Tyr
145                 150                 155                 160
Thr Pro Glu Thr Val Arg Glu Lys Tyr Gly Leu Thr Pro Glu Gln Ile
                165                 170                 175
```

```
Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
            195                 200                 205

Gly Thr Val Glu Asn Val Leu Ala Ser Ile Asp Glu Ile Lys Gly Glu
            210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Lys Val Val Ala Leu
                260                 265                 270

Phe Lys Glu Leu Gly Phe Gln Ser Phe Leu Lys Met Glu Ser Pro
            275                 280                 285

Ser Ser Glu Glu Glu Lys Pro Leu Ala Lys Met Ala Phe Thr Leu Ala
            290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
            355                 360                 365

Ser Met Phe Asp Ser Lys Arg Ala Ala Val Ala Leu Lys Trp Lys Gly
            370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Asp Val Ala Ala Ala Lys Met
            405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
            435                 440                 445

Arg Lys Ala Ala Ala Ile Trp Glu Leu Glu Arg Pro Phe Leu Asp Glu
450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
            530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
                565                 570                 575

Tyr Arg Gln Leu Gly Lys Leu Gln Ser Thr Tyr Ile Glu Gly Leu Leu
            580                 585                 590
```

```
Lys Val Val Arg Pro Asp Thr Lys Val His Thr Ile Phe Asn Gln
            595                 600                 605

Ala Leu Thr Gln Thr Gly Arg Leu Ser Ser Thr Glu Pro Asn Leu Gln
610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
            645                 650                 655

Ile Glu Leu Arg Val Leu Ala His Ile Ala Glu Asp Asn Leu Met
            660                 665                 670

Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
690                 695                 700

Ala Lys Ala Val Asn Phe Gly Ile Val Tyr Gly Ile Ser Lys Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
            755                 760                 765

Arg Arg Arg Tyr Leu Pro Asp Ile Thr Ser Arg Asn Phe Arg Val Arg
            770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
                805                 810                 815

Glu Glu Arg Leu Gln Ala His Leu Leu Leu Gln Val His Asp Glu Leu
            820                 825                 830

Ile Leu Glu Ala Pro Lys Glu Glu Met Glu Arg Leu Cys Arg Leu Val
            835                 840                 845

Pro Glu Val Met Glu Gln Ala Val Thr Leu Arg Val Pro Leu Lys Val
850                 855                 860

Asp Tyr His Tyr Gly Ser Thr Trp Tyr Asp Ala Lys
865                 870                 875

<210> SEQ ID NO 72
<211> LENGTH: 876
<212> TYPE: PRT
<213> ORGANISM: Artificial Sequence
<220> FEATURE:
<223> OTHER INFORMATION: Synthetic

<400> SEQUENCE: 72

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
            35                  40                  45

Glu Glu Pro Thr His Met Leu Val Ala Phe Asp Ala Gly Lys Thr Thr
        50                  55                  60

Phe Arg His Glu Ala Phe Gln Glu Tyr Lys Gly Gly Arg Gln Gln Thr
65                  70                  75                  80
```

```
Pro Pro Glu Leu Ser Glu Gln Phe Pro Leu Arg Glu Leu Leu Arg
            85                  90                  95
Ala Tyr Arg Ile Pro Ala Tyr Glu Leu Glu Asn Tyr Glu Ala Asp Asp
        100                 105                 110
Ile Ile Gly Thr Leu Ala Ala Arg Ala Glu Gln Glu Gly Phe Glu Val
        115                 120                 125
Lys Val Ile Ser Gly Asp Arg Asp Leu Thr Gln Leu Ala Ser Pro His
        130                 135                 140
Val Thr Val Asp Ile Thr Lys Lys Gly Ile Thr Asp Ile Glu Pro Tyr
145                 150                 155                 160
Thr Pro Glu Thr Val Arg Glu Lys Tyr Gly Leu Thr Pro Glu Gln Ile
                165                 170                 175
Val Asp Leu Lys Gly Leu Met Gly Asp Lys Ser Asp Asn Ile Pro Gly
            180                 185                 190
Val Pro Gly Ile Gly Glu Lys Thr Ala Val Lys Leu Leu Arg Gln Phe
        195                 200                 205
Gly Thr Val Glu Asn Val Leu Ala Ser Ile Asp Glu Ile Lys Gly Glu
        210                 215                 220
Lys Leu Lys Glu Thr Leu Arg Gln His Arg Glu Met Ala Leu Leu Ser
225                 230                 235                 240
Lys Lys Leu Ala Ala Ile Arg Arg Asp Ala Pro Val Glu Leu Ser Leu
                245                 250                 255
Asp Asp Ile Ala Tyr Gln Gly Glu Asp Arg Glu Lys Val Val Ala Leu
            260                 265                 270
Phe Lys Glu Leu Gly Phe Gln Ser Phe Leu Glu Lys Met Glu Ser Pro
        275                 280                 285
Ser Ser Glu Glu Glu Lys Pro Leu Ala Lys Met Ala Phe Thr Leu Ala
        290                 295                 300
Asp Arg Val Thr Glu Glu Met Leu Ala Asp Lys Ala Ala Leu Val Val
305                 310                 315                 320
Glu Val Val Glu Glu Asn Tyr His Asp Ala Pro Ile Val Gly Ile Ala
                325                 330                 335
Val Val Asn Glu His Gly Arg Phe Phe Leu Arg Pro Glu Thr Ala Leu
            340                 345                 350
Ala Asp Pro Gln Phe Val Ala Trp Leu Gly Asp Glu Thr Lys Lys Lys
        355                 360                 365
Ser Met Phe Asp Ser Lys Arg Ala Ala Val Ala Leu Lys Trp Lys Gly
        370                 375                 380
Ile Glu Leu Cys Gly Val Ser Phe Asp Leu Leu Leu Ala Ala Tyr Leu
385                 390                 395                 400
Leu Asp Pro Ala Gln Gly Val Asp Asp Val Ala Ala Ala Lys Met
                405                 410                 415
Lys Gln Tyr Glu Ala Val Arg Pro Asp Glu Ala Val Tyr Gly Lys Gly
            420                 425                 430
Ala Lys Arg Ala Val Pro Asp Glu Pro Val Leu Ala Glu His Leu Val
        435                 440                 445
Arg Lys Ala Ala Ala Ile Trp Glu Leu Glu Arg Pro Phe Leu Asp Glu
        450                 455                 460
Leu Arg Arg Asn Glu Gln Asp Arg Leu Leu Val Glu Leu Glu Gln Pro
465                 470                 475                 480
Leu Ser Ser Ile Leu Ala Glu Met Glu Phe Ala Gly Val Lys Val Asp
                485                 490                 495
Thr Lys Arg Leu Glu Gln Met Gly Lys Glu Leu Ala Glu Gln Leu Gly
```

500                 505                 510
Thr Val Glu Gln Arg Ile Tyr Glu Leu Ala Gly Gln Glu Phe Asn Ile
            515                 520                 525
Asn Ser Pro Lys Gln Leu Gly Val Ile Leu Phe Glu Lys Leu Gln Leu
        530                 535                 540
Pro Val Leu Lys Lys Thr Lys Thr Gly Tyr Ser Thr Ser Ala Asp Val
545                 550                 555                 560
Leu Glu Lys Leu Ala Pro Tyr Asn Glu Ile Val Glu Asn Ile Leu His
                565                 570                 575
Tyr Arg Gln Leu Gly Lys Leu Gln Ser Thr Tyr Ile Glu Gly Leu Leu
            580                 585                 590
Lys Val Val Arg Pro Asp Thr Lys Lys Val His Thr Ile Phe Asn Gln
        595                 600                 605
Ala Leu Thr Gln Thr Gly Arg Leu Ser Ser Thr Glu Pro Asn Leu Gln
        610                 615                 620
Asn Ile Pro Ile Arg Leu Glu Glu Gly Arg Lys Ile Arg Gln Ala Phe
625                 630                 635                 640
Val Pro Ser Glu Ser Asp Trp Leu Ile Phe Ala Ala Asp Tyr Ser Gln
                645                 650                 655
Ile Glu Leu Arg Val Leu Ala His Ile Ala Glu Asp Asp Asn Leu Met
            660                 665                 670
Glu Ala Phe Arg Arg Asp Leu Asp Ile His Thr Lys Thr Ala Met Asp
        675                 680                 685
Ile Phe Gln Val Ser Glu Asp Glu Val Thr Pro Asn Met Arg Arg Gln
        690                 695                 700
Ala Lys Ala Val Asn Phe Gly Ile Val Tyr Gly Ile Ser Lys Tyr Gly
705                 710                 715                 720
Leu Ala Gln Asn Leu Asn Ile Ser Arg Lys Glu Ala Ala Glu Phe Ile
                725                 730                 735
Glu Arg Tyr Phe Glu Ser Phe Pro Gly Val Lys Arg Tyr Met Glu Asn
            740                 745                 750
Ile Val Gln Glu Ala Lys Gln Lys Gly Tyr Val Thr Thr Leu Leu His
        755                 760                 765
Arg Arg Arg Tyr Leu Pro Asp Ile Thr Ser Arg Asn Phe Asn Val Arg
770                 775                 780
Ser Phe Ala Glu Arg Met Ala Met Asn Thr Pro Ile Gln Gly Ser Ala
785                 790                 795                 800
Ala Asp Ile Ile Lys Lys Ala Met Ile Asp Leu Asn Ala Arg Leu Lys
                805                 810                 815
Glu Glu Arg Leu Gln Ala His Leu Leu Leu Gln Val His Asp Glu Leu
            820                 825                 830
Ile Leu Glu Ala Pro Lys Glu Met Glu Arg Leu Cys Arg Leu Val
        835                 840                 845
Pro Glu Val Met Glu Gln Ala Val Thr Leu Arg Val Pro Leu Lys Val
        850                 855                 860
Asp Tyr His Tyr Gly Ser Thr Trp Tyr Asp Ala Lys
865                 870                 875

<210> SEQ ID NO 73
<211> LENGTH: 876
<212> TYPE: PRT
<213> ORGANISM: Artificial Sequence
<220> FEATURE:
<223> OTHER INFORMATION: Synthetic

<400> SEQUENCE: 73

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
    50                  55                  60

Phe Arg His Glu Ala Phe Gln Glu Tyr Lys Gly Gly Arg Gln Gln Thr
65              70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
        115                 120                 125

Lys Val Ile Ser Gly Asp Arg Asp Leu Thr Gln Leu Ala Ser Pro His
    130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
        195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
    290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Val Ala Ala Ala Lys Met
                405                 410                 415

```
Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
            435                 440                 445

Arg Lys Ala Ala Ala Ile Trp Glu Leu Glu Arg Pro Phe Leu Asp Glu
            450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu Met
                565                 570                 575

Tyr Arg Gln Leu Gly Lys Leu Gln Ser Thr Tyr Ile Glu Gly Leu Leu
            580                 585                 590

Lys Val Val Arg Pro Asp Thr Lys Lys Val His Thr Ile Phe Asn Gln
            595                 600                 605

Ala Leu Thr Gln Thr Gly Arg Leu Ser Ser Thr Glu Pro Asn Leu Gln
            610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
                645                 650                 655

Ile Glu Leu Arg Val Leu Ala His Ile Ala Glu Asp Asp Asn Leu Met
            660                 665                 670

Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
            690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
            755                 760                 765

Arg Arg Arg Tyr Leu Pro Asp Ile Thr Ser Arg Asn Phe Arg Val Arg
            770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
                805                 810                 815

Glu Glu Arg Leu Gln Ala His Leu Leu Leu Gln Val His Asp Glu Leu
            820                 825                 830
```

Ile Leu Glu Ala Pro Lys Glu Glu Met Glu Arg Leu Cys Arg Leu Val
835                 840                 845

Pro Glu Val Met Glu Gln Ala Val Thr Leu Arg Val Pro Leu Lys Val
850                 855                 860

Asp Tyr His Tyr Gly Ser Thr Trp Tyr Asp Ala Lys
865                 870                 875

<210> SEQ ID NO 74
<211> LENGTH: 876
<212> TYPE: PRT
<213> ORGANISM: Artificial Sequence
<220> FEATURE:
<223> OTHER INFORMATION: Synthetic

<400> SEQUENCE: 74

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
    50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
        115                 120                 125

Lys Val Ile Ser Gly Asp Arg Asp Leu Thr Gln Leu Ala Ser Pro His
130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
        195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Lys Met Glu Ser Pro
        275                 280                 285

Ser Ser Glu Glu Glu Lys Pro Leu Ala Lys Met Ala Phe Thr Leu Ala
    290                 295                 300

Asp Arg Val Thr Glu Glu Met Leu Ala Asp Lys Ala Ala Leu Val Val
305                 310                 315                 320

-continued

Glu Val Val Glu Glu Asn Tyr His Asp Ala Pro Ile Val Gly Ile Ala
            325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
            355                 360                 365

Ser Met Phe Asp Ser Lys Arg Ala Ala Val Ala Leu Lys Trp Lys Gly
            370                 375                 380

Ile Glu Leu Cys Gly Val Ser Phe Asp Leu Leu Ala Ala Tyr Leu
385                 390                 395                 400

Leu Asp Pro Ala Gln Gly Val Asp Asp Val Ala Ala Ala Lys Met
            405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
            435                 440                 445

Arg Lys Ala Ala Ala Ile Trp Glu Leu Glu Arg Pro Phe Leu Asp Glu
            450                 455                 460

Leu Arg Arg Asn Glu Gln Asp Arg Leu Leu Val Glu Leu Gln Pro
465                 470                 475                 480

Leu Ser Ser Ile Leu Ala Glu Met Glu Phe Ala Gly Val Lys Val Asp
            485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
            565                 570                 575

Tyr Arg Gln Leu Gly Lys Leu Gln Ser Thr Tyr Ile Glu Gly Leu Leu
            580                 585                 590

Lys Val Val Arg Pro Asp Thr Lys Lys Val His Thr Ile Phe Asn Gln
            595                 600                 605

Ala Leu Thr Gln Thr Gly Arg Leu Ser Ser Thr Glu Pro Asn Leu Gln
            610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
            645                 650                 655

Ile Glu Leu Arg Val Leu Ala His Ile Ala Glu Asp Asp Asn Leu Met
            660                 665                 670

Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
            690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Ser Arg Lys Glu Ala Ala Glu Phe Ile
            725                 730                 735

Glu Arg Tyr Phe Glu Ser Phe Pro Gly Val Lys Arg Tyr Met Glu Asn

```
                  740                 745                 750
Ile Val Gln Glu Ala Lys Gln Lys Gly Tyr Val Thr Thr Leu Leu His
            755                 760                 765
Arg Arg Arg Tyr Leu Pro Asp Ile Thr Ser Arg Asn Phe Arg Val Arg
            770                 775                 780
Ser Phe Ala Glu Arg Met Ala Met Asn Thr Pro Ile Gln Gly Ser Ala
785                 790                 795                 800
Ala Asp Ile Ile Lys Lys Ala Met Ile Asp Leu Asn Ala Arg Leu Lys
            805                 810                 815
Glu Glu Arg Leu Gln Ala Ser Leu Leu Leu Gln Val His Asp Glu Leu
            820                 825                 830
Ile Leu Glu Ala Pro Lys Glu Glu Met Glu Arg Leu Cys Arg Leu Val
            835                 840                 845
Pro Glu Val Met Glu Gln Ala Val Thr Leu Arg Val Pro Leu Lys Val
            850                 855                 860
Asp Tyr His Tyr Gly Ser Thr Trp Tyr Asp Ala Lys
865                 870                 875
```

<210> SEQ ID NO 75
<211> LENGTH: 876
<212> TYPE: PRT
<213> ORGANISM: Artificial Sequence
<220> FEATURE:
<223> OTHER INFORMATION: Synthetic

<400> SEQUENCE: 75

```
Met Lys Lys Lys Leu Val Leu Ile Asp Gly Ser Ser Val Ala Tyr Arg
1               5                   10                  15
Ala Phe Phe Ala Leu Pro Leu Leu His Asn Asp Lys Gly Ile His Thr
            20                  25                  30
Asn Ala Val Tyr Gly Phe Thr Met Met Leu Asn Lys Ile Leu Ala Glu
            35                  40                  45
Glu Glu Pro Thr His Met Leu Val Ala Phe Asp Ala Gly Lys Thr Thr
        50                  55                  60
Phe Arg His Glu Ala Phe Gln Glu Tyr Lys Gly Gly Arg Gln Gln Thr
65              70                  75                  80
Pro Pro Glu Leu Ser Glu Gln Phe Pro Leu Leu Arg Glu Leu Leu Arg
            85                  90                  95
Ala Tyr Arg Ile Pro Ala Tyr Glu Leu Glu Asn Tyr Glu Ala Asp Asp
            100                 105                 110
Ile Ile Gly Thr Leu Ala Ala Arg Ala Glu Gln Glu Gly Phe Glu Val
            115                 120                 125
Lys Val Ile Ser Gly Asp Arg Asp Leu Thr Gln Leu Ala Ser Pro His
            130                 135                 140
Val Thr Val Asp Ile Thr Lys Lys Gly Ile Thr Asp Ile Glu Pro Tyr
145                 150                 155                 160
Thr Pro Glu Thr Val Arg Glu Lys Tyr Gly Leu Thr Pro Glu Gln Ile
            165                 170                 175
Val Asp Leu Lys Gly Leu Met Gly Asp Lys Ser Asp Asn Ile Pro Gly
            180                 185                 190
Val Pro Gly Ile Gly Glu Lys Thr Ala Val Lys Leu Leu Arg Gln Phe
            195                 200                 205
Gly Thr Val Glu Asn Val Leu Ala Ser Ile Asp Glu Ile Lys Gly Glu
            210                 215                 220
Lys Leu Lys Glu Thr Leu Arg Gln His Arg Glu Met Ala Leu Leu Ser
```

```
                225                 230                 235                 240
Lys Lys Leu Ala Ala Ile Arg Arg Asp Ala Pro Val Glu Leu Ser Leu
                    245                 250                 255

Asp Asp Ile Ala Tyr Gln Gly Glu Asp Arg Glu Lys Val Val Ala Leu
                    260                 265                 270

Phe Lys Glu Leu Gly Phe Gln Ser Phe Leu Glu Lys Met Glu Ser Pro
                    275                 280                 285

Ser Ser Glu Glu Glu Lys Pro Leu Ala Lys Met Ala Phe Thr Leu Ala
        290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                        325                 330                 335

Val Val Asn Glu His Gly Arg Phe Phe Leu Arg Pro Glu Thr Ala Leu
                340                 345                 350

Ala Asp Pro Gln Phe Val Ala Trp Leu Gly Asp Glu Thr Lys Lys Lys
                355                 360                 365

Ser Met Phe Asp Ser Lys Arg Ala Ala Val Ala Leu Lys Trp Lys Gly
        370                 375                 380

Ile Glu Leu Cys Gly Val Ser Phe Asp Leu Leu Ala Ala Tyr Leu
385                 390                 395                 400

Leu Asp Pro Ala Gln Gly Val Asp Val Ala Ala Ala Lys Met
                    405                 410                 415

Lys Gln Tyr Glu Ala Val Arg Pro Asp Glu Ala Val Tyr Gly Lys Gly
                    420                 425                 430

Ala Lys Arg Ala Val Pro Asp Glu Pro Val Leu Ala Glu His Leu Val
                435                 440                 445

Arg Lys Ala Ala Ala Ile Trp Glu Leu Glu Arg Pro Phe Leu Asp Glu
                450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                    485                 490                 495

Thr Lys Arg Leu Glu Gln Met Gly Lys Glu Leu Ala Glu Gln Leu Gly
                500                 505                 510

Thr Val Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
        530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
                        565                 570                 575

Tyr Arg Gln Leu Gly Lys Leu Gln Ser Thr Tyr Ile Glu Gly Leu Leu
                580                 585                 590

Lys Val Val Arg Pro Asp Thr Lys Lys Val His Thr Ile Phe Asn Gln
            595                 600                 605

Ala Leu Thr Gln Thr Gly Arg Leu Ser Ser Thr Glu Pro Asn Leu Gln
        610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
                    645                 650                 655
```

```
Ile Glu Leu Arg Val Leu Ala His Ile Ala Glu Asp Asn Leu Met
            660                 665                 670

Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
            690                 695                 700

Ala Lys Ala Val Asn Phe Gly Ile Val Tyr Gly Ile Ser Lys Tyr Gly
705                 710                 715                 720

Leu Ala Gln Asn Leu Asn Ile Ser Arg Lys Glu Ala Ala Glu Phe Ile
            725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
            755                 760                 765

Arg Arg Arg Tyr Leu Pro Asp Ile Thr Ser Arg Asn Phe Asn Val Arg
            770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
            805                 810                 815

Glu Glu Arg Leu Gln Ala His Leu Leu Leu Gln Val His Asp Glu Leu
            820                 825                 830

Ile Leu Glu Ala Pro Lys Glu Glu Met Glu Arg Leu Cys Arg Leu Val
            835                 840                 845

Pro Glu Val Met Glu Gln Ala Val Thr Leu Arg Val Pro Leu Lys Val
            850                 855                 860

Asp Tyr His Tyr Gly Ser Thr Trp Tyr Asp Ala Lys
865                 870                 875

<210> SEQ ID NO 76
<211> LENGTH: 876
<212> TYPE: PRT
<213> ORGANISM: Artificial Sequence
<220> FEATURE:
<223> OTHER INFORMATION: Synthetic

<400> SEQUENCE: 76

Met Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
            35                  40                  45

Glu Glu Pro Thr His Met Leu Val Ala Phe Asp Ala Gly Lys Thr Thr
            50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
            85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
            115                 120                 125

Lys Val Ile Ser Gly Asp Arg Asp Leu Thr Gln Leu Ala Ser Pro His
            130                 135                 140
```

```
Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
            165                 170                 175

Val Asp Leu Lys Gly Leu Met Gly Asp Lys Ser Asp Asn Ile Pro Gly
        180                 185                 190

Val Pro Gly Ile Gly Glu Lys Thr Ala Val Lys Leu Leu Arg Gln Phe
    195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
            245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
    290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
            325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Asp Val Ala Ala Ala Ala Lys Met
            405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
        435                 440                 445

Arg Lys Ala Ala Ala Ile Trp Glu Leu Glu Arg Pro Phe Leu Asp Glu
    450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
            485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
        530                 535                 540

Pro Val Leu Lys Lys Thr Lys Thr Gly Tyr Ser Thr Ser Ala Asp Val
545                 550                 555                 560
```

```
Leu Glu Lys Leu Ala Pro Tyr His Glu Ile Val Glu Asn Ile Leu Met
                565                 570                 575

Tyr Arg Gln Leu Gly Lys Leu Gln Ser Thr Tyr Ile Glu Gly Leu Leu
            580                 585                 590

Lys Val Val Arg Pro Asp Thr Lys Val His Thr Ile Phe Asn Gln
        595                 600                 605

Ala Leu Thr Gln Thr Gly Arg Leu Ser Ser Thr Glu Pro Asn Leu Gln
        610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
                645                 650                 655

Ile Glu Leu Arg Val Leu Ala His Ile Ala Glu Asp Asp Asn Leu Met
                660                 665                 670

Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
        690                 695                 700

Ala Lys Ala Val Asn Phe Gly Ile Val Tyr Gly Ile Ser Lys Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
                740                 745                 750

Ile Val Gln Glu Ala Lys Gln Lys Gly Tyr Val Thr Thr Leu Leu His
            755                 760                 765

Arg Arg Arg Tyr Leu Pro Asp Ile Thr Ser Arg Asn Phe Arg Val Arg
770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
                805                 810                 815

Glu Glu Arg Leu Gln Ala His Leu Leu Leu Gln Val His Asp Glu Leu
                820                 825                 830

Ile Leu Glu Ala Pro Lys Glu Glu Met Glu Arg Leu Cys Arg Leu Val
            835                 840                 845

Pro Glu Val Met Glu Gln Ala Val Thr Leu Arg Val Pro Leu Lys Val
        850                 855                 860

Asp Tyr His Tyr Gly Ser Thr Trp Tyr Asp Ala Lys
865                 870                 875

<210> SEQ ID NO 77
<211> LENGTH: 876
<212> TYPE: PRT
<213> ORGANISM: Artificial Sequence
<220> FEATURE:
<223> OTHER INFORMATION: Synthetic

<400> SEQUENCE: 77

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45
```

-continued

```
Glu Glu Pro Thr His Met Leu Val Ala Phe Asp Ala Gly Lys Thr Thr
 50                  55                  60
Phe Arg His Glu Ala Phe Gln Glu Tyr Lys Gly Gly Arg Gln Gln Thr
 65                  70                  75                  80
Pro Pro Glu Leu Ser Glu Gln Phe Pro Leu Leu Arg Glu Leu Leu Arg
                 85                  90                  95
Ala Tyr Arg Ile Pro Ala Tyr Glu Leu Glu Asn Tyr Glu Ala Asp Asp
                100                 105                 110
Ile Ile Gly Thr Leu Ala Ala Arg Ala Glu Gln Glu Gly Phe Glu Val
                115                 120                 125
Lys Val Ile Ser Gly Asp Arg Asp Leu Thr Gln Leu Ala Ser Pro His
130                 135                 140
Val Thr Val Asp Ile Thr Lys Lys Gly Ile Thr Asp Ile Glu Pro Tyr
145                 150                 155                 160
Thr Pro Glu Thr Val Arg Glu Lys Tyr Gly Leu Thr Pro Glu Gln Ile
                165                 170                 175
Val Asp Leu Lys Gly Leu Met Gly Asp Lys Ser Asp Asn Ile Pro Gly
                180                 185                 190
Val Pro Gly Ile Gly Glu Lys Thr Ala Val Lys Leu Leu Arg Gln Phe
                195                 200                 205
Gly Thr Val Glu Asn Val Leu Ala Ser Ile Asp Glu Ile Lys Gly Glu
210                 215                 220
Lys Leu Lys Glu Thr Leu Arg Gln His Arg Glu Met Ala Leu Leu Ser
225                 230                 235                 240
Lys Lys Leu Ala Ala Ile Arg Arg Asp Ala Pro Val Glu Leu Ser Leu
                245                 250                 255
Asp Asp Ile Ala Tyr Gln Gly Glu Asp Arg Glu Lys Val Val Ala Leu
                260                 265                 270
Phe Lys Glu Leu Gly Phe Gln Ser Phe Leu Glu Lys Met Glu Ser Pro
                275                 280                 285
Ser Ser Glu Glu Glu Lys Pro Leu Ala Lys Met Ala Phe Thr Leu Ala
                290                 295                 300
Asp Arg Val Thr Glu Glu Met Leu Ala Asp Lys Ala Ala Leu Val Val
305                 310                 315                 320
Glu Val Val Glu Glu Asn Tyr His Asp Ala Pro Ile Val Gly Ile Ala
                325                 330                 335
Val Val Asn Glu His Gly Arg Phe Phe Leu Arg Pro Glu Thr Ala Leu
                340                 345                 350
Ala Asp Pro Gln Phe Val Ala Trp Leu Gly Asp Glu Thr Lys Lys Lys
                355                 360                 365
Ser Met Phe Asp Ser Lys Arg Ala Ala Val Ala Leu Lys Trp Lys Gly
370                 375                 380
Ile Glu Leu Cys Gly Val Ser Phe Asp Leu Leu Leu Ala Ala Tyr Leu
385                 390                 395                 400
Leu Asp Pro Ala Gln Gly Val Asp Val Ala Ala Ala Lys Met
                405                 410                 415
Lys Gln Tyr Glu Ala Val Arg Pro Asp Glu Ala Val Tyr Gly Lys Gly
                420                 425                 430
Ala Lys Arg Ala Val Pro Asp Glu Pro Val Leu Ala Glu His Leu Val
                435                 440                 445
Arg Lys Ala Ala Ala Ile Trp Glu Leu Glu Arg Pro Phe Leu Asp Glu
450                 455                 460
Leu Arg Arg Asn Glu Gln Asp Arg Leu Leu Val Glu Leu Glu Gln Pro
```

```
            465                 470                 475                 480
        Leu Ser Ser Ile Leu Ala Glu Met Glu Phe Ala Gly Val Lys Val Asp
                            485                 490                 495
        Thr Lys Arg Leu Glu Gln Met Gly Lys Glu Leu Ala Glu Gln Leu Gly
                        500                 505                 510
        Thr Val Glu Gln Arg Ile Tyr Glu Leu Ala Gly Gln Glu Phe Asn Ile
                        515                 520                 525
        Asn Ser Pro Lys Gln Leu Gly Val Ile Leu Phe Glu Lys Leu Gln Leu
                    530                 535                 540
        Pro Val Leu Lys Lys Thr Lys Thr Gly Tyr Ser Thr Ser Ala Ala Val
        545                 550                 555                 560
        Leu Glu Lys Leu Ala Pro Tyr Asn Glu Ile Val Glu Asn Ile Leu Met
                            565                 570                 575
        Tyr Arg Gln Leu Gly Lys Leu Gln Ser Thr Tyr Ile Glu Gly Leu Leu
                        580                 585                 590
        Lys Val Val Arg Pro Asp Thr Lys Val His Thr Ile Phe Asn Gln
                    595                 600                 605
        Ala Leu Thr Gln Thr Gly Arg Leu Ser Ser Thr Glu Pro Asn Leu Gln
        610                 615                 620
        Asn Ile Pro Ile Arg Leu Glu Glu Gly Arg Lys Ile Arg Gln Ala Phe
        625                 630                 635                 640
        Val Pro Ser Glu Ser Asp Trp Leu Ile Phe Ala Ala Asp Tyr Ser Gln
                        645                 650                 655
        Ile Glu Leu Arg Val Leu Ala His Ile Ala Glu Asp Asp Asn Leu Met
                        660                 665                 670
        Glu Ala Phe Arg Arg Asp Leu Asp Ile His Thr Lys Thr Ala Met Asp
                        675                 680                 685
        Ile Phe Gln Val Ser Glu Asp Glu Val Thr Pro Asn Met Arg Arg Gln
                        690                 695                 700
        Ala Lys Ala Val Asn Phe Gly Ile Val Tyr Gly Ile Ser Asp Tyr Gly
        705                 710                 715                 720
        Leu Ala Gln Asn Leu Asn Ile Ser Arg Lys Glu Ala Ala Glu Phe Ile
                        725                 730                 735
        Glu Arg Tyr Phe Glu Ser Phe Pro Gly Val Lys Arg Tyr Met Glu Asn
                        740                 745                 750
        Ile Val Gln Glu Ala Lys Gln Lys Gly Tyr Val Thr Thr Leu Leu His
                        755                 760                 765
        Arg Arg Arg Tyr Leu Pro Asp Ile Thr Ser Arg Asn Phe Arg Val Arg
                770                 775                 780
        Ser Phe Ala Arg Arg Met Ala Met Asn Thr Pro Ile Gln Gly Ser Ala
        785                 790                 795                 800
        Ala Asp Ile Ile Lys Lys Ala Met Ile Asp Leu Asn Ala Arg Leu Lys
                        805                 810                 815
        Glu Glu Arg Leu Gln Ala His Leu Leu Leu Gln Val His Asp Glu Leu
                        820                 825                 830
        Ile Leu Glu Ala Pro Lys Glu Glu Met Glu Arg Leu Cys Arg Leu Val
                        835                 840                 845
        Pro Glu Val Met Glu Gln Ala Val Thr Leu Arg Val Pro Leu Lys Val
                        850                 855                 860
        Asp Tyr His Tyr Gly Ser Thr Trp Tyr Asp Ala Lys
        865                 870                 875

<210> SEQ ID NO 78
```

<211> LENGTH: 581
<212> TYPE: PRT
<213> ORGANISM: Artificial Sequence
<220> FEATURE:
<223> OTHER INFORMATION: Synthetic

<400> SEQUENCE: 78

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Asn Glu Arg Gly Arg
        35                  40                  45

Phe Phe Leu Arg Pro Glu Thr Ala Leu Ala Asp Pro Gln Phe Val Ala
50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
370                 375                 380
```

-continued

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
            405                 410                 415

Ile Val Tyr Gly Ile Ser Lys Tyr Gly Leu Ala Gln Asn Leu Asn Ile
        420                 425                 430

Ser Arg Lys Glu Ala Ala Glu Phe Ile Glu Arg Tyr Phe Gln Ser Phe
    435                 440                 445

Pro Gly Val Lys Arg Tyr Met Glu Asn Ile Val Gln Glu Ala Lys Gln
450                 455                 460

Lys Gly Tyr Val Thr Thr Leu Leu His Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 79
<211> LENGTH: 581
<212> TYPE: PRT
<213> ORGANISM: Artificial Sequence
<220> FEATURE:
<223> OTHER INFORMATION: Synthetic

<400> SEQUENCE: 79

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

```
Glu Leu Glu Arg Pro Phe Leu Asp Glu Leu Arg Arg Asn Glu Gln Asp
                165                 170                 175

Arg Leu Leu Val Glu Leu Gln Pro Leu Ser Ser Ile Leu Ala Glu
            180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
            210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Ala Val Leu Glu Lys Leu Ala Pro Tyr
            260                 265                 270

Asn Glu Ile Val Glu Asn Ile Leu Met Tyr Arg Gln Leu Gly Lys Leu
            275                 280                 285

Gln Ser Thr Tyr Ile Glu Gly Leu Leu Lys Val Val Arg Pro Asp Thr
            290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
            370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
            435                 440                 445

Pro Gly Val Lys Arg Tyr Met Glu Asn Ile Val Gln Glu Ala Lys Gln
            450                 455                 460

Lys Gly Tyr Val Thr Thr Leu Leu His Arg Arg Arg Tyr Leu Pro Asp
465                 470                 475                 480

Ile Thr Ser Arg Asn Phe Arg Val Arg Ser Phe Ala Arg Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
            515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575
```

Trp Tyr Asp Ala Lys
            580

<210> SEQ ID NO 80
<211> LENGTH: 581
<212> TYPE: PRT
<213> ORGANISM: Artificial Sequence
<220> FEATURE:
<223> OTHER INFORMATION: Synthetic

<400> SEQUENCE: 80

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu Met Tyr Arg Gln Leu Gly Lys Leu
        275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Lys Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Arg Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 81
<211> LENGTH: 581
<212> TYPE: PRT
<213> ORGANISM: Artificial Sequence
<220> FEATURE:
<223> OTHER INFORMATION: Synthetic

<400> SEQUENCE: 81

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Ala Lys Met Lys Gln Tyr Glu Ala Val Arg
        115                 120                 125

```
Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Lys Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
450                 455                 460

Lys Gly Tyr Val Thr Thr Leu Leu His Arg Arg Arg Tyr Leu Pro Asp
465                 470                 475                 480

Ile Thr Ser Arg Asn Phe Arg Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
```

```
                545                 550                 555                 560
Val Thr Leu Arg Val Pro Leu Lys Val Asp Tyr Arg Tyr Gly Ser Thr
                    565                 570                 575

Trp Tyr Asp Ala Lys
            580

<210> SEQ ID NO 82
<211> LENGTH: 581
<212> TYPE: PRT
<213> ORGANISM: Artificial Sequence
<220> FEATURE:
<223> OTHER INFORMATION: Synthetic

<400> SEQUENCE: 82

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu Arg Gly Arg
            35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu Met Tyr Arg Gln Leu Gly Lys Leu
        275                 280                 285

Gln Ser Thr Tyr Ile Glu Gly Leu Leu Lys Val Val Arg Pro Asp Thr
        290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
```

```
                    325                 330                 335
Glu Gly Arg Lys Ile Arg Gln Ala Phe Val Pro Ser Glu Ser Asp Trp
            340                 345                 350
Leu Ile Phe Ala Ala Asp Tyr Ser Gln Ile Glu Leu Arg Val Leu Ala
            355                 360                 365
His Ile Ala Glu Asp Asp Asn Leu Met Glu Ala Phe Arg Arg Asp Leu
            370                 375                 380
Asp Ile His Thr Lys Thr Ala Met Asp Ile Phe Gln Val Ser Glu Asp
385                 390                 395                 400
Glu Val Thr Pro Asn Met Arg Arg Gln Ala Lys Ala Val Asn Phe Gly
                405                 410                 415
Ile Val Tyr Gly Ile Ser Asp Tyr Gly Leu Ala Gln Asn Leu Asn Ile
                420                 425                 430
Ser Arg Lys Glu Ala Ala Glu Phe Ile Glu Arg Tyr Phe Gln Ser Phe
            435                 440                 445
Pro Gly Val Lys Arg Tyr Met Glu Asn Ile Val Gln Glu Ala Lys Gln
            450                 455                 460
Lys Gly Tyr Val Thr Thr Leu Leu His Arg Arg Arg Tyr Leu Pro Asp
465                 470                 475                 480
Ile Thr Ser Arg Asn Phe Arg Val Arg Ser Phe Ala Glu Arg Met Ala
                485                 490                 495
Met Asn Thr Pro Ile Gln Gly Ser Ala Ala Asp Ile Ile Lys Lys Ala
                500                 505                 510
Met Ile Asp Leu Asn Ala Arg Leu Lys Glu Glu Arg Leu Gln Ala His
            515                 520                 525
Leu Leu Leu Gln Val His Asp Glu Leu Ile Leu Glu Ala Pro Lys Glu
            530                 535                 540
Glu Met Glu Arg Leu Cys Arg Leu Val Pro Glu Val Met Glu Gln Ala
545                 550                 555                 560
Val Thr Leu Arg Val Pro Leu Lys Val Asp Tyr Arg Tyr Gly Ser Thr
                565                 570                 575
Trp Tyr Asp Ala Lys
            580

<210> SEQ ID NO 83
<211> LENGTH: 10
<212> TYPE: DNA
<213> ORGANISM: Artificial Sequence
<220> FEATURE:
<223> OTHER INFORMATION: Synthetic

<400> SEQUENCE: 83
acgagggggg                                                                10

<210> SEQ ID NO 84
<211> LENGTH: 6
<212> TYPE: DNA
<213> ORGANISM: Artificial Sequence
<220> FEATURE:
<223> OTHER INFORMATION: Synthetic

<400> SEQUENCE: 84 cccccc                                                                     6
```

THIOLATED NUCLEOTIDE ANALOGUES FOR NUCLEIC ACID SYNTHESIS

CROSS REFERENCE TO RELATED APPLICATIONS

This application claims priority to U.S. Provisional Application No. 62/078,323, filed on Nov. 11, 2014, which is incorporated by reference in its entirety herein.

SEQUENCE LISTING

This application hereby incorporates by reference the material of the electronic Sequence Listing filed concurrently herewith. The material in the electronic Sequence Listing is submitted as a text (.txt) file entitled "2015-11-09 LT00996_ST25.txt" created on Nov. 9 2015, which has a file size of 270 KB, and is herein incorporated by reference in its entirety.

BACKGROUND

The synthesis of nucleic acid polymers involves the enzyme-mediated incorporation of individual nucleotides to form and extend a nucleic acid polymer. Nucleotides that are typically used in this process are nucleoside polyphosphates, such as deoxyribonucleotide triphosphates (dNTPs) which can be incorporated in the synthesis of deoxyribonucleic acids (DNA), and ribonucleotide triphosphates (NTPs) which can be incorporated in the synthesis of ribonucleic acids (RNA). When incorporated, nucleotides undergo hydrolysis of one or more of its phosphodiester bonds, thus providing the thermodynamic driving force for the overall reaction. For example, extension of a DNA strand with a single dNTP can result in the DNA extended by the single nucleotide and the release of pyrophosphate (PPi).

SUMMARY

This application relates to sulfur-containing (i.e., thiolated) analogues of nucleotides that are useful for nucleic acid synthesis, and methods for using thiolated analogues of nucleotides.

In some embodiments, the present teachings provide systems, compositions, methods, reagents, kits and products for extending a nucleic acid that includes incorporating a nucleotide residue at a terminus of a nucleic acid using a polymerase enzyme and at least one nucleotide, wherein the at least one nucleotide includes a thiophosphate moiety, and wherein the at least one nucleotide is resistant to hydrolysis by phosphatase. In some embodiments, the incorporation of the nucleotide residue is template-directed. In some embodiments, the thiolated nucleotide is resistant to pyrophosphatase.

In some embodiments, the thiolated nucleotide is a deoxyribonucleotide. In some embodiments, the thiolated nucleotide is a deoxyribonucleotide thio-triphosphate. In some embodiments, the thiolated nucleotide is a deoxyribonucleotide-5'-γ[gamma]thio-triphosphate.

In some embodiments, the incorporation of the nucleotide residue is performed in the presence of a phosphatase. In some embodiments, the polyphosphate leaving group produced upon incorporation of the nucleotide residue in the extended nucleic acid is hydrolyzed. In some embodiments, the pyrophosphate leaving group is a thio-pyrophosphate. In some embodiments, the polyphosphate leaving group is a thio-triphosphate. In some embodiments, the polyphosphate leaving group is a thio-tetraphosphate.

In the some embodiments, the present teachings provide systems, compositions, methods, reagents, kits and products in which the specific rate of incorporation of the nucleotide with the thiophosphate moiety is at least 50%, at least 60%, at least 70%, at least 80%, at least 85%, at least 90%, at least 95%, at least 97.5%, or at least 99% of the specific rate of incorporation of the analogous nucleotide without the thiophosphate moiety. In some embodiments, the rate of incorporation is based on the rate of incorporation of the polymerase enzyme which is a Bst polymerase.

In the some embodiments, the present teachings provide systems, compositions, methods, reagents, kits and products in which the incorporation of the nucleotide residue is performed in the presence of at least one chelation moiety, wherein the chelation moiety is configured to bind an orthophosphate moiety. In some embodiments, the chelation moiety is configured to bind an orthophosphate moiety, wherein the orthophosphate moiety is a monobasic orthophosphate, a dibasic orthophosphate, a tribasic orthophosphate, a monobasic thiophosphate, a dibasic thiophosphate, or a tribasic thiophosphate.

In the some embodiments, the present teachings provide systems, compositions, methods, reagents, kits and products for identifying a base at a position in a target nucleic acid, including incorporating a nucleotide residue at a terminus of an extension primer that is hybridized to the target nucleic acid using a polymerase enzyme and at least one nucleotide, and identifying the position in a target nucleic acid based on the incorporation of the nucleotide residue, wherein the at least one nucleotide includes a thiophosphate moiety, and wherein the nucleotide is resistant to hydrolysis by phosphatase, wherein the nucleotide residue is incorporated when the nucleotide includes a base that is complementary to the corresponding position in the target nucleic acid.

In the some embodiments, the present teachings provide systems, compositions, methods, reagents, kits and products that include a composition that includes a polymerase enzyme, at least one nucleotide, wherein the nucleotide includes a thiophosphate moiety and is resistant to hydrolysis by phosphatase. In some embodiments, the composition includes a phosphatase, such as pyrophosphatase or alkaline phosphatase. In some embodiments, the composition includes a nucleic acid and an extension primer complementary to at least a portion of the nucleic acid. In some embodiments, the composition includes at least one chelation moiety, wherein the chelation moiety is configured to bind an orthophosphate moiety.

In the some embodiments, the present teachings provide systems, compositions, methods, reagents, kits and products that include a compound that includes a nucleotide that includes a thiophosphate moiety and which is resistant to hydrolysis by phosphatase. In some embodiments, the nucleotide is resistant to hydrolysis by pyrophosphatase. In some embodiments, the nucleotide is a deoxyribonucleotide. In some embodiments, the nucleotide is a deoxyribonucleotide thio-triphosphate. In some embodiments, the nucleotide is a deoxyribonucleotide-5'-γ[gamma]thio-triphosphate. In some embodiments, the polymerase-mediated specific rate of incorporation of the nucleotide with the thiophosphate moiety is at least 50%, at least 60%, at least 70%, at least 80%, at least 85%, at least 90%, at least 95%, at least 97.5%, or at least 99% of the polymerase-mediated specific rate of incorporation of the analogous nucleotide without the thiophosphate moiety. In some embodiments, the specific rate of incorporation of the nucleotide with the thiophosphate moiety is the same or greater than the specific rate of incorporation of the analogous nucleotide without the thiophosphate moiety. In some embodiments, the rate of incorporation is based on the polymerase enzyme which is a Bst polymerase.

The present disclosure provides methods, systems, compositions, reagents, kits and products for identifying a base at a position in a target nucleic acid, comprising: (a) incorporating a nucleotide at a terminus of an extension primer that is hybridized to the target nucleic acid using a polymerase enzyme and at least one nucleotide, wherein the terminal phosphate of the at least one nucleotide includes a thio-phosphate moiety, wherein the at least one nucleotide is resistant to hydrolysis by a phosphatase enzyme, and wherein the nucleotide incorporation produces a thio-pyrophosphate and a hydrogen ion or a proton; and (b) identifying the nucleotide that is incorporated at the terminus of the extension primer. In some embodiments, the at least one nucleotide is resistant to hydrolysis by a pyrophosphatase enzyme. In some embodiments, the nucleotide incorporating step is performed in the presence of a phosphatase enzyme and/or in the presence of a pyrophosphatase enzyme. In some embodiments, the at least one nucleotide comprises a deoxyribonucleotide-5'-γ[gamma]-thio-triphosphate. In some embodiments, the methods, systems, compositions, reagents, kits and products further comprises hydrolyzing the thio-pyrophosphate in the presence of the phosphatase, thereby producing an orthophosphate. In some embodiments, the methods, systems, compositions, reagents, kits and products further comprises identifying the nucleotide that is incorporated at the terminus of the extension primer by detecting the hydrogen ion or the proton. In some embodiments, the nucleotide incorporation step is conducted in the presence of at least one chelation moiety, wherein the chelation moiety is configured to bind the orthophosphate moiety. In some embodiments, the methods, systems, compositions, reagents, kits and products further comprises binding the at least one chelation moiety to the orthophosphate. In some embodiments, the orthophosphate is selected from a monobasic orthophosphate, a dibasic orthophosphate, a tribasic orthophosphate, a monobasic thiophosphate, a dibasic thiophosphate, and a tribasic thiophosphate. In some embodiments, the specific rate of incorporation of the nucleotide with the thiophosphate moiety is at least 95% of the specific rate of incorporation of the analogous nucleotide without the thiophosphate moiety. In some embodiments, the polymerase enzyme is a wild-type or mutant Bst polymerase enzyme. In some embodiments, the incorporating the nucleotide is conducted in a reaction chamber that is operatively coupled at least one ion sensor that detects hydrogen ions or protons. In some embodiments, the at least one ion sensor comprises and ISFET. In some embodiments, the incorporating the nucleotide in step (a) is conducted on an array of reaction chambers, wherein individual reaction chambers in the array are operatively coupled to at least one ion sensor that detects hydrogen ions or protons. In some embodiments, the individual reaction chambers in the array are operatively coupled to at least one ISFET.

DETAILED DESCRIPTION OF THE DRAWINGS

DESCRIPTION

The extension of nucleic acid polymers by the incorporation of individual nucleotides is a key feature of many processes in molecular biology, both in natural and artificial contexts. Examples of the latter which entail steps of nucleic acid extension include nucleic acid amplification, quantitative polymerase chain reaction, and nucleic acid sequencing. Nucleic acid extension involves the incorporation of a nucleotide residue by a polymerase into the nucleic acid that is being extended. This incorporation and extension is typically mediated by an enzyme, such as a nucleic acid polymerase, and uses an activated version of the nucleotide to be incorporated. An activated nucleotide typically includes one or more high-energy chemical bonds, at least one of which is broken and/or reformed as a lower energy bond, thus providing the free energy to drive the extension reaction. In certain embodiments, the activated chemical bond include, but are not limited to, phosphodiester bonds, phosphoramidite bonds, phosphothioester bonds, phosphoramine bonds, and the like.

A particular application of nucleic acid extension reactions is in the field of nucleic acid sequencing. In nearly all sequencing platforms, whether it be chemical degradation, chain-termination, sequence-by-synthesis, pyrosequencing, massively parallel, ion-sensitive, or single molecule platforms, the key step in determining the sequence of a target nucleic acid involves the extension of nucleic acid by incorporation of one or more nucleotides.

Figure 1:
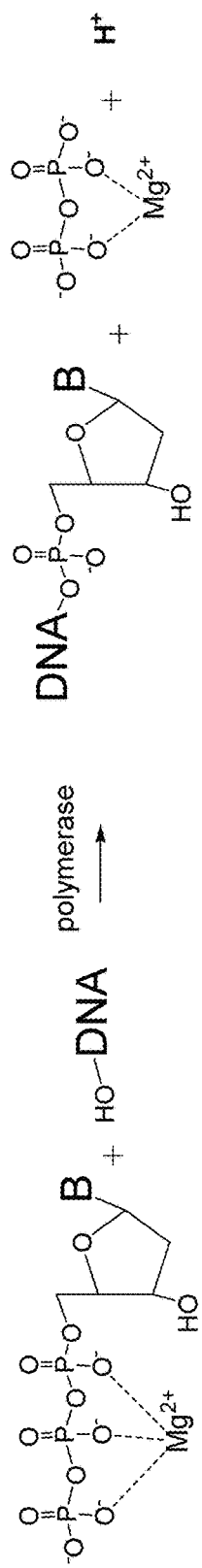
FIG. 1 depicts schematically an exemplary nucleotide extension reaction involving the incorporation of a nucleotide in the presence of an enzyme having nucleic acid polymerase activity.

As shown in FIG. 1, an exemplary polymerase-mediated nucleic acid extension reaction is shown. A nucleotide triphosphate in the presence of magnesium ion, polymerase enzyme, and the terminal end of a nucleic acid is incorporated at the terminus of the nucleic acid. The incorporation reaction typically results in a release of a pyrophosphate moiety and a hydrogen ion or proton. This reaction is a net exergonic reaction as a result of the free energy contribution by the hydrolysis of a phosphate diester bond.

As depicted in the schematic of the extension reaction, certain by-products are produced as a result of this extension reaction, specifically an equivalent each of hydrogen ion and pyrophosphate. In certain embodiments, one or more of the products of the reaction can be used to detect or measure the extension reaction. For example, as described herein, ion-based nucleic acid sequencing methods and platforms include the Ion Torrent PGM™ or Proton™ sequencer (Ion Torrent™ Systems, Life Technologies Corporation) the released hydrogen ion can result in a pH change in the reaction environment, which can be detected by an ion sensor. In certain embodiments, the extension reaction is performed in a microwell, to which the ion sensor is coupled. Advantages of performing the extension reaction in a defined space such as a microwell include the ability to control the influx and efflux of reagents and by-products. Another advantage is the ability to perform a multiplicity of extension reaction equivalents in the same defined space, which can produce a corresponding increase in equivalents of reaction products. Particularly if the multiple extension reactions are extensions of a homogenous population of template nucleic acids, such as would be performed in a sequencing reaction, the multiple parallel reactions will additively produce a larger signal to be detected and measured.

One manner in which sequencing technology continuously advances is miniaturization. For example, by decreasing the physical footprint in which the nucleic acid extension reactions occurs, such as by decreasing the size and/or volume of the microwell containing the extension reaction, one can increase the number of reactions that can be performed within a given space or area on a platform or substrate. However, one disadvantage that can arise from reducing the size in this manner is that the quantity of extension reactions (e.g. the absolute number of extension reactions) in each microwell can be reduced. In embodiments in which detection or measurement of the extension reaction is based on detection or measurement of one or more by-products of the reaction, then this reduction can result in a decreased total signal to measure the progress of the extension reactions.

A further effect of this reduced signal can be a reduction in the effective read-length of each sequencing reaction. In embodiments in which each reaction involves sequential extension reaction, the efficiency and yield of each extension can decrease with each nucleotide that is incorporated. As a result of the decreased efficiency, in conjunction with the decreased signal due to the reduced amount of the reaction, the effective read-length measured in each well can also be reduced.

Figure 2:
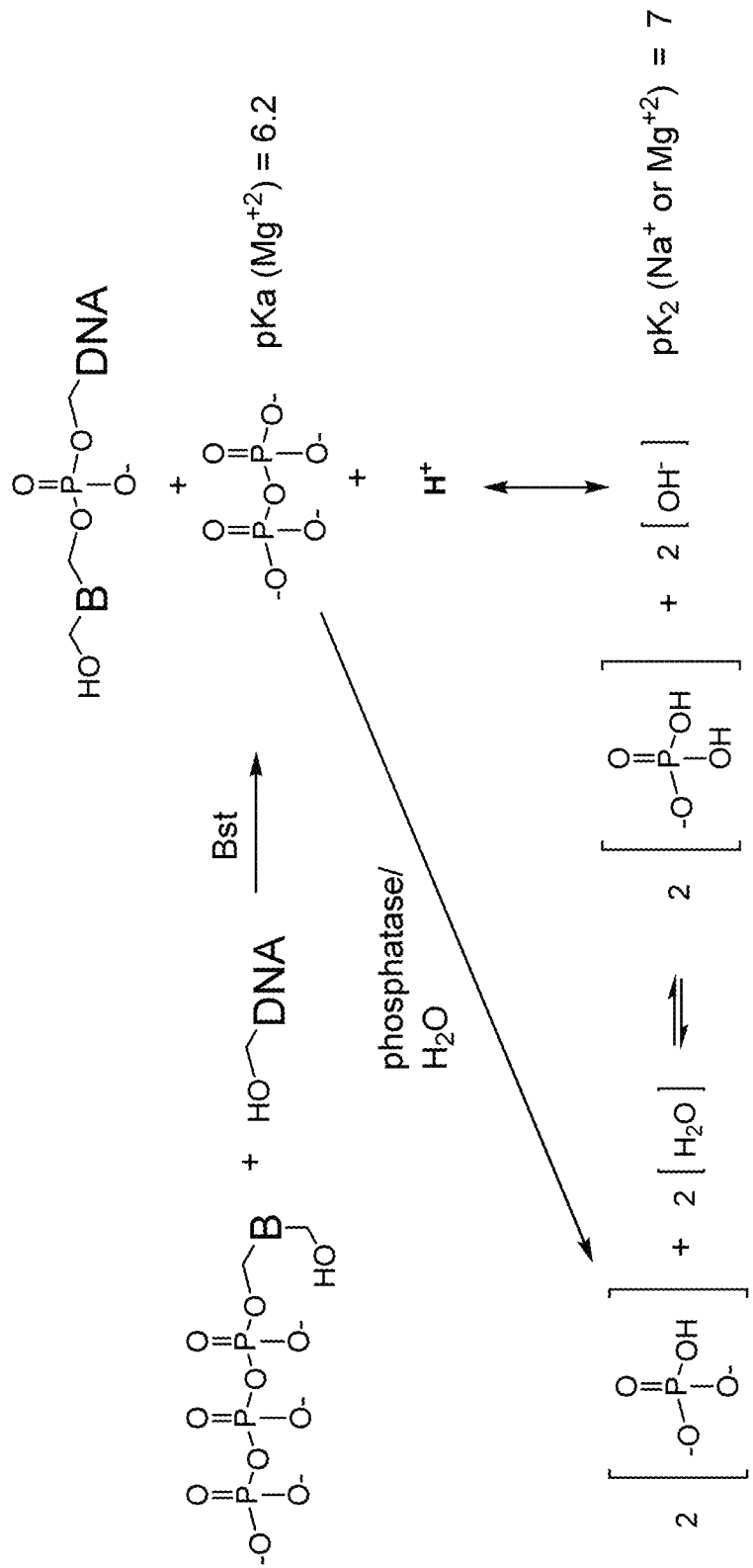
FIG. 2 depicts schematically an exemplary nucleotide extension reaction involving the incorporation of a nucleotide in the presence of an enzyme having nucleic acid polymerase activity and an enzyme having phosphatase activity.

Thus, one strategy to counter this decrease in total efficiency resulting from a decreased number of reactions is to increase the efficiency of the extension reactions. In some embodiments, such as the extension reaction shown in FIG. 1, the schematically-depicted extension reaction results in a hydrogen ion and pyrophosphate as by-products. However, this extension reaction can be driven further exergonically by hydrolysis of a second high-energy diester bond in the pyrophosphate by-product, thereby increasing the net favorable free energy, and hence the efficiency, of each nucleotide incorporation. An exemplary embodiment of this reaction is shown in FIG. 2. As shown in this exemplary schematic reaction, the nucleotide incorporation reaction shown in FIG. 1 is performed in the presence of an additional enzyme having phosphatase and/or pyrophosphatase activity, which results in the hydrolysis of a second phosphodiester bond. This second hydrolysis increases the net free energy of the reaction and can result in an increased yield and efficiency of the first nucleotide incorporation step.

Although the exemplary reaction depicted in FIG. 2 can result in an extension reaction having a higher efficiency of the overall nucleotide incorporation reaction, in certain contexts and embodiments this approach can have certain disadvantages. For example, sequencing methods that measure or detect the hydrogen ion by-product can be hindered by the additional hydrolysis step as the orthophosphates produced as by-products in this reaction can act as conjugate bases, thus neutralizing any net production of hydrogen ions.

The schematic exemplary reaction of FIG. 2 also has other potential disadvantages in certain embodiments and contexts. For example, although the hydrolysis by the phosphatase and/or pyrophosphatase activity can increase the efficiency of the reaction as described above, the nucleotide polyphosphate starting reagent, such as the commonly used nucleotide triphosphates (dNTPs or NTPs), can also be susceptible to hydrolysis by the same phosphatase and/or pyrophosphatase activity. Thus, without isolating the nucleotide polyphosphates from the subsequent phosphatase and/or pyrophosphatase activity, or modifying the nucleotide polyphosphate to render it resistant to said activity, the reaction as shown may not be able to be performed in a single reaction environment with all reagents and enzymes present simultaneously. Moreover, attempts to mitigate this problem by modification of the nucleotide polyphosphate to render it resistant to phosphatase and/or pyrophosphatase activity, such as by the addition of a protecting group, can also result in a nucleotide that may be a poorer substrate for the polymerase enzyme.

In certain embodiments, the present disclosure relates to compounds, compositions, methods, systems, apparatus and kits that include a nucleotide that includes at least one thiophosphate moiety. In certain embodiments, a thiophosphate moiety includes a molecular substructure having the formula of $PS_{4-x}O_x^{3-}$. In certain embodiments, a thiophosphate moiety includes a molecular substructure having the formula of $PSO_3^{3-}$, $PS_2O_2^{3-}$, $PS_3O^{3-}$, $PS_3O^{3-}$, or phosphate-based derivatives of any of the foregoing, including phosphoesters, phosphodiesters, phosphotriesters, phosphoamides, or phosphodiamides. In some embodiments, the thiophosphate can include or be substituted with any one or more of the following, or any suitable combination thereof: one or more alkyl groups, one or more cycloalkyl groups, one or more aryl groups, one or more heteroaryl groups, one or more halogen groups, one or more amino groups, one or more alkylamino groups, one or more dialkylamino groups, one or more mercapto or thio groups, one or more alkylthio groups, or one or more cyclic derivatives of the foregoing (e.g., cycloalkyl groups), or any suitable combination thereof.

In certain embodiments, the thiolated nucleotide having a thiophosphate moiety is a nucleoside polyphosphate, such as a nucleotide diphosphate, a nucleoside triphosphate, a nucleoside tetraphosphate, a nucleoside pentaphosphate, or nucleotides having 6, 7, 8, 9 10 or more phosphates, or higher-order polyphosphates, in which one or more of the phosphate moieties is a thiophosphate moiety. In certain embodiments, the sulfur of the thiophosphate moiety is connected only to the phosphate and optionally a hydrogen. In certain embodiments, the sulfur of the thiophosphate moiety bridges two phosphate centers.

In certain embodiments, the sulfur is bonded to the phosphate most proximate to the nucleoside, thus forming part of the α (alpha)-thiophosphate of the nucleoside polyphosphate. In certain embodiments, the sulfur is bonded to the phosphate that is second-most proximate to the nucleoside, thus forming part of the β (beta)-thiophosphate of the nucleoside polyphosphate. In certain embodiments, the sulfur is bonded to the phosphate that is third-most proximate to the nucleoside, thus forming part of the γ (gamma)-thiophosphate of the nucleoside polyphosphate. In certain embodiments, the sulfur is bonded to the phosphate that is fourth-most proximate to the nucleoside, thus forming part of the δ (delta)-thiophosphate of the nucleoside polyphosphate. In certain embodiments, the sulfur is bonded to the phosphate that is fifth-most proximate to the nucleoside, thus forming part of the ε (epsilon)-thiophosphate of the nucleoside. polyphosphate.

In certain embodiments, the sulfur is bonded to the phosphate that is the terminal phosphate of the nucleoside polyphosphate.

Figure 3:
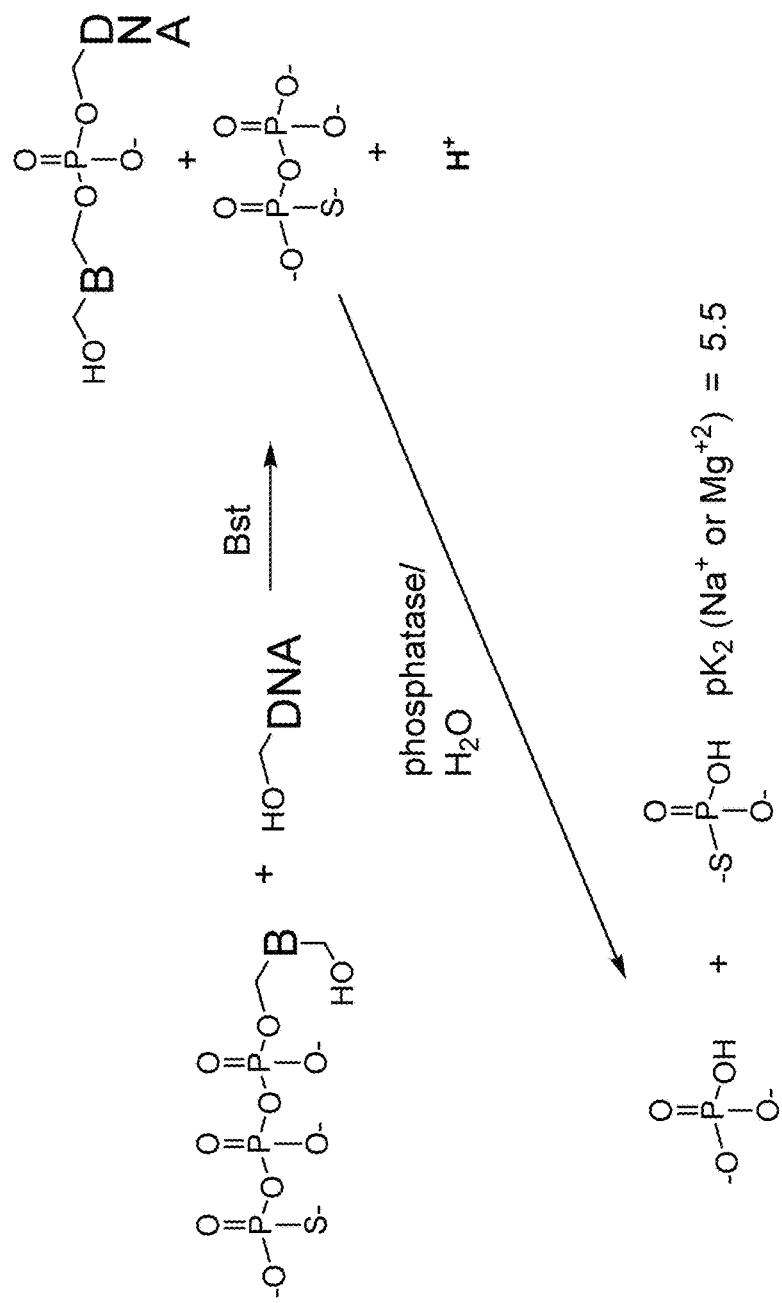
FIG. 3 depicts schematically an exemplary nucleotide extension reaction involving the incorporation of a nucleotide with a thiophosphate moiety in the presence of an enzyme having nucleic acid polymerase activity and an enzyme having phosphatase activity.

In certain embodiments, the sulfur is bonded to the phosphate that is third-most proximate to the nucleoside, thus forming part of the γ (gamma)-thiophosphate of the nucleoside polyphosphate, and which is also the terminal phosphate of the nucleoside thiophosphate. An example of this species is depicted in FIG. 3 in the form of a nucleoside γ (gamma)-thiophosphate Without intending to be bound by theory, the thiolated nucleotides of the present disclosure are resistant to hydrolysis by enzymes having phosphatase and/or pyrophosphatase activity. In certain embodiments, thiolated nucleotides in which the sulfur is bonded to the terminal polyphosphate of a nucleoside polyphosphate are resistant to phosphatase or pyrophosphatase activity.

Figure 4:
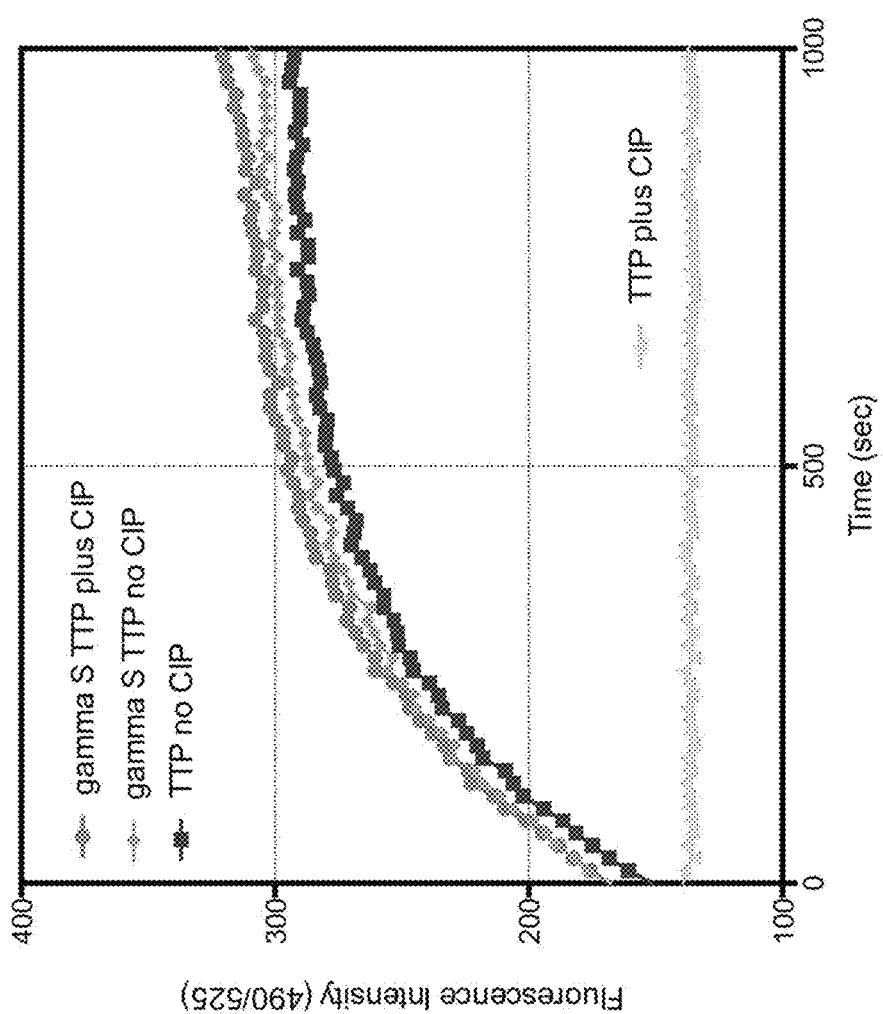
FIG. 4 depicts an exemplary phosphatase resistance assay of nucleotide triphosphate and nucleotide gamma-S-triphosphate.

As an example of this resistant, representative results from an exemplary experiment are depicted in FIG. 4. This figure shows the normalized fluorescence intensity over time of two different nucleoside polyphosphates, γ-S-thymidinyl-triphosphate ("gamma S TTP") and thymidinyl-triphosphate ("TTP") in the presence or absence of calf intestinal alkaline phosphatase ("CIP"). Phosphatase-mediated hydrolysis is reflected as a non-increasing level of fluorescence, whereas phosphatase resistance is reflected as an increase in normalized fluorescence intensity. Therefore, as depicted in this exemplary experiment, the thiolated nucleotide showed a resistance to phosphatase that was not reflected in the analogous non-thiolated nucleotide, TTP.

In certain embodiments, the thiolated nucleotides of the present disclosure are incorporated in nucleic acid extension reactions by polymerase enzymes at the same or substantially the same rate and/or affinity. In some embodiments, the polymerase-mediated specific rate of incorporation of the nucleotide with the thiophosphate moiety is at least 50%, at least 60%, at least 70%, at least 80%, at least 85%, at least 90%, at least 95%, at least 97.5%, or at least 99% of the polymerase-mediated specific rate of incorporation of the analogous nucleotide without the thiophosphate moiety. In some embodiments, the specific rate of incorporation of the nucleotide with the thiophosphate moiety is the same or greater than the specific rate of incorporation of the analogous nucleotide without the thiophosphate moiety. In some embodiments, the rate of incorporation is based on the polymerase enzyme which is a Bst polymerase. Without intending to be bound by theory, thiolated nucleotides of the present disclosure are incorporated at the same or substantially the same rate as their non-thiolated counterpart because the substitution of an oxygen atom for a sulfur atom is relatively non-disruptive with respect to steric and polarity properties. Moreover, the thiolated nucleotides in which the sulfur is present at the terminal (e.g., gamma) position of the polyphosphate would mean that this substitution is the most distal from the alpha-phosphate where the incorporation reaction is concerned.

In some embodiments, the present teachings provide systems, compositions, methods, reagents, kits and products for extending a nucleic acid that includes incorporating a nucleotide residue at a terminus of a nucleic acid using a polymerase enzyme and at least one nucleotide, wherein the at least one nucleotide includes a thiophosphate moiety, and wherein the at least one nucleotide is resistant to hydrolysis by phosphatase. In some embodiments, the incorporation of the nucleotide residue is template-directed. In some embodiments, the thiolated nucleotide is resistant to pyrophosphatase.

In some embodiments, the thiolated nucleotide is a deoxyribonucleotide. In some embodiments, the thiolated nucleotide is a deoxyribonucleotide thio-triphosphate. In some embodiments, the thiolated nucleotide is a deoxyribonucleotide-5'-γ[gamma]thio-triphosphate.

In some embodiments, the incorporation of the nucleotide residue is performed in the presence of a phosphatase. In some embodiments, the polyphosphate leaving group produced upon incorporation of the nucleotide residue in the extended nucleic acid is hydrolyzed. In some embodiments, the pyrophosphate leaving group is a thio-pyrophosphate.

In the some embodiments, the present teachings provide systems, compositions, methods, reagents, kits and products in which the specific rate of incorporation of the nucleotide with the thiophosphate moiety is at least 50%, at least 60%, at least 70%, at least 80%, at least 85%, at least 90%, at least 95%, at least 97.5%, or at least 99% of the specific rate of incorporation of the analogous nucleotide without the thiophosphate moiety. In some embodiments, the rate of incorporation is based on the rate of incorporation of the polymerase enzyme which is a Bst polymerase.

In the some embodiments, the present teachings provide systems, compositions, methods, reagents, kits and products in which the incorporation of the nucleotide residue is performed in the presence of at least one chelation moiety, wherein the chelation moiety is configured to bind an orthophosphate moiety. In some embodiments, the chelation moiety is configured to bind preferentially to an orthophosphate moiety compared to a pyrophosphate or thiopyrophosphate moiety. In some embodiments, the chelation moiety is configured to bind an orthophosphate moiety, wherein the orthophosphate moiety is a monobasic orthophosphate, a dibasic orthophosphate, a tribasic orthophosphate, a monobasic thiophosphate, a dibasic thiophosphate, or a tribasic thiophosphate.

In the some embodiments, the present teachings provide systems, compositions, methods, reagents, kits and products for identifying a base at a position in a target nucleic acid, including incorporating a nucleotide residue at a terminus of an extension primer that is hybridized to the target nucleic acid using a polymerase enzyme and at least one nucleotide, and identifying the position in a target nucleic acid based on the incorporation of the nucleotide residue, wherein the at least one nucleotide includes a thiophosphate moiety, and wherein the nucleotide is resistant to hydrolysis by phosphatase, wherein the nucleotide residue is incorporated when the nucleotide includes a base that is complementary to the corresponding position in the target nucleic acid.

In the some embodiments, the present teachings provide systems, compositions, methods, reagents, kits and products that include a composition that includes a polymerase enzyme, at least one nucleotide, wherein the nucleotide includes a thiophosphate moiety and is resistant to hydrolysis by phosphatase. In some embodiments, the composition includes a phosphatase, such as pyrophosphatase. In some embodiments, the composition includes a nucleic acid and an extension primer complementary to at least a portion of the nucleic acid. In some embodiments, the composition includes at least one chelation moiety, wherein the chelation moiety is configured to bind an orthophosphate moiety.

In the some embodiments, the present teachings provide systems, compositions, methods, reagents, kits and products that include a compound that includes a nucleotide that includes a thiophosphate moiety and which is resistant to hydrolysis by phosphatase. In some embodiments, the nucleotide is resistant to hydrolysis by pyrophosphatase. In some embodiments, the nucleotide is a deoxyribonucleotide.

In some embodiments, the nucleotide is a deoxyribonucleotide thio-triphosphate. In some embodiments, the nucleotide is a deoxyribonucleotide-5'-γ[gamma]thio-triphosphate. In some embodiments, the polymerase-mediated specific rate of incorporation of the nucleotide with the thiophosphate moiety is at least 50%, at least 60%, at least 70%, at least 80%, at least 85%, at least 90%, at least 95%, at least 97.5%, or at least 99% of the polymerase-mediated specific rate of incorporation of the analogous nucleotide without the thiophosphate moiety. In some embodiments, the specific rate of incorporation of the nucleotide with the thiophosphate moiety is the same or greater than the specific rate of incorporation of the analogous nucleotide without the thiophosphate moiety. In some embodiments, the rate of incorporation is based on the polymerase enzyme which is a Bst polymerase In certain embodiments, the present description relates to other improvements to enhance the efficiency of the nucleotide incorporation reactions used in, for example, nucleic acid extension reactions used in nucleic acid sequencing analysis as described herein. In certain embodiments, such improvements can be used independently or in conjunction with other improved described herein or known in the art.

As discussed herein, the efficiency of a nucleotide incorporation reaction, such as when used as part of a nucleic acid extension reaction, can be enhanced by removing by-products of the reaction, such as by hydrolysis of the pyrophosphate or thiopyrophosphate by-products. In this manner, the net favorable energetics of the overall reaction are increased by the additional hydrolysis step. Another analogous approach is to sequester or otherwise remove one or more by-products of the reaction. Without intending to be bound by theory, sequestration of by-products may improve the overall reaction efficiency by shifting the equilibrium of the reaction towards completion by decreasing the concentration of the sequestered by-products. Moreover, sequestration of one or more by-products can also prevent or limit the participation of the by-product in side-reactions that would otherwise diminish the detection or measurement of other by products. For example, as described herein, certain sequencing technologies rely on detection or measurement of the hydrogen ions generated during the nucleic acid extension reaction. However, as described herein, the generation of orthophosphate or thiophosphate moieties, particularly those having basic equivalents, may absorb the hydrogen ions produced during the reaction. Without intending to be bound by theory, by sequestering orthophosphate or thiophosphate moieties, particularly when such moieties are in their basic forms, can limit or prevent their neutralization of the hydrogen ions by their basic phosphate or thiophosphate equivalents.

Figure 5:
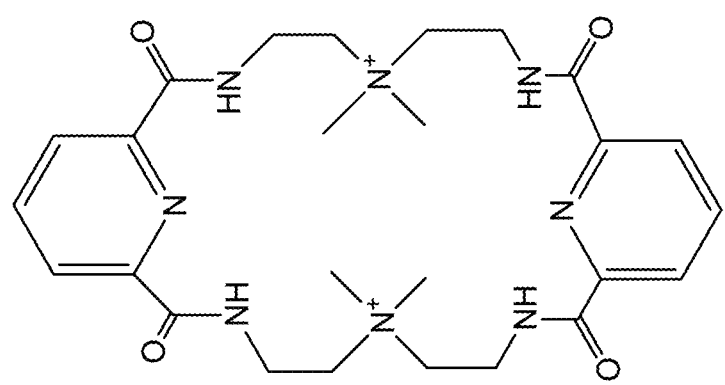
FIG. 5 depicts schematically an exemplary phosphate complexing agent.

As an example of these embodiments, the present disclosure includes the use of one or more complexing moieties that is configured to bind a phosphate moiety, a thiophosphate moiety, or analogues thereof. For example, as depicted in FIG. 5, an exemplary complexing molecule that is capable of binding a phosphate or thiophosphate moiety.

In certain embodiments, complexing agents of the present disclosure have preferred affinities for monobasic, dibasic, or tribasic orthophosphate. In certain preferred embodiments, complexing agents have preferred affinities for tribasic orthophosphate ($PO_4^{3-}$), which may release the highest number of equivalents of hydrogen ions.

In certain embodiments, complexing agents of the present disclosure have preferred affinities for monobasic, dibasic, or tribasic thiophosphate. In certain preferred embodiments, complexing agents have preferred affinities for tribasic orthophosphate ($PSO_3^{3-}$), which may release the highest number of equivalents of hydrogen ions.

In certain embodiments, complexing agents of the present disclosure are able to bind their preferred orthophosphate or thiophosphate species at a pH at which the nucleotide extension reaction is performed. In this manner, the sequestration of the phosphate or thiophosphate species can occur in substantially real-time with the generation of the phosphate or thiophosphate from the reaction.

In certain embodiments, complexing agents of the present disclosure have a low affinity for the nucleoside polyphosphate or nucleoside thiolated polyphosphate, or a lower affinity for the nucleoside polyphosphate or nucleoside thiolated polyphosphate as compared to orthophosphate or thiophosphate.

A nucleotide comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. A nucleotide polymerization reaction (also called a "nucleotide incorporation" reaction) can include primer extension reactions, nucleic acid amplification reactions, or sequence-by-synthesis reactions. Nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In some embodiments, one or more phosphorus atoms in the chain can be part of a phosphate group having P and O. In some embodiments, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In some embodiments, the phosphorus atoms in the chain can have at least one side group including O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleosides, analogs, derivatives, or variants of the foregoing compounds. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

In some embodiments, a nucleotide can include a purine or pyrimidine base, including adenine, guanine, cytosine, thymine or uracil. In some embodiments, a nucleotide includes dATP, dGTP, dCTP, dTTP and dUTP.

In some embodiments, the nucleotide is unlabeled. In some embodiments, the nucleotide comprises a label and referred to herein as a "labeled nucleotide". In some embodiments, the label can be attached to any portion of a nucleotide including a base, sugar or any intervening phosphate group or a terminal phosphate group, i.e., the phosphate group most distal from the sugar.

In some embodiments, a nucleotide (or analog thereof) can be attached to a label. In some embodiments, a label comprises a detectable moiety. In some embodiments, a label can generate, or cause to generate, a detectable signal. A detectable signal can be generated from a chemical or physical change (e.g., heat, light, electrical, pH, salt concentration, enzymatic activity, or proximity events). For example, a proximity event can include two reporter moieties approaching each other, or associating with each other, or binding each other. A detectable signal can be detected optically, electrically, chemically, enzymatically, thermally, or via mass spectroscopy or Raman spectroscopy. A label can include compounds that are luminescent, photoluminescent, electroluminescent, bioluminescent, chemiluminescent, fluorescent, phosphorescent or electrochemical. A label can include compounds that are fluorophores, chromophores, radioisotopes, haptens, affinity tags, atoms or enzymes. In some embodiments, the label comprises a moiety not typically present in naturally occurring nucleotides. For example, the label can include fluorescent, luminescent or radioactive moieties.

By way of a non-limiting example of nucleotide incorporation (e.g., DNA polymerization), the steps or events of nucleotide incorporation are well known and generally comprise: (1) complementary base-pairing a template DNA molecule with a DNA primer molecule having a terminal 3' OH (the terminal 3' OH provides the polymerization initiation site for DNA polymerase); (2) binding the base-paired template/primer duplex with a DNA-dependent polymerase to form a complex; (3) a candidate nucleotide binds with the DNA polymerase which interrogates the candidate nucleotide for complementarity with the template nucleotide on the template DNA molecule; (4) the DNA polymerase may undergo a conformational change (e.g., from an open to a closed complex if the candidate nucleotide is complementary); (5) the polymerase catalyzes nucleotide incorporation.

In one embodiment, the polymerase catalyzes nucleotide incorporation by forming a bond between the candidate nucleotide and the nucleotide at the terminal end of the polymerization initiation site. The polymerase can catalyze the terminal 3' OH of the primer exerting a nucleophilic attack on the bond between the α and β phosphates of the candidate nucleotide to mediate a nucleotidyl transferase reaction resulting in phosphodiester bond formation between the terminal 3' end of the primer and the candidate nucleotide (i.e., nucleotide incorporation in a template-dependent manner), and concomitant cleavage to form a cleavage product. The polymerase can liberate the cleavage product. In some embodiments, where the polymerase incorporates a nucleotide having phosphate groups, the cleavage product includes one or more phosphate groups. In some embodiments, where the polymerase incorporates a nucleotide having substituted phosphate groups, the cleavage product may include one or more substituted phosphate groups. In some embodiments, nucleotide incorporation reactions produce one or more cleavage products (e.g., byproducts) including polyphosphate compounds (pyrophosphates), hydrogen ions, or protons.

The candidate nucleotide may or may not be complementary to the template nucleotide on the template molecule. The candidate nucleotide can bind the polymerase and then dissociate from the polymerase. If the nucleotide dissociates from the polymerase (e.g., it is not incorporated), it can be liberated and typically carries intact polyphosphate groups.

In some embodiments, nucleotide incorporation can be a reverse transcriptase reaction which includes a nucleic acid template (RNA or DNA), primers, nucleotides (or analogs thereof) and reverse transcriptase enzyme. In some embodiments, nucleotide incorporation can be a transcription reaction which includes an RNA template, nucleotides (or analogs thereof) and a DNA-dependent RNA polymerase enzyme. Nucleotide incorporation events involving reverse transcriptase or DNA-dependent RNA polymerase are well known in the art.

In some embodiments, a nucleotide incorporation reaction can include natural nucleotides, nucleotide analogs, or a combination of both.

A polymerase comprises any enzyme that can catalyze the polymerization of nucleotides (including analogs thereof) into a nucleic acid strand. Typically but not necessarily such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. In some embodiments, a polymerase can be a high fidelity polymerase. Typically, the polymerase comprises one or more active sites at which nucleotide binding and/or catalysis of nucleotide polymerization can occur. In some embodiments, a polymerase includes or lacks other enzymatic activities, such as for example, 3' to 5' exonuclease activity, 5' to 3' exonuclease activity, or strand displacement activity. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof.

In some embodiments, the polymerase can include any one or more polymerases, or biologically active fragment of a polymerase, which are described in any of: U.S. published application No. 2011/0262903, published Oct. 27, 2011;

International PCT Publication No. WO 2013/023176, published Feb. 14, 2013; International PCT Publication No. WO 2013/023176, published Feb. 14, 2013; U.S. 61/884,921, filed Sep. 30, 2013; U.S. published application No. 2011/0262903, published Oct. 27, 2011; U.S. published application No. 2011/0301041, published Dec. 8, 2011; U.S. published application No. 2012/0202276; U.S. Ser. No. 13/035,177, filed Feb. 25, 2011, and published as U.S. published application No. 2011/0318748 on Dec. 29, 2011; U.S. Ser. No. 13/572,488, filed Aug. 10, 2012; and U.S. 61/884,921, filed Sep. 30, 2013.

In some embodiments, a polymerase can be a DNA polymerase and include without limitation bacterial DNA polymerases, eukaryotic DNA polymerases, archaeal DNA polymerases, viral DNA polymerases and phage DNA polymerases.

In some embodiments, a polymerase can be a replicase, DNA-dependent polymerase, primases, RNA-dependent polymerase (including RNA-dependent DNA polymerases such as, for example, reverse transcriptases), a thermo-labile polymerase, or a thermo-stable polymerase. In some embodiments, a polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440. In some embodiments, a polymerase can be a T3, T5, T7, or SP6 RNA polymerase.

In some embodiments, nucleotide incorporation reactions can be conducted with one type or a mixture of different types of polymerases. In some embodiments, nucleotide incorporation reactions can be conducted with a low fidelity or high fidelity polymerase.

In some embodiments, an archaeal DNA polymerase can be, without limitation, an A family DNA polymerase; a B family DNA polymerase; a mixed-type polymerase; an unclassified DNA polymerase and RT family polymerase; and variants and derivatives thereof.

In some embodiments, nucleic acid amplification reactions can be catalyzed by heat-stable or heat-labile polymerases.

In some embodiments, an archaeal DNA polymerase can be, without limitation, a thermostable or thermophilic DNA polymerase such as, for example: a *Bacillus subtilis* (Bsu) DNA polymerase I large fragment; a *Thermus aquaticus* (Taq) DNA polymerase; a *Thermus filiformis* (Tfi) DNA polymerase; a Phi29 DNA polymerase; a *Bacillus stearothermophilus* (Bst) DNA polymerase; a *Thermococcus* sp. 9° N-7 DNA polymerase; a *Bacillus smithii* (Bsm) DNA polymerase large fragment; a *Thermococcus litoralis* (Tli) DNA polymerase or Vent™ (exo-) DNA polymerase (from New England Biolabs); or "Deep Vent" (exo-) DNA polymerase (New England Biolabs).

In some embodiments, the DNA polymerase is an A family DNA polymerase selected from the group consisting of a Pol I-type DNA polymerase such as *E. coli* DNA polymerase, the Klenow fragment of *E. coli* DNA polymerase, Bst DNA polymerase, Taq DNA polymerase, Platinum Taq DNA polymerase series, T7 DNA polymerase, and Tth DNA polymerase. In some embodiments, the DNA polymerase is Bst DNA polymerase. In other embodiments, the DNA polymerase is *E. coli* DNA polymerase. In some embodiments, the DNA polymerase is the Klenow fragment of *E. coli* DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfutubo polymerase, Pyrobest polymerase, Pwo polymerase, KOD polymerase, Sac polymerase, Sso polymerase, Poc polymerase, Pab polymerase, Mth polymerase, Pho polymerase, ES4 polymerase, VENT polymerase, DEEPVENT polymerase, phage Phi29 polymerase, and phage B103 polymerase. In some embodiments, the polymerase is phage Phi29 DNA polymerase. In some embodiments the polymerase is phage B103 polymerase, including, for example, the variants disclosed in U.S. Patent Publication No. 2011/0014612.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

In some embodiments, the disclosure relates generally to methods, as well as related, systems, compositions, kits and apparatuses for incorporating one or more nucleotides (e.g., nucleotide analogs), comprising: providing a template nucleic acid hybridized to a primer and bound to a polymerase; synthesizing a new nucleic acid strand by incorporating one or more nucleosides (e.g., any of the nucleotide analogs described in the present teachings) sequentially at the 3' end of the primer; and detecting such incorporation at the 3' end of the primer. The incorporation nucleotide can be detected by measuring a concentration of a hydrogen ion byproduct generated if the incorporated nucleoside is complementary to the corresponding nucleotides in the template nucleic acid.

In some embodiments, the polymerase can include any one or more of the amino acid substitutions described herein. In some embodiments, at least one of the one or more amino acid substitutions can be a conservative amino acid substitution. In some embodiments, each of the one or more amino acid substitutions is a conservative amino acid substitution.

In some embodiments, the polymerase includes any one of the modified polymerases described herein. In some embodiments, the polymerase is a bufferless polymerase. For example, the polymerase can have reduced buffering capacity relative to the corresponding unsubstituted polymerase.

In some embodiments, the polymerase includes one or more amino acid substitutions that substantially remove the buffering capacity of the polymerase within the pH range of about 4 to about 10 relative to the corresponding unsubstituted polymerase. The unsubstituted polymerase can be the wild-type version of the polymerase.

In some embodiments, the one or more amino acid substitutions in the polymerase substantially remove the buffering capacity of the polymerase relative to the corresponding unsubstituted polymerase within the range of about pH 7 to about pH 9. The unsubstituted polymerase can be the wild-type version of the polymerase.

In some embodiments, at least one of the one or more amino acid substitutions in the polymerase is a conservative amino acid substitution that is selected from the group consisting of histidine to arginine, glutamic acid to glutamine, aspartic acid to asparagine, lysine to arginine, and tyrosine to phenylalanine.

In some embodiments, at least one of the one or more amino acid substitutions includes a substitution of an amino acid residue having a pKa within the range of about 4.0 to about 10.0 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more amino acid substitutions includes a substitution of an amino acid residue having a pKa within the range of about 7 to about 9 with another amino acid residue. In some embodiments, the pKa of the amino acid residue is a solution pKa of the amino acid residue. In other embodiments, the pKa of the amino acid residue is a pKa of the amino acid residue in the context of the corresponding wild-type protein.

In some embodiments, at least one of the one or more conservative amino substitutions includes a substitution of an amino acid residue having a pKa of between about 4.0 and about 10.0 with an amino acid residue having a pKa that is greater than about 10.0 or less than about 4.0. In further embodiments the amino acid residue having a pKa that is greater than about 10.0 or less than about 4.0 is selected from the group consisting of: Arg, Asp, Gln, Lys, Ile, Leu, Norleucine (Nle), Met, Phe, Ser, Thr, Trp, Val and N-terminal Formylmethionine (N-fMet).

In some embodiments, at least one of the one or more conservative amino substitutions includes a substitution of an amino acid residue having a pKa of between about 7 and about 9 with an amino acid residue having a pKa that is greater than about 9 or less than about 7. In further embodiments the amino acid residue having a pKa that is greater than about 9 or less than about 7 is selected from the group consisting of: Arg, Asp, Gln, ly, Ile, Leu, Norleucine (Nle), Met, Phe, Ser, Thr, Trp, Val and N-terminal Formylmethionine (N-fMet).

In some embodiments, at least one of the one or more amino acid substitutions includes a substitution of an amino acid residue having a pKa within the range of about 6.0 to about 8.0 with another amino acid residue.

In some embodiments, at least one of the one or more amino acid substitutions includes a substitution of an amino acid residue having a pKa of between about 6.0 and about 8.0 with an amino acid residue having a pKa that is greater than about 8.0 or less than about 6.0.

In some embodiments, at least one of the one or more amino acid substitutions includes a substitution of an amino acid residue having a pKa within the range of about 7.0 to about 9.0 with another amino acid residue.

In some embodiments, at least one of the one or more amino acid substitutions includes a substitution of an amino acid residue having a pKa of between about 7.0 and about 9.0 with an amino acid residue having a pKa that is greater than about 9.0 or less than about 7.0.

In some embodiments, at least one of the one or more amino acid substitutions includes a substitution of an amino acid residue selected from the group consisting of His, Glu, Asp, Tyr, and Lys with another amino acid residue.

In some embodiments, at least one of the one or more amino acid substitutions is a substitution of an amino acid residue with an alanine residue.

In some embodiments, the polymerase comprises one or more conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, at least one of the one or more amino acid substitutions is a substitution of an amino acid residue with an alanine residue.

In some embodiments, the polymerase comprises one or more amino acid conservative amino acid substitutions that reduce the buffering capacity of the protein relative to the corresponding wild-type protein within the range of about pH 4 to about pH 10, about pH 5.5 to about pH 9.5, or about pH 7 to about pH 9. In some embodiments, at least one of the one or more amino acid substitutions includes a substitution of an amino acid residue that is at least 20%, at least 25%, at least 30%, at least 35% or at least 40% solvent exposed in the corresponding wild-type protein with another amino acid residue.

In some embodiments, the polymerase comprises one or more conservative amino acid substitutions that substantially remove the buffering capacity of the polymerase within the range of about pH 4 to about pH 10, about pH 5.5 to about pH 9.5, or about pH 7 to about pH 9.

In some embodiments, the DNA polymerase is a Bst DNA polymerase comprising one or more amino acid substitutions that substantially reduce its buffering capacity within the range of about pH 4 to about pH 10. In some embodiments, the one or more amino acid substitutions substantially remove the buffering capacity of the polymerase within the range of about pH 4 to about pH 10. For example, see Table 3.

In some embodiments, the one or more amino acid substitutions in the Bst DNA polymerase substantially reduce the buffering capacity of the polymerase relative to the corresponding unsubstituted polymerase within the range of about pH 7 to about pH 9. In some embodiments, the one or more amino acid substitutions substantially remove the buffering capacity of the Bst polymerase within the range of about pH 7 to about pH 9. In some embodiments, the one or more amino acid substitutions substantially reduce the buffering capacity of the Bst polymerase relative to the corresponding unsubstituted Bst polymerase within the range of about pH 7 to about pH 9. In some embodiments, the unsubstituted polymerase can be the wild-type version of the Bst polymerase.

In some embodiments, at least one of the one or more amino acid substitutions in the Bst DNA polymerase is a conservative amino acid substitution. In further embodiments, the at least one conservative amino acid substitution is selected from the group consisting of histidine to arginine, glutamic acid to glutamine, aspartic acid to asparagine, lysine to arginine, and tyrosine to phenylalanine.

In some embodiments, the one or more conservative amino acid substitutions are of one or more amino acid residues shown in Table 2. In some embodiments, the one or more conservative amino acid substitutions are selected from the group consisting of H46R, H273R, H281R, E446Q, H473R, H528R, H572R and Y477F, the numbering of amino acid residues being in accordance with that of SEQ ID NO: 1.

In some embodiments, the one or more amino acid substitutions includes a substitution of alanine at position 2 with Met, Asn, Gln, Leu, Ile, Phe, or Trp, the numbering of amino acid residues being in accordance with that of SEQ ID NO:2.

In some embodiments, the Bst DNA polymerase comprises an amino acid sequence selected from the group consisting of SEQ ID NO: 2, SEQ ID NO: 3 and SEQ ID NO: 4, or a variant thereof having one or more conservative amino acid substitutions. In some embodiments, the Bst DNA polymerase comprises the amino acid sequence of SEQ ID NO: 2. In some embodiments, the Bst DNA polymerase is a variant of a protein comprising the amino acid sequence shown in SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the Bst DNA polymerase comprises the amino acid sequence of SEQ ID NO: 3. In some embodiments, the Bst DNA polymerase is a variant of a protein comprising the amino acid sequence shown in SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the Bst DNA polymerase comprises the amino acid sequence of SEQ ID NO: 4. In other embodiments, the Bst polymerase is a variant of a protein comprising the amino acid sequence shown in SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the DNA polymerase is a Therminator™ DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a Therminator™ DNA polymerase comprising one or more conservative amino acid substitutions that substantially remove its buffering capacity within the range of about pH 7 to about pH 9, wherein the one or more conservative amino acid substitutions are selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 5.

In some embodiments, the DNA polymerase is a KOD DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a KOD DNA polymerase comprising one or more amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 6.

In some embodiments, the DNA polymerase is a B103 DNA polymerase comprising one or more conservative amino acid substitutions that substantially reduce its buffering capacity relative to the corresponding unsubstituted polymerase within the range of about pH 7 to about pH 9. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the DNA polymerase is a B103 DNA polymerase comprising one or more conservative amino acid substitutions that substantially reduce its buffering capacity relative to the corresponding unsubstituted polymerase within the range of about pH 4 to about pH 10. The unsubstituted polymerase can be the wild-type version of the polymerase. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In other embodiments of the method, the DNA polymerase is a B103 DNA polymerase comprising one or more conservative amino acid substitutions that substantially remove its buffering capacity within the range of about pH 7 to about pH 9. The one or more conservative amino acid substitutions are optionally selected from the group consisting of: histidine to arginine, glutamic acid to glutamine, lysine to arginine and tyrosine to phenylalanine. In some embodiments, the one or more conservative amino acid substitutions are of one or more amino acid residues shown in Table 7.

In some embodiments, the disclosure relates generally to a method for performing a nucleotide polymerization reaction comprising contacting a modified polymerase or a biologically active fragment thereof with a nucleic acid template in the presence of one or more nucleotides (e.g., any of the nucleotide analogues described herein), where the modified polymerase or the biologically active fragment thereof includes one or more amino acid modifications relative to a reference polymerase and where the modified polymerase or the biologically active fragment thereof has an increased dissociation time constant relative to the reference polymerase, and polymerizing at least one of the one or more nucleotides using the modified polymerase or the biologically active fragment thereof. In some embodiments, the method includes polymerizing at least one of the one or more nucleotides using the modified polymerase or the biologically active fragment thereof in the presence of a high ionic strength solution. In some embodiments, the method can further include polymerizing the at least one nucleotide in a template-dependent fashion. In some embodiments, the modified polymerase or the biologically active fragment thereof comprises or consists of at least 80% identity to SEQ ID NO: 23, SEQ ID NO: 24, SEQ ID NO: 25, SEQ ID NO: 36, SEQ ID NO: 39, SEQ ID NO: 40, SEQ ID NO: 41 or SEQ ID NO: 45. In some embodiments, the modified polymerase or the biologically active fragment thereof comprises at least 25 contiguous amino acids from the polymerase catalytic domain. In some embodiments, the modified polymerase or the biologically active fragment thereof comprises at least 25 contiguous amino acids from the polymerase DNA binding domain. In some embodiments, the modified polymerase or the biologically active fragment thereof comprises or consists of at least 100 amino acid residues having at least 80% identity to SEQ ID NO: 23, SEQ ID NO: 24, SEQ ID NO: 25, SEQ ID NO: 40, SEQ ID NO: 41 or SEQ ID NO: 45. In some embodiments, the modified polymerase or the biologically active fragment thereof comprises or consists of at least 150 amino acid residues of the polymerase catalytic domain having at least 90% identity to SEQ ID NO: 23, SEQ ID NO: 24, SEQ ID NO: 25, SEQ ID NO: 40, SEQ ID NO: 41 or SEQ ID NO: 45.

In some embodiments, the disclosure generally relates to a polymerase or a biologically active fragment thereof having DNA polymerase activity and at least 80% identity to SEQ ID NO: 22, SEQ ID NO: 36, SEQ ID NO: 37, or SEQ ID NO: 39.

In some embodiments, disclosure is generally related to an isolated and purified polypeptide comprising or consisting of a recombinant polymerase homologous to SEQ ID NO: 22 or biologically active fragment thereof comprises any one or more mutations relative to SEQ ID NO: 22 selected from the group consisting of: N31R, N31K, D77K, D77H, D113N, D114R, D130A, D130H, D144M, D144K, L212A, E220K, N234R, N234K, V241K, V251K, D264Q, D264S, D264K, Y272R, H273R, L280R, H281A, H281M, E294S, E294F, E294G, E294K, V299K, V299H, V299F, D303R, I331Q, E325R, L335T, E336P, I354 W, I354F, I370A, Q409R, G416K, V418M, V418I, G420K, D423S, D423K, D423N, D423R, D423T, D423G, D423I, D423K, G425R, Q428 W, N429R, N429K, E446Q, F448K, N457T, A462T, H473R, Y477F, D480R, D480F, D480H, D480A, D480S, D480N, D480Q, N485 W, N485Y, N487H, N487 W, N487F, N487I, V488R, E493Q, M495Q, H528A, H528R, H528K, V533I, H572R, W577Y and D579F.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a mutation or combination of mutations relative to SEQ ID NO: 22 selected from H46R, and where the polymerase further includes a mutation at one or more of E446Q, H572R, H273R, H281A, H473R, Y477F, D480R, or H528A.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a mutation or combination of mutations relative to SEQ ID NO: 22 selected from E446Q, where the polymerase further includes a mutation at one or more of H46R, H572R, H273R, H281A, H473R, Y477F, D480R, or H528A.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a mutation or combination of mutations relative to SEQ ID NO: 22 selected from H572R, where the polymerase further includes a mutation at one or more of E446Q, H572R, H273R, H281A, H473R, Y477F, D480R, or H528A.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a C93 mutation.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a Q238 mutation.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a H273 mutation.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a H281 mutation.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a H473 mutation.

In some embodiments, the disclosure relates generally to a composition comprising a recombinant polymerase homologous to SEQ ID NO: 22 or a biologically active fragment thereof having at least 80% identity to SEQ ID NO: 22 or a biologically active fragment thereof and where the recombinant polymerase comprises a H528 mutation.

In some embodiments, disclosure is generally related to an isolated and purified polypeptide comprising or consisting of at least 80% identity to SEQ ID NO: 23 and having one or more amino acid mutations selected from the group consisting of N31R, N31K, D77K, D77H, D113N, D114R, D130A, D130H, D144M, D144K, L212A, E220K, N234R, N234K, V241K, V251K, D264Q, D264S, D264K, Y272R, H273R, L280R, H281A, E294S, E294F, E294G, E294K, V299K, V299H, V299F, D303R, I331Q, E325R, L335T, E336P, I354 W, I354F, I370A, Q409R, G416K, V418M, V418I, G420K, D423S, D423K, D423N, D423R, D423T, D423G, D423I, D423K, G425R, Q428 W, N429R, N429K, F448K, N457T, A462T, H473R, Y477F, D480R, D480F, D480H, D480A, D480S, D480N, D480Q, N485 W, N485Y, N487H, N487 W, N487F, N487I, V488R, E493Q, M495Q, H528A, V533I, W577Y and D579F.

In some embodiments, disclosure is generally related to an isolated and purified polypeptide comprising or consisting of at least 80% identity to SEQ ID NO: 36 and having one or more amino acid mutations selected from the group consisting of E471K, N485R, R492K, D513K, A675K, D732R, S739 W, V740R and E745Q.

In some embodiments, the disclosure generally relates to a composition comprising a recombinant polymerase homologous to SEQ ID NO: 36 or a biologically active fragment thereof having at least 80% identity to SEQ ID NO: 36 or a biologically active fragment thereof and where the recombinant polymerase comprises a mutation or combination of mutations relative to SEQ ID NO: 36 selected from E471K, wherein the polymerase further includes a mutation at one or more of: N485R, R492K, D513K, A675K, D732R, S739 W, V740R and E745Q.

In some embodiments, the disclosure generally relates to a composition comprising a recombinant polymerase homologous to SEQ ID NO: 36 or a biologically active fragment thereof having at least 80% identity to SEQ ID NO: 36 or a biologically active fragment thereof and where the recombinant polymerase comprises a mutation or combination of mutations relative to SEQ ID NO: 36 selected from V740R, wherein the polymerase further includes a mutation at one or more of: E471K, N485R, D513K and E745Q.

In some embodiments, the disclosure generally relates to a composition comprising a recombinant polymerase homologous to SEQ ID NO: 36 or a biologically active fragment thereof having at least 80% identity to SEQ ID NO: 36 or a biologically active fragment thereof and where the recombinant polymerase comprises a N485 mutation.

In some embodiments, the disclosure generally relates to a composition comprising a recombinant polymerase homologous to SEQ ID NO: 36 or a biologically active fragment thereof having at least 80% identity to SEQ ID NO: 36 or a biologically active fragment thereof and where the recombinant polymerase comprises a mutation or combination of mutations relative to SEQ ID NO: 36 selected from a D513 mutation.

In some embodiments, the disclosure generally relates to a composition comprising a recombinant polymerase homologous to SEQ ID NO: 36 or a biologically active fragment thereof having at least 80% identity to SEQ ID NO: 36 or a biologically active fragment thereof and where the recombinant polymerase comprises a mutation or combination of mutations relative to SEQ ID NO: 36 selected from a D732 mutation.

In some embodiments, the disclosure generally relates to a composition comprising a recombinant polymerase homologous to SEQ ID NO: 36 or a biologically active fragment thereof having at least 80% identity to SEQ ID NO: 36 or a biologically active fragment thereof and where the recombinant polymerase comprises a mutation or combination of mutations relative to SEQ ID NO: 36 selected from an E745 mutation.

In some embodiments, the reference polymerase has or comprises the amino acid sequence of SEQ ID NO: 36, and the modified polymerase has or comprises the amino acid sequence of the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes any one or more amino acid mutations selected from the group consisting of: N326R, N326K, D372K, D372H, D408N, D409R, D425A, D425H, D439M, D439K, L507A, E515K, N529R, N529K, V536K, V546K, D559Q, D559S, Y567R, L575R, E589S, E589F, E589G, V594K, V594H, V594F, D598R, I626Q, L630T, E631P, I649 W, I649F, I665A, Q704R, G711K, V713M, V713I, G715K, D718S, D718K, D718N, D718R, D718T, D718G, D718I, D718K, G720R, Q723 W, N724R, N724K, F743K, N752T, A757T, D775R, D775F, D775H, D775A, D775S, D775N, D775Q, N780 W, N780Y, N782H, N782 W, N782F, N782I, E782Q, V783R, E788Q, M790Q, V828I, W872Y and D874F, wherein the numbering is relative of the amino acid sequence of SEQ ID NO: 37.

In some embodiments, the reference polymerase has or comprises the amino acid sequence of SEQ ID NO: 37, and the modified polymerase has or comprises the amino acid sequence of the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes any one or more amino acid mutations selected from the group consisting of: N326R, N326K, H341R, D372K, D372H, C388R, D408N, D409R, D425A, D425H, D439M, D439K, L507A, E515K, N529R, N529K, V536K, V546K, Q533C, D559Q, D559S, Y567R, H568R, L575R, H576A, E589S, E589F, E589G, V594K, V594H, V594F, D598R, I626Q, L630T, E631P, I649 W, I649F, I665A, Q704R, G711K, V713M, V713I, G715K, D718S, D718K, D718N, D718R, D718T, D718G, D718I, D718K, G720R, Q723 W, N724R, N724K, E741Q, F743K, N752T, A757T, H768R, Y772F, D775R, D775F, D775H, D775A, D775S, D775N, D775Q, N780 W, N780Y, N782H, N782 W, N782F, N782I, E782Q, V783R, E788Q, M790Q, H823A, V828I, C845Q, H867R, W872Y and D874F, wherein the numbering is relative of the amino acid sequence of SEQ ID NO: 37.

In some embodiments, disclosure is generally related to an isolated and purified polypeptide comprising or consisting of at least 80% identity to SEQ ID NO: 39 and having one or more amino acid mutations selected from the group consisting of E245K, S259R, T266K, E290K, A448K, D505R, A512 W, R513R and E518Q.

In some embodiments, the disclosure is generally related to a composition comprising a recombinant polymerase homologous to SEQ ID NO: 39 or a biologically active fragment thereof having at least 80% identity to SEQ ID NO: 39 or a biologically fragment thereof and where the recombinant polymerase comprises a mutation or combination of mutations relative to SEQ ID NO: 39 selected from E245K, where the polymerase further includes a mutation at one or more of: S259R, T266K, E290K, A448K, D505R, A512 W, R513R and E518Q.

In some embodiments, the disclosure is generally related to a composition comprising a recombinant polymerase homologous to SEQ ID NO: 39 or a biologically active fragment thereof having at least 80% identity to SEQ ID NO: 39 or a biologically fragment thereof and where the recombinant polymerase comprises a mutation or combination of mutations relative to SEQ ID NO: 39 selected from D505R, where the polymerase further includes a mutation at one or more of: E245K, S259R, T266K, E290K, A448K, A512 W, R513R and E518Q.

In some embodiments, the disclosure is generally related to a composition comprising a recombinant polymerase homologous to SEQ ID NO: 39 or a biologically active fragment thereof having at least 80% identity to SEQ ID NO: 39 or a biologically fragment thereof and where the recombinant polymerase comprises an E290 mutation.

In some embodiments, the disclosure is generally related to a composition comprising a recombinant polymerase homologous to SEQ ID NO: 39 or a biologically active fragment thereof having at least 80% identity to SEQ ID NO: 39 or a biologically fragment thereof and where the recombinant polymerase comprises an S259 mutation.

In some embodiments, the disclosure is generally related to a composition comprising a recombinant polymerase homologous to SEQ ID NO: 39 or a biologically active fragment thereof having at least 80% identity to SEQ ID NO: 39 or a biologically fragment thereof and where the recombinant polymerase comprises an R513 mutation.

In some embodiments, the disclosure is generally related to a composition comprising a recombinant polymerase homologous to SEQ ID NO: 39 or a biologically active fragment thereof having at least 80% identity to SEQ ID NO: 39 or a biologically fragment thereof and where the recombinant polymerase comprises an A512 mutation.

In some embodiments, the disclosure relates generally to a method for performing a nucleotide polymerization reaction comprising or consisting of contacting a modified polymerase or a biologically active fragment thereof with a nucleic acid template in the presence of one or more nucleotides (e.g., any of the nucleotide analogues described herein), where the modified polymerase or the biologically active fragment thereof includes one or more amino acid modifications relative to a reference polymerase and where the modified polymerase or the biologically active fragment thereof has a lowered systematic error, decreased strand bias, increased raw read accuracy and/or increased total sequencing throughput as compared to the reference polymerase, and polymerizing at least one of the one or more nucleotides using the modified polymerase or the biologically active fragment thereof.

In some embodiments, the isolated or modified polymerases as disclosed herein can include a fusion of a first naturally occurring polymerase domain (e.g., a catalytic domain) with a first genetically engineered polymerase domain (e.g., a binding domain). In some embodiments, the isolated or modified polymerases disclosed herein can include a fusion of a first genetically engineered polymerase domain (e.g., a catalytic domain) to a second genetically engineered polymerase domain (e.g., a binding domain), thereby forming an isolated or modified polymerase retaining polymerase activity.

In some embodiments, the modified polymerase or the biologically active fragment thereof comprises or consists of at least 80% identity, or at least 90% identity, or at least 95% identity, or at least 98% identity, or at least 99% identity to SEQ ID NO: 47, SEQ ID NO: 48, SEQ ID NO: 49, SEQ ID NO: 64, SEQ ID NO: 65, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81 or SEQ ID NO: 82.

In some embodiments, the modified polymerase or the biologically active fragment thereof comprises at least 25 contiguous amino acids from the polymerase catalytic domain. In some embodiments, the modified polymerase or the biologically active fragment thereof comprises at least 25 contiguous amino acids from the polymerase DNA binding domain. In some embodiments, the modified polymerase or the biologically active fragment thereof comprises or consists of at least 100 amino acid residues having at least 80% identity to SEQ ID NO: 47, SEQ ID NO: 48, SEQ ID NO: 49, SEQ ID NO: 64, SEQ ID NO: 65, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81 or SEQ ID NO: 82. In some embodiments, the modified polymerase or the biologically active fragment thereof comprises or consists of at least 150 amino acid residues of the polymerase catalytic domain having at least 90% identity to SEQ ID NO: 47, SEQ ID NO: 48, SEQ ID NO: 49, SEQ ID NO: 64, SEQ ID NO: 65, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81 or SEQ ID NO: 82.

In some embodiments, the method includes amplifying conditions having a high ionic strength solution. In some embodiments, amplifying conditions having a high ionic strength solution include at least 120 mM salt. In some embodiments, amplifying conditions having a high ionic strength solution include 125 mM salt. In some embodiments, amplifying conditions having a high ionic strength solution include 125 mM to 200 mM salt. In some embodiments, the salt can include KCl and/or NaCl.

In some embodiments, the disclosure is generally related to an isolated and purified polypeptide comprising or consisting of at least 80% identity to SEQ ID NO: 46 or a biologically active fragment thereof and having one or more amino acid mutations (e.g., substitutions) selected from the group consisting of N31R, N31K, H46R, D77K, D77H, D113N, D114R, D130A, D130H, D144M, D144K, L212A, E220K, N234R, N234K, V241K, V251K, A263K, D264A, D264R, D264Q, D264S, D264K, Y272R, H273N, H273R, L280R, H281A, H281M, E294S, E294F, E294G, E294K, V299K, V299H, V299F, D303R, I331Q, E325R, L335T, E336P, I354 W, I354F, I370A, Q409R, G416K, V418M, V418I, G420K, D423S, D423K, D423N, D423R, D423T, D423G, D423I, D423K, G425R, Q428 W, N429R, N429K, E446Q, F448K, N457T, A462T, H473R, Y477F, D480R, D480F, D480H, D480A, D480S, D480N, D480Q, N485K N485 W, N485Y, N487H, N487R N487 W, N487F, N487I, V488R, E493Q, E493R, M495Q, H528A, H528F, H528S, V533I, H572R, W577Y and D579F, wherein the numbering is relative to the amino acid sequence of SEQ ID NO: 46.

In some embodiments, the disclosure is generally related to an isolated and purified polypeptide comprising or consisting of at least 80% identity to SEQ ID NO: 47 or a biologically active fragment thereof and having one or more amino acid mutations (e.g., substitutions) selected from the group consisting of N31R, N31K, D77K, D77H, D113N, D114R, D130A, D130H, D144M, D144K, L212A, E220K, N234R, N234K, V241K, V251K, D264A, D264R, D264Q, D264S, D264K, Y272R, H273N, H273R, L280R, H281A, H281M, E294S, E294F, E294G, E294K, V299K, V299H, V299F, D303R, I331Q, E325R, L335T, E336P, I354 W, I354F, I370A, Q409R, G416K, V418M, V418I, G420K, D423S, D423K, D423N, D423R, D423T, D423G, D423I, D423K, G425R, Q428 W, N429R, N429K, F448K, N457T, A462T, H473R, Y477F, D480R, D480F, D480H, D480A, D480S, D480N, D480Q, N485K N485 W, N485Y, N487H, N487R N487 W, N487F, N487I, V488R, E493Q, E493R, M495Q, H528A, H528F, H528S, V533I, W577Y and D579F, wherein the numbering is relative to the amino acid sequence of SEQ ID NO: 47.

In some embodiments, the disclosure is generally related to an isolated and purified polypeptide having at least 90% identity to SEQ ID NO: 47 and includes an amino acid substitution at one or more positions corresponding to positions selected from the group consisting of: N487, N485, E493, A263, D264, H528, H273, D423, D480, H281, E220 and N234, wherein the numbering is relative to SEQ ID NO: 47.

In some embodiments, the disclosure is generally related to an isolated and purified polypeptide comprising or consisting of at least 80% identity to SEQ ID NO: 60 or a biologically active fragment thereof and having one or more amino acid mutations selected from the group consisting of E471K, N485R, R492K, D513K, A675K, D732R, S739 W, V740R and E745Q, wherein the numbering is relative to the amino acid sequence of SEQ ID NO: 60.

In some embodiments, the recombinant polymerase homologous to SEQ ID NO: 60, comprises a mutation or combination of mutations relative to SEQ ID NO: 60 selected from any one or more of: E471K, N485R, R492K, D513K, A675K, D732R, S739 W, V740R and E745Q.

In some embodiments, the disclosure is generally related to an isolated and purified polypeptide comprising or consisting of at least 80% identity to SEQ ID NO: 61 or a biologically active fragment thereof and having one or more amino acid mutations (e.g., substitutions) selected from any one or more of: N782R, N780K, E788R, A558K, D559A, D559R, H823S, H823F, H568N, D718K, D775R, H576M, E515K and N529R, wherein the numbering is relative to the amino acid sequence of SEQ ID NO: 61.

In some embodiments, the recombinant polymerase homologous to SEQ ID NO: 61, comprises a mutation or combination of mutations relative to SEQ ID NO: 61 selected from any one or more of: H341R, C388R, Q533C, H568R, H576A, E741Q, H768R, Y772F, H823A, C845Q, H867R, N782R, N780K, E788R, A558K, D559A, D559R, H823S, H823F, H568N, D718K, D775R, H576M, E515K and N529R, wherein the numbering is relative to the amino acid sequence of SEQ ID NO: 61.

In some embodiments, the disclosure is generally related to an isolated and purified polypeptide comprising or consisting of at least 80% identity to SEQ ID NO: 63 or a biologically active fragment thereof and having one or more amino acid mutations selected from the group consisting of E245K, S259R, T266K, E290K, A448K, D505R, A512 W, R513R and E518Q, wherein the numbering is relative to SEQ ID NO: 63.

In some embodiments, the recombinant polymerase homologous to SEQ ID NO: 63, comprises a mutation or combination of mutations relative to SEQ ID NO: 63 selected from any one of more of: E245K, S259R, T266K, E290K, A448K, D505R, A512 W, and E518Q, wherein the numbering is relative to SEQ ID NO: 63.

In some embodiments, the disclosure is generally related to an isolated and purified polypeptide comprising or consisting of at least 90% identity to SEQ ID NO: 70 and includes an amino acid substitution at one or more positions corresponding to positions selected from the group consisting of: N780K, E788R, A558K, D559A, D559R, H823S, H823F, H568N, D718K, D775R, H576M, E515K and N529R, wherein the numbering is relative to SEQ ID NO: 70.

In some embodiments, the disclosure is generally related to an isolated and purified polypeptide comprising or consisting of at least 80% identity to SEQ ID NO: 71 or a biologically active fragment thereof and having one or more amino acid mutations selected from the group consisting of N780K, E788R, A558K, D559A, D559R, H823S, H823F, D775R, H576M, H568N, E515K and N529R, wherein the numbering is relative to the amino acid sequence of SEQ ID NO: 71.

In some embodiments, the disclosure is generally related to an isolated and purified polypeptide comprising or consisting of at least 80% identity to SEQ ID NO: 72 or a biologically active fragment thereof and having one or more amino acid mutations selected from the group consisting of N780K, E788R, A558K, D559A, D559R, H823S, H823F, D775R, H576M, E515K and N529R, wherein the numbering is relative to the amino acid sequence of SEQ ID NO: 72.

In some embodiments, the disclosure is generally related to an isolated and purified polypeptide comprising at least 90% identity to SEQ ID NO: 73 and includes an amino acid substitution at one or more positions corresponding to positions selected from the group consisting of: N780K, E788R, A558K, D559A, D559R, H823S, H823F, D718K, D775R, H568N, E515K and N529R, wherein the numbering is relative to SEQ ID NO: 73.

In some embodiments, the disclosure is generally related to an isolated and purified polypeptide comprising or consisting of at least 80% identity to SEQ ID NO: 74 or a biologically active fragment thereof and having one or more amino acid mutations selected from the group consisting of N780K, E788R, A558K, D559A, D559R, D718K, D775R, H576M, H568N, E515K and N529R, wherein the numbering is relative to the amino acid sequence of SEQ ID NO: 74.

In some embodiments, the disclosure is generally related to an isolated and purified polypeptide comprising at least 90% identity to SEQ ID NO: 82 and includes an amino acid substitution at one or more positions corresponding to positions selected from the group consisting of: N485, E493, A263, D264, H528, H273, D423 and D480, wherein the numbering is relative to SEQ ID NO: 82.

In some embodiments, the disclosure relates generally to a composition comprising a recombinant polymerase homologous to SEQ ID NO: 46 or a biologically active fragment thereof having at least 80% identity to SEQ ID NO: 46 or a biologically active fragment thereof and where the recombinant polymerase homologous to SEQ ID NO: 46 comprises a mutation or combination of mutations relative to SEQ ID NO: 46 selected from H46R, and where the polymerase further includes a mutation at one or more of E446Q, H572R, H273R, H281A, H473R, Y477F, D480R, or H528A, wherein the numbering is relative to SEQ ID NO: 46.

In some embodiments, the disclosure relates generally to a composition comprising a recombinant polymerase homologous to SEQ ID NO: 46 or a biologically active fragment thereof having at least 80% identity to SEQ ID NO: 46 or a biologically active fragment thereof and where the recombinant polymerase homologous to SEQ ID NO: 46 comprises a mutation or combination of mutations relative to SEQ ID NO: 1 selected from E446Q, where the polymerase further includes a mutation at one or more of H46R, H572R, H273R, H281A, H473R, Y477F, D480R, or H528A, wherein the numbering is relative to SEQ ID NO: 46.

In some embodiments, the disclosure relates generally to a composition comprising a recombinant polymerase homologous to SEQ ID NO: 46 or a biologically active fragment thereof having at least 80% identity to SEQ ID NO: 46 or a biologically active fragment thereof and where the recombinant polymerase homologous to SEQ ID NO: 46 comprises a mutation or combination of mutations relative to SEQ ID NO: 46 selected from H572R, where the polymerase further includes a mutation at one or more of H46R, E446Q, H572R, H273R, H281A, H473R, Y477F, D480R, or H528A, wherein the numbering is relative to SEQ ID NO: 46.

In some embodiments, the disclosure relates generally to a composition comprising a recombinant polymerase homologous to SEQ ID NO: 47 or a biologically active fragment thereof having at least 80% identity to SEQ ID NO: 47 or a biologically active fragment thereof and where the recombinant polymerase homologous to SEQ ID NO: 47 comprises a mutation or combination of mutations relative to SEQ ID NO: 47 selected from N487R, and where the recombinant polymerase further includes a mutation at one or more of H281M, D423K, H273N, E493R, and D264A, wherein the numbering is relative to SEQ ID NO: 47.

In some embodiments, the disclosure relates generally to a composition comprising a recombinant polymerase homologous to SEQ ID NO: 47 or a biologically active fragment thereof having at least 80% identity to SEQ ID NO: 47 or a biologically active fragment thereof and where the recombinant polymerase homologous to SEQ ID NO: 47 comprises a mutation or combination of mutations relative to SEQ ID NO: 47 selected from H281M, where the recombinant polymerase further includes a mutation at one or more of N487R, D264A, H273N and E493R, wherein the numbering is relative to SEQ ID NO: 47.

In some embodiments, the disclosure relates generally to a composition comprising a recombinant polymerase homologous to SEQ ID NO: 47 or a biologically active fragment thereof having at least 80% identity to SEQ ID NO: 47 or a biologically active fragment thereof and where the recombinant polymerase homologous to SEQ ID NO: 47 comprises a mutation or combination of mutations relative to SEQ ID NO: 47 selected from E493R where the recombinant polymerase further includes a mutation at one or more of N487R, H281M, D423K, D264A, or H273N, wherein the numbering is relative to SEQ ID NO: 47.

In some embodiments, the disclosure generally relates to a composition comprising a recombinant polymerase homologous to SEQ ID NO: 60 or a biologically active fragment thereof having at least 80% identity to SEQ ID NO: 60 or a biologically active fragment thereof and where the recombinant polymerase homologous to SEQ ID NO: 60 comprises a mutation or combination of mutations relative to SEQ ID NO: 60 selected from E471K, wherein the polymerase further includes a mutation at one or more of: N485R, R492K, D513K, A675K, D732R, S739 W, V740R and E745Q, wherein the numbering is relative to SEQ ID NO: 60.

In some embodiments, the disclosure generally relates to a composition comprising a recombinant polymerase homologous to SEQ ID NO: 60 or a biologically active fragment thereof having at least 80% identity to SEQ ID NO: 60 or a biologically active fragment thereof and where the recombinant polymerase homologous to SEQ ID NO: 60 comprises a mutation or combination of mutations relative to SEQ ID NO: 60 selected from V740R, wherein the polymerase further includes a mutation at one or more of: E471K, N485R, D513K and E745Q, wherein the numbering is relative to SEQ ID NO: 60.

In some embodiments, the disclosure relates generally to a composition comprising a recombinant polymerase homologous to SEQ ID NO: 61 or a biologically active fragment thereof having at least 80% identity to SEQ ID NO: 61 or a biologically active fragment thereof and where the recombinant polymerase homologous to SEQ ID NO: 61 comprises a mutation or combination of mutations relative to SEQ ID NO: 61 selected from N782R, and where the recombinant polymerase further includes a mutation at one or more of N780K, E788R, A558K, D559A, D559R, H823S, H823F, H568N, D718K, D775R, E515K, N529R, or H576M, wherein the numbering is relative to SEQ ID NO: 61.

In some embodiments, the disclosure relates generally to a composition comprising a recombinant polymerase homologous to SEQ ID NO: 61 or a biologically active fragment thereof having at least 80% identity to SEQ ID NO: 61 or a biologically active fragment thereof and where the recombinant polymerase comprises a mutation or combination of mutations relative to SEQ ID NO: 61 selected from N780K, where the recombinant polymerase further includes a mutation at one or more of N782R, E788R, A558K, D559A, D559R, H823S, H823F, H568N, D718K, D775R, E515K, N529R, or H576M, wherein the numbering is relative to SEQ ID NO: 61.

In some embodiments, the disclosure relates generally to a composition comprising a recombinant polymerase homologous to SEQ ID NO: 61 or a biologically active fragment thereof having at least 80% identity to SEQ ID NO: 61 or a biologically active fragment thereof and where the recombinant polymerase homologous to SEQ ID NO: 61 comprises a mutation or combination of mutations relative to SEQ ID NO: 61 selected from E788R where the recombinant polymerase further includes a mutation at one or more of N782R, N780K, A558K, D559A, D559R, H823S, H823F, H568N, D718K, D775R, E515K, N529R, or H576M, wherein the numbering is relative to SEQ ID NO: 61.

In some embodiments, the disclosure is generally related to a composition comprising a recombinant polymerase homologous to SEQ ID NO: 63 or a biologically active fragment thereof having at least 80% identity to SEQ ID NO: 63 or a biologically fragment thereof and where the recombinant polymerase homologous to SEQ ID NO: 63 comprises a mutation or combination of mutations relative to SEQ ID NO: 63 selected from E245K, where the polymerase further includes a mutation at one or more of: S259R, T266K, E290K, A448K, D505R, A512 W, R513R and E518Q, wherein the numbering is relative to SEQ ID NO: 63.

In some embodiments, the disclosure is generally related to a composition comprising a recombinant polymerase homologous to SEQ ID NO: 63 or a biologically active fragment thereof having at least 80% identity to SEQ ID NO: 63 or a biologically fragment thereof and where the recombinant polymerase homologous to SEQ ID NO: 63 comprises a mutation or combination of mutations relative to SEQ ID NO: 63 selected from E245K, where the polymerase further includes a mutation at one or more of: S259R, T266K, E290K, A448K, D505R, A512 W, R513R and E518Q, wherein the numbering is relative to SEQ ID NO: 63.

In some embodiments, the disclosure is generally related to a composition comprising a recombinant polymerase homologous to SEQ ID NO: 63 or a biologically active fragment thereof having at least 80% identity to SEQ ID NO: 63 or a biologically fragment thereof and where the recombinant polymerase homologous to SEQ ID NO: 63 comprises a mutation or combination of mutations relative to SEQ ID NO: 63 selected from D505R, where the polymerase further includes a mutation at one or more of: E245K, S259R, T266K, E290K, A448K, A512 W, R513R and E518Q, wherein the numbering is relative to SEQ ID NO: 63.

In some embodiments, the disclosure generally relates to a composition comprising a recombinant polymerase homologous to SEQ ID NO: 70 or a biologically active fragment thereof having at least 80% identity to SEQ ID NO: 70 or a biologically active fragment thereof and where the recombinant polymerase homologous to SEQ ID NO: 70 comprises a mutation or combination of mutations relative to SEQ ID NO: 70 selected from D718K, wherein the polymerase further includes a mutation at one or more of: N780K, E788R, A558K, D559A, D559R, H823S, H823F, H568N, D775R, and H576M, wherein the numbering is relative to SEQ ID NO: 70.

In some embodiments, the disclosure generally relates to a composition comprising a recombinant polymerase homologous to SEQ ID NO: 70 or a biologically active fragment thereof having at least 80% identity to SEQ ID NO: 70 or a biologically active fragment thereof and where the recombinant polymerase homologous to SEQ ID NO: 70 comprises a mutation or combination of mutations relative to SEQ ID NO: 70 selected from H568N, wherein the polymerase further includes a mutation at one or more of: N780K, E788R, A558K, D559A, D559R, H823S, H823F, D718K, D775R, or H576M, wherein the numbering is relative to SEQ ID NO: 70.

In some embodiments, the disclosure relates generally to a composition comprising a recombinant polymerase homologous to SEQ ID NO: 71 or a biologically active fragment thereof having at least 80% identity to SEQ ID NO: 71 or a biologically active fragment thereof and where the recombinant polymerase homologous to SEQ ID NO: 71 comprises a mutation or combination of mutations relative to SEQ ID NO: 71 selected from H568N, where the polymerase further includes a mutation at one or more of N780K, E788R, A558K, D559A, D559R, H823S, H823F, D775R, or H576M, wherein the numbering is relative to SEQ ID NO: 71.

In some embodiments, the disclosure is generally related to a composition comprising a recombinant polymerase homologous to SEQ ID NO: 73 or a biologically active fragment thereof having at least 80% identity to SEQ ID NO: 73 or a biologically fragment thereof and where the recombinant polymerase homologous to SEQ ID NO: 73 comprises a mutation or combination of mutations relative to SEQ ID NO: 73 selected from D718K, where the polymerase further includes a mutation at one or more of: A558K, H823S, H823F, D559A, D559R, D568N, D775R, E788R, N780K, E515K and N529R, wherein the numbering is relative to SEQ ID NO: 73.

In some embodiments, the disclosure is generally related to a composition comprising a recombinant polymerase homologous to SEQ ID NO: 74 or a biologically active fragment thereof having at least 80% identity to SEQ ID NO: 74 or a biologically fragment thereof and where the recombinant polymerase comprises a mutation or combination of mutations relative to SEQ ID NO: 74 selected from D718K, where the polymerase further includes a mutation at one or more of: A558K, D559A, D559R, D568N, D775R, E788R, H576M, N780K, E515K and N529R, wherein the numbering is relative to SEQ ID NO: 74.

In some embodiments, the disclosure generally relates to a composition comprising a recombinant polymerase homologous to SEQ ID NO: 75 or a biologically active fragment thereof having at least 80% identity to SEQ ID NO: 75 or a biologically active fragment thereof and where the recombinant polymerase homologous to SEQ ID NO: 75 comprises a mutation or combination of mutations relative to SEQ ID NO: 75 selected from N782R, wherein the polymerase further includes a mutation at one or more of A558K, D559A, D559R, H823S, H823F, H568N, and H576M, wherein the numbering is relative to SEQ ID NO: 75.

In some embodiments, the disclosure generally relates to a composition comprising a recombinant polymerase homologous to SEQ ID NO: 75 or a biologically active fragment thereof having at least 80% identity to SEQ ID NO: 75 or a biologically active fragment thereof and where the recombinant polymerase homologous to SEQ ID NO: 75 comprises a mutation or combination of mutations relative to SEQ ID NO: 75 selected from H568N, wherein the polymerase further includes a mutation at one or more of: N780K, E788R, A558K, D559A, D559R, H823S, H823F, D775R, or H576M, wherein the numbering is relative to SEQ ID NO: 75.

In some embodiments, the disclosure relates generally to a composition comprising a recombinant polymerase homologous to SEQ ID NO: 76 or a biologically active fragment thereof having at least 80% identity to SEQ ID NO: 76 or a biologically active fragment thereof and where the recombinant polymerase homologous to SEQ ID NO: 76 comprises a mutation or combination of mutations relative to SEQ ID NO: 76 selected from H568N, where the polymerase further includes a mutation at one or more of N780K, E788R, A558K, D559A, D559R, H823S, H823F, D775R, or H576M, wherein the numbering is relative to SEQ ID NO: 76.

In some embodiments, the disclosure relates generally to a composition comprising a recombinant polymerase homologous to SEQ ID NO: 77 or a biologically active fragment thereof having at least 80% identity to SEQ ID NO: 77 or a biologically active fragment thereof and where the recombinant polymerase homologous to SEQ ID NO: 77 comprises a mutation or combination of mutations relative to SEQ ID NO: 77 selected from D718K, where the polymerase further includes a mutation at one or more of N780K, A558K, H823S, H823F, or D775R, wherein the numbering is relative to SEQ ID NO: 77.

In some embodiments, the disclosure relates generally to an isolated and purified polypeptide (e.g., a fusion polypeptide) comprising or consisting of at least 90% identity to SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81 or SEQ ID NO: 82, or a biologically active fragment thereof and can optionally further include one or more amino acid mutations selected from the group consisting of E515K and N529R, wherein the numbering is relative to the amino acid sequence of SEQ ID NO: 61. In some embodiments, the recombinant polymerase homologous to SEQ ID NO: 61, SEQ ID NO: 70, SEQ ID NO: 71, SEQ ID NO: 72, SEQ ID NO: 73, SEQ ID NO: 74, SEQ ID NO: 75, SEQ ID NO: 76, or SEQ ID NO: 77 can optionally further include one or more mutations selected from the group consisting of E515K and N529R, wherein the numbering is relative to SEQ ID NO: 61.

In some embodiments, a template nucleic acid is hybridized to a primer and bound to a polymerase, where the template nucleic acid comprises a single-stranded or double-stranded polynucleotide, or a mixture of both. In some embodiments, the polynucleotide includes a plurality of polynucleotides having the same or different sequences. In some embodiments, the plurality of polynucleotides have the same or different lengths. In some embodiments, the plurality of polynucleotides comprises about 2-10, or about 10-50, or about 50-100, or about 100-500, or about 500-1, 000, or about 1,000-5,000, or about $10^3$-$10^6$, or about $10^6$-$10^{10}$, or more different polynucleotides. In some embodiments, a plurality of polynucleotides comprises polymers of deoxyribonucleotides, ribonucleotides, and/or analogs thereof. In some embodiments, a plurality of polynucleotides comprises naturally-occurring, synthetic, recombinant, cloned, amplified, unamplified or archived (e.g., preserved) forms. In some embodiments, a plurality of polynucleotides comprises DNA, cDNA RNA or chimeric RNA/DNA, and nucleic acid analogs.

In some embodiments, a template nucleic acid comprises any nucleic acid, including DNA, cDNA, RNA, or RNA/DNA hybrids. The template nucleic acid can be single-stranded or double-stranded nucleic acids, and can have any length. The template nucleic acid can be chromosomal, genomic, transcriptomic, organellar, methylated, chromatin-linked, cloned, unamplified, amplified, natural or synthetic, and can be isolated from any source (for example, from an organism, normal or diseased cells or tissues, body fluids, archived tissue (e.g., tissue archived in formalin and/or in paraffin). In some embodiments, the template nucleic acid can be isolated from any source including prokaryotes, eukaryotes (e.g., humans, plants and animals), fungus, and viruses; cells; tissues; normal or diseased cells or tissues or organs, body fluids including blood, urine, serum, lymph, tumor, saliva, anal and vaginal secretions, amniotic samples, perspiration, and semen; environmental samples; culture samples; or synthesized nucleic acid molecules prepared using recombinant molecular biology or chemical synthesis methods. In some embodiments, the template nucleic acid can be isolated from a formalin-fixed tissue, or from a paraffin-embedded tissue, or from a formalin-fix paraffin-embedded (FFPE) tissue. In some embodiments, a template molecule can be about 100 bp-1000 bp, or about 1 kb-50 kb, or about 50 kb-100 kb, or longer.

In some embodiments, the template nucleic acid includes at least one primer binding site. The template nucleic acid can be generated by joining together an initial polynucleotide (from any source) to a nucleic acid adaptor having a primer binding sequence. For example, the initial polynucleotide and adaptor can be joined by ligation, hybridization or primer extension methods. An adapter can be joined to at least one end of a linear template, or within the body of a linear or circular initial polynucleotide. Optionally, the template can be circularized after the adapter is joined.

In some embodiments, primers comprise polymers of deoxyribonucleotides, ribonucleotides, and/or analogs thereof. In some embodiments, primers comprise naturally-occurring, synthetic, recombinant, cloned, amplified, or unamplified forms. In some embodiments, primers comprise DNA, cDNA RNA, chimeric RNA/DNA, or nucleic acid analogs. In some embodiments, primers comprise single-stranded or double-stranded forms.

In some embodiments, at least a portion of a primer can hybridize with a portion of at least one strand of a template polynucleotide in the reaction mixture. In some embodiments, at least a portion of a primer can be partially or fully complementary to a portion of the template polynucleotide. A template polynucleotide can include a polynucleotide sequence of interest, or a nucleic acid adaptor sequence joined to the polynucleotide sequence of interest.

In some embodiments, a primer can include or lack a terminal 3'OH which can serve as an initiation site for nucleotide incorporation. In some embodiments, a primer can include a terminal 3' blocking group that does not serve as an initiation site for nucleotide incorporation.

In some embodiments, primers can be any length, including about 5-20 nucleotides, or about 20-40 nucleotides, or about 40-60 nucleotides, or about 60-80 nucleotides, or longer.

In some embodiments, a primer can have a 5' or 3' overhang tail (tailed primer) that does not hybridize with a portion of at least one strand of a template polynucleotide. In some embodiments, a non-complementary portion of a tailed primer can be any length, including 1-50 or more nucleotides in length.

In some embodiments, a plurality of primers includes individual primers that are essentially the same or are different. For example, primers in the plurality can have essentially the same sequences or different sequences, or can have essentially the same length or different lengths, or can include natural or synthetic forms or a mixture of both.

In some embodiments, a reaction mixture can contain at least one reagent for conducting a nucleotide incorporation reaction. For example, a reaction mixture can include any one or any combination of reagents: at least one nucleotide, one or more polymerases, at least one template molecule, at least one primer, at least one divalent cation. Optionally, a reaction mixture can include other enzymes, including at least one phosphatase. Optionally, a reaction mixture can include at least one accessory protein that can: bind single-stranded or double-stranded nucleic acids; mediate loading other protein onto a nucleic acid; unwind nucleic acid substrates; relax nucleic acids; resolve nucleic acid structures; disassemble complexes of nucleic acids and proteins, or disassemble nucleic acid structures; or hydrolyze nucleic acids. In some embodiments, an accessory protein comprises a sliding clamp protein. In some embodiments, an accessory protein comprises a multimeric protein complex. In some embodiments, a multimeric protein complex comprises 2, 3, 4, 5, 6, 7, 8, or more subunits. In some embodiments, a multimeric accessory protein complex comprises a homo-meric or hetero-meric protein complex.

Optionally, a reaction mixture includes one or more additives for enhancing nucleotide incorporation, including betaine, DMSO, proline, trehalose, MMNO (4-methylmorpholine N-oxide) or a PEG-like compound.

In some embodiments, methods for nucleotide incorporation reactions can be conducted under conditions that are suitable for: binding a nucleotide to a polymerase (where the polymerase is bound to a duplex that includes a template molecule and primer); incorporating the nucleotide into the primer; generating at least one cleavage products from nucleotide incorporation; detecting one or more cleavage products, or one or any combination of these steps.

In some embodiments, suitable conditions include well known parameters, such as: time, temperature, pH, buffers, reagents, cations, salts, co-factors, nucleotides, nucleic acids, and enzymes. In some embodiments, a reagent or buffer can include a source of ions, such as KCl, K-acetate, $NH_4$-acetate, K-glutamate, $NH_4Cl$, or ammonium sulfate. In some embodiments, a reagent or buffer can include a source of divalent ions, such as $Mg^{2+}$ or $Mn^{2+}$, $MgCl_2$, $MnCl_2$, or Mg-acetate. In some embodiments, a reagent or buffer can include magnesium, manganese and/or calcium. In some embodiments, a buffer can include Tris, Tricine, HEPES, MOPS, ACES, MES, or inorganic buffers such as phosphate or acetate-based buffers which can provide a pH range of about 4-12. In some embodiments, a buffer can include chelating agents such as EDTA or EGTA. In some embodiments, a buffer can include dithiothreitol (DTT), glycerol, spermidine, and/or BSA (bovine serum albumin). In some embodiments, a buffer can include ATP.

In some embodiments, suitable conditions include conducting a nucleotide incorporation reaction in a liquid phase, including an aqueous fluid or immiscible fluid. In some embodiments, a nucleotide incorporation reaction can be conducted in a continuous aqueous phase, or in a hydrophilic phase of an emulsion having a discontinuous hydrophilic phase and a continuous hydrophobic phase. In some embodiments, an aqueous fluid can be water-based. In some embodiments, a hydrophobic phase can be oil-based. In some embodiments, different nucleotide incorporation reactions can be conducted in separate compartments (e.g., droplets) forming part of a hydrophilic phase of an emulsion having a discontinuous hydrophilic phase and a continuous hydrophobic phase.

In some embodiments, suitable conditions include conducting a nucleotide incorporation reaction with a polymerase enzyme and one or more nucleotides.

In some embodiments, suitable conditions include cyclical temperature changes, or essentially isothermal temperature conditions, or a combination of both. In some embodiments, a reaction can be conducted at a temperature range of about 0-10° C., or about 10-20° C., or about 20-30° C., or about 30-40° C., or about 40-50° C., or about 50-60° C., or about 60-70° C., or about 70-80° C., or about 80-90° C., or about 90-100° C., or high temperatures.

In some embodiments, suitable conditions include conducting a reaction for a time, such as about 10-30 seconds, or about 30-60 seconds, or about 1-3 minutes, or about 3-5 minutes, or about 5-6 minutes, or about 6-7 minutes, or about 7-8 minutes, or about 8-9 minutes, or about 9-10 minutes, or about 10-11 minutes, or about 11-12 minutes, or about 12-13 minutes, or about 13-14 minutes, or about 14-15 minutes, or about 15-20 minutes, or about 20-30 minutes, or about 30-45 minutes, or about 45-60 minutes, or about 1-3 hours, or about 3-6 hours, or about 6-10 hours, or longer.

In some embodiments, suitable conditions include conducting a reaction in a volume of about 1-10 uL, or about 10-25 uL, or about 25-50 uL, or about 50-75 uL, or about 75-100 uL, or about 100-125 uL, or about 125-150 uL, or about 150-200 uL, or more.

In some embodiments, suitable conditions include conducting a reaction in a tube or well. In some embodiments, the well can be a part of a 96-well plate.

In some embodiments, methods for nucleotide incorporation comprise one or more surfaces. In some embodiments, a surface can be attached with a plurality of first primers, the first primers of the plurality sharing a common first primer sequence. In some embodiments, a surface can be attached with a plurality of first and second primers, where the first and second primers have different sequences.

In some embodiments, a surface can be an outer or top-most layer or boundary of an object. In some embodiments, a surface can be interior to the boundary of an object.

In some embodiments, a surface can be porous, semi-porous or non-porous. In some embodiments, a surface can be a planar surface, as well as concave, convex, or any combination thereof. In some embodiments, a surface can be a bead, particle, microparticle, sphere, filter, flowcell, well, groove, channel reservoir, gel or inner wall of a capillary. In some embodiments, a surface includes the inner walls of a capillary, a channel, a well, groove, channel, reservoir. In some embodiments, a surface can include texture (e.g., etched, cavitated, pores, three-dimensional scaffolds or bumps).

In some embodiments, particles can have a shape that is spherical, hemispherical, cylindrical, barrel-shaped, toroidal, rod-like, disc-like, conical, triangular, cubical, polygonal, tubular, wire-like or irregular.

In some embodiments, a surface can be made from any material, including glass, polymers, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond).

In some embodiments, a surface can be magnetic or paramagnetic bead (e.g., magnetic or paramagnetic nanoparticles or microparticles). In some embodiments, paramagnetic microparticles can be paramagnetic beads attached with streptavidin (e.g., Dynabeads™ M-270 from Invitrogen, Carlsbad, Calif.). Particles can have an iron core, or comprise a hydrogel or agarose (e.g., Sepharose™).

In some embodiments, the surface can be attached with a plurality of a first primer. A surface can be coated with an acrylamide, carboxylic or amine compound for attaching a nucleic acid (e.g., a first primer). In some embodiments, an amino-modified nucleic acid (e.g., primer) can be attached to a surface that is coated with a carboxylic acid. In some embodiments, an amino-modified nucleic acid can be reacted with EDC (or EDAC) for attachment to a carboxylic acid coated surface (with or without NHS). A first primer can be immobilized to an acrylamide compound coating on a surface. Particles can be coated with an avidin-like compound (e.g., streptavidin) for binding biotinylated nucleic acids.

In some embodiments, the surface comprises the surface of a bead. In some embodiments, a bead comprises a polymer material. For example, a bead comprises a gel, hydrogel or acrylamide polymers. A bead can be porous. Particles can have cavitation or pores, or can include three-dimensional scaffolds. In some embodiments, particles can be Ion Sphere™ particles.

In some embodiments, the disclosed methods (as well as related compositions, systems and kits) include immobilizing one or more nucleic acid templates onto one or more supports. Nucleic acids may be immobilized on the solid support by any method including but not limited to physical adsorption, by ionic or covalent bond formation, or combinations thereof. A solid support may include a polymeric, a glass, or a metallic material. Examples of solid supports include a membrane, a planar surface, a microtiter plate, a bead, a filter, a test strip, a slide, a cover slip, and a test tube. A support includes any solid phase material upon which a oligomer is synthesized, attached, ligated or otherwise immobilized. A support can optionally comprise a "resin", "phase", "surface" and "support". A support may be composed of organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. A support can be shaped to comprise one or more wells, depressions or other containers, vessels, features or locations. A plurality of supports may be configured in an array at various locations. A support is optionally addressable (e.g., for robotic delivery of reagents), or by detection means including scanning by laser illumination and confocal or deflective light gathering. An amplification support (e.g., a bead) can be placed within or on another support (e.g., within a well of a second support).

In an embodiment the solid support is a "microparticle," "bead" "microbead", etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymehtymethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In certain embodiments of the invention a population of microparticles having different shapes sizes and/or colors can be used. The microparticles can optionally be encoded, e.g., with quantum dots such that each microparticle can be individually or uniquely identified.

In some embodiments, a bead surface can be functionalized for attaching a plurality of a first primer. In some embodiments, a bead can be any size that can fit into a reaction chamber. For example, one bead can fit in a reaction chamber. In some embodiments more than one bead can fit in a reaction chamber. In some embodiments, the smallest cross-sectional length of a bead (e.g., diameter) can be about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers).

In some embodiments, a bead can be attached with a plurality of one or more different primer sequences. In some embodiments, a bead can be attached with a plurality of one primer sequence, or can be attached a plurality of two or more different primer sequences. In some embodiments, a bead can be attached with a plurality of at least 1,000 primers, or about 1,000-10,000 primers, or about, 10,000-50,000 primers, or about 50,000-75,000 primers, or about 75,000-100,000 primers, or more.

In some embodiments, nucleotides can be compatible for use in any type of sequencing platform including chemical degradation, chain-termination, sequence-by-synthesis, pyrophosphate, massively parallel, ion-sensitive, and single molecule platforms.

In some embodiments, nucleotides can be used in any nucleic acid sequencing workflow, including sequencing by oligonucleotide probe ligation and detection (e.g., SOLiD™ from Life Technologies, WO 2006/084131), probe-anchor ligation sequencing (e.g., Complete Genomics™ or Polonator™), sequencing-by-synthesis (e.g., Genetic Analyzer and HiSeg™, from Illumina), pyrophosphate sequencing (e.g., Genome Sequencer FLX from 454 Life Sciences), ion-sensitive sequencing (e.g., Personal Genome Machine (PGM™) and Ion Proton™ Sequencer, both from Ion Torrent Systems, Inc.), and single molecule sequencing platforms (e.g., HeliScope™ from Helicos™).

In some embodiments, the disclosure relates generally to compositions, as well as related methods, systems, kits and apparatuses, for nucleotide incorporation reactions comprising nucleic acid sequencing methods that detect one or more byproducts of nucleotide incorporation. The detection of polymerase extension by detecting physicochemical byproducts of the extension reaction, can include polyphosphate, pyrophosphate, hydrogen ion, charge transfer, heat, and the like, as disclosed, for example, in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be flowed across the well, one at a time, under nucleotide incorporation conditions. The polymerase incorporates the appropriate nucleotide into the growing strand, and the hydrogen ion that is released can change the pH in the solution, which can be detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Ion Torrent™ Systems, Life Technologies Corporation).

In some embodiments, target polynucleotides produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with, operatively coupled, or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 μm³ (i.e., 1 pL) in volume. In some embodiments each reaction chamber is no greater than 0.34 pL, 0.096 pL or even 0.012 pL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^9$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 2010/0301398; U.S. Patent Publication No. 2010/0300895; U.S. Patent Publication No. 2010/0300559 (now U.S. Pat. No. 8,546,128); U.S. Patent Publication No. 2010/0197507 (now U.S. Pat. No. 8,306,757); U.S. Patent Publication No. 2010/0137143; U.S. Patent Publication No. 2009/0127589 (now U.S. Pat. No. 7,948,015); and U.S. Patent Publication No. 2009/0026082 (now U.S. Pat. No. 8,262,900), which are incorporated by reference in their entireties.

In one aspect, the disclosed compositions, methods, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of phosphatase or pyrophosphatase). Examples of such ion-based nucleic acid sequencing methods and platforms include the Ion Torrent PGM™ or Proton™ sequencer (Ion Torrent™ Systems, Life Technologies Corporation).

In some embodiments, the present teachings provide nucleotides employed in a nucleic acid sequencing method. In one exemplary embodiment, the disclosure relates generally to a method for obtaining sequence information from template polynucleotides, comprising: performing template-dependent nucleic acid synthesis using any one, or a combination of any, of the nucleotides described herein.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In some embodiments, the disclosure relates generally to a method for sequencing a nucleic acid, comprising: (a) disposing template polynucleotides into a plurality of reaction chambers, wherein one or more of the reaction chambers are in contact with at least one field effect transistor (FET). Optionally, the method further includes contacting template polynucleotides, which are disposed into one of the reaction chambers, with a polymerase thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ or Proton™ sequencer can be found, for example, in U.S. Patent Publication No. 2009/0026082 (now U.S. Pat. No. 8,262,900); U.S. Patent Publication No. 2010/0137143; and U.S. Patent Publication No. 2010/0282617 (now U.S. Pat. No. 8,349,167), all of which applications are incorporated by reference herein in their entireties.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of nucleotide addition (which may be referred to herein as "nucleotide flows" from which nucleotide incorporations may result) and washing. The primer may be annealed to the sample or template so that the primer's 3' end can be extended by a polymerase whenever nucleotides complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a chemical sensor can be determined.

In a typical embodiment of ion-based nucleic acid sequencing, nucleotide incorporations can be detected by detecting the presence and/or concentration of hydrogen ions generated by polymerase-catalyzed extension reactions. In one embodiment, templates, optionally pre-bound to a sequencing primer and/or a polymerase, can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as particles, bead, or the like, and said clonal populations are loaded into reaction chambers.

In another embodiment, the templates, optionally bound to a polymerase, are distributed, deposited or positioned to different sites of the array. The sites of the array include primers and the methods can include hybridizing different templates to the primers within different sites.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed according to the user protocols supplied with the PGM™ or Proton™ sequencer. Example 3 provides one exemplary protocol for ion-based sequencing using the Ion Torrent PGM™ sequencer (Ion Torrent™ Systems, Life Technologies, CA).

In some embodiments, the disclosure relates generally to methods for sequencing a population of template polynucleotides, comprising: (a) generating a plurality of amplicons by clonally amplifying a plurality of template polynucleotides onto a plurality of surfaces, wherein the amplifying is performed within a single continuous phase of a reaction mixture and wherein at least 10%, 20%, 30%, 40%, 50%, 60%, 70%, 80%, 90%, or 95% of the resulting amplicons are substantially monoclonal in nature. In some embodiments, a sufficient number of substantially monoclonal amplicons are produced in a single amplification reaction to generate at least 100 MB, 200 MB, 300 MB, 400 MB, 500 MB, 750 MB, 1 GB or 2 GB of AQ20 sequencing reads on an Ion Torrent PGM™ 314, 316 or 318 sequencer. The term "AQ20 and its variants, as used herein, refers to a particular method of measuring sequencing accuracy in the Ion Torrent PGM™ sequencer. Accuracy can be measured in terms of the Phred-like Q score, which measures accuracy on logarithmic scale that: Q10=90%, Q20=99%, Q30=99.9%, Q40=99.99%, and Q50=99.999%. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: Q10=90%, Q17=98%, Q20=99%, Q30=99.9%, Q40=99.99%, and Q50=99.999%. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

Embodiments of the present teachings can be further understood in light of the following examples, which should not be construed as limiting the scope of the present teachings in any way.

EXAMPLE 1

Polymerase Incorporation of γ-S-TTP:effect of alkaline phosphatase pre-treatment:

This experiment was conducted to demonstrate that γ-S-TTP is resistant to degradation by calf intestinal phosphatase.

Two solutions were prepared as follows in 20 mM Tris HCl, pH 7.5, 20 mM NaCl, 10 mM MgCl$_2$: (A) 80 μM of TTP, and (B) 200 μM of γ-S-TTP.

To both solution was added 1.5 μL of 10 u/μL of calf intestinal phosphatase (CIP), and the solutions were incubated at 37° C. for 20 min. The phosphatase was then removed by passing the solutions through a 10,000 molecular weight cut-off ultrafiltration membrane. The resulting solutions were then used for the polymerase extension reactions.

For the polymerase extension assays, a fluorescein-labeled oligonucleotide substrate was designed, and used in an assay to detect nucleotide incorporation. The labeled oligonucleotide is a hairpin-type oligonucleotide with a T-fluorescein residue located at the third position from the 3' end. The 5' end of the labeled oligonucleotide is a single stranded sequence 3'-AGGGGGG-5'. Thus, the first nucleotide to be inserted by a polymerase onto the 3' end of the substrate is a TTP. The 5' and 3' ends of the hairpin oligonucleotide is shown below. A fluorescein is attached to the T residue, which is underlined and bolded:

```
                                          (SEQ ID NO: 83)
      .....TGC 3'
      ......ACGAGGGGGG 5'
```

Without wishing to be bound by theory, it is postulated that when the third base from the 3' end is labeled with a fluorphore (in this case the labeled nucleotide is a T), and when the 3' terminal base is a cytosine or guanosine, then the fluorphore is in a stacked position with the 3' terminal base, resulting in quenching the fluorescence from the fluorphore. When a thymidine is incorporated at the terminal 3' end (e.g., via polymerase-mediated nucleotide incorporation), the fluorphore is un-quenched. This assay can be performed with the hairpin molecule described herein, or with two annealed single-strands that mimic the linear ends of this hairpin molecule.

A solution was prepared in the same buffer as above containing 250 nM of the hairpin oligonucleotide, 16 μM of a short oligonucleotide (5'-CCCCCC-3', acting as a signal amplifier), and 2 nM of Bst polymerase. Then 50 μL aliquots of this solution were placed in individual wells of a microtiter plate. In separate wells of the same plate were placed 50 μL aliquots of the CIP-treated solutions from above, as well as identical solutions that had not been treated with CIP. The plate was equilibrated at 37° C. in a fluorescence microplate reader, and then the dNTP solutions were mixed with the solutions of polymerase and fluorogenic hairpin oligonucleotide. The polymerase catalyzed incorporation reactions were followed by recording the fluorescence intensity changes using 490 nm for excitation and 525 nm for the emission. When a polymerase reaction occurred, an increase in the fluorescence intensity over time was detected (see FIG. 4). There was no change in fluorescence when no nucleotide incorporation reaction occurred (see FIG. 4).

FIG. 4 shows that no incorporation reaction takes place with a CIP-treated TTP. On the other hand when a γ-S-TTP was used, polymerase reactions can be detected with both CIP treated and non-treated solutions. This demonstrates that the γ-S-TTP is resistant to the alkaline phosphatase activity. A treatment of synthetically prepared γ-S-TTP with CIP can be used to remove any traces of contaminating dTTP that may be present in the preparation of γ-S-TTP.

TABLE 1

Some Typical pKa Values For Free Amino Acids In Solution

| Amino Acid | α-carboxylic acid | α-amino | Side chain |
|---|---|---|---|
| Alanine | 2.35 | 9.87 | |
| Arginine | 2.01 | 9.04 | 12.48 |
| Asparagine | 2.02 | 8.80 | |
| Aspartic Acid | 2.10 | 9.82 | 3.86 |
| Cysteine | 2.05 | 10.25 | 8.00 |
| Glutamic Acid | 2.10 | 9.47 | 4.07 |
| Glutamine | 2.17 | 9.13 | |
| Glycine | 2.35 | 9.78 | |
| Histidine | 1.77 | 9.18 | 6.10 |
| Isoleucine | 2.32 | 9.76 | |
| Leucine | 2.33 | 9.74 | |
| Lysine | 2.18 | 8.95 | 10.53 |
| Methionine | 2.28 | 9.21 | |
| Phenylalanine | 2.58 | 9.24 | |
| Proline | 2.00 | 10.60 | |
| Serine | 2.21 | 9.15 | |
| Threonine | 2.09 | 9.10 | |
| Tryptophan | 2.38 | 9.39 | |
| Tyrosine | 2.20 | 9.11 | 10.07 |
| Valine | 2.29 | 9.72 | |

TABLE 2

Candidate amino acid residues for modification in Bst DNA polymerase (including pKa values for amino acid residues calculated using PropKa)

| Amino Acid Residue | pKa | |
|---|---|---|
| GLU-277 | 4.64 | |
| GLU-372 | 4.7 | |
| GLU-15 | 4.71 | |
| GLU-206 | 4.71 | |
| GLU-426 | 4.71 | |
| GLU-493 | 4.71 | |
| GLU-456 | 4.76 | |
| GLU-131 | 4.78 | |
| GLU-349 | 4.78 | |
| GLU-446 | 4.85 | |
| GLU-522 | 4.85 | |
| GLU-558 | 4.85 | |
| GLU-26 | 4.92 | |
| GLU-294 | 4.92 | |
| GLU-363 | 5.08 | |
| HIS-534 | 5.12 | |
| HIS-572 | 6.17 | S |
| HIS-473 | 6.29 | B |
| HIS-46 | 6.43 | S |
| HIS-273 | 6.51 | S |
| LYS-510 | 7.29 | B |
| N+ | 7.86 | S |
| TYR-477 | 7.98 | B |
| LYS-73 | 8.55 | |
| CYS-550 | 8.87 | |
| CYS-93 | 9.57 | |

TABLE 3

Candidate amino acid residues for modification in Bst DNA polymerase (including pKa values for amino acid residues calculated using H++)

| Amino Acid Residue | pKa | |
|---|---|---|
| GLU-461 | 4.533 | |
| GLU-206 | 4.555 | |
| ASP-113 | 4.57 | |
| HIS-273 | 4.662 | |
| HIS-534 | 4.747 | |
| GLU-277 | 4.806 | |
| GLU-456 | 4.902 | |
| GLU-544 | 4.972 | |
| GLU-54 | 5.037 | |
| GLU-30 | 5.149 | |
| GLU-349 | 5.158 | |
| GLU-522 | 5.221 | |
| HIS-151 | 5.26 | |
| GLU-558 | 5.361 | |
| GLU-220 | 5.423 | |
| GLU-446 | 5.911 | S |
| NTA | 6.465 | S |
| HIS-46 | 7.653 | S |
| HIS-572 | 8.056 | S |
| HIS-308 | 8.333 | |
| HIS-473 | 8.397 | |
| LYS-411 | 9.494 | |
| LYS-543 | 9.72 | |
| LYS-287 | 9.815 | |
| TYR-419 | 10.041 | |
| LYS-253 | 10.077 | |

TABLE 4

Candidate amino acids for modification in E. coli SSB

| Amino Acid Residue | pKa |
|---|---|
| HIS-55 | 3.968 |
| ASP-90 | 4.251 |
| ASP-17 | 4.298 |
| ASP-42 | 4.449 |
| GLU-50 | 4.738 |
| GLU-65 | 4.856 |
| GLU-47 | 4.878 |
| GLU-19 | 4.896 |
| GLU-53 | 5.046 |
| ASP-95 | 5.143 |
| GLU-69 | 5.214 |
| GLU-38 | 5.606 |
| NTALA-1 | 5.851 |
| GLU-80 | 5.898 |
| LYS-7 | 7.276 |
| LYS-49 | 8.791 |
| GLU-100 | 9.033 |
| ARG-3 | 9.069 |
| LYS-87 | 9.453 |
| LYS-62 | 9.754 |
| LYS-43 | 10.399 |
| TYR-22 | 10.427 |
| TYR-97 | 10.483 |
| TYR-70 | 10.619 |
| LYS-73 | 10.898 |
| ARG-56 | 11.169 |
| ARG-96 | 11.176 |
| ARG-86 | 11.257 |
| ARG-84 | 11.296 |
| ARG-41 | 11.381 |
| ARG-115 | 11.804 |
| ARG-21 | 12.035 |
| ARG-72 | 12.671 |
| TYR-78 | 16.412 |

TABLE 5

Candidate amino acids for substitution in Therminator™ DNA polymerase

| Amino Acid Residue | pKa (calc) | pKa (model) |
|---|---|---|
| ASP 4 | 7.85 | |
| ASP 6 | 5.95 | |
| ASP 31 | 2.11 | |
| ASP 44 | 2.53 | |
| ASP 45 | 3.60 | |
| ASP 50 | 2.82 | |
| ASP 92 | 4.14 | |
| ASP 98 | 3.43 | |
| ASP 108 | 4.05 | 3.80 |
| ASP 113 | 3.10 | 3.80 |
| ASP 123 | 4.09 | 3.80 |
| ASP 132 | 3.64 | 3.80 |
| ASP 164 | 1.56 | 3.80 |
| ASP 177 | 3.87 | 3.80 |
| ASP 182 | 3.79 | 3.80 |
| ASP 202 | 3.47 | 3.80 |
| ASP 204 | 2.82 | 3.80 |
| ASP 212 | 2.14 | 3.80 |
| ASP 215 | 7.23 | 3.80 |
| ASP 235 | 2.59 | 3.80 |
| ASP 246 | 3.29 | 3.80 |
| ASP 259 | 6.50 | 3.80 |
| ASP 315 | 5.97 | 3.80 |
| ASP 343 | 3.69 | 3.80 |
| ASP 373 | 3.18 | 3.80 |
| ASP 398 | 4.52 | 3.80 |
| ASP 404 | 6.10 | 3.80 |
| ASP 421 | 4.42 | 3.80 |
| ASP 432 | 2.60 | 3.80 |
| ASP 444 | 3.20 | 3.80 |
| ASP 455 | 3.97 | 3.80 |
| ASP 472 | 3.03 | 3.80 |
| ASP 480 | 3.21 | 3.80 |
| ASP 540 | 3.92 | 3.80 |
| ASP 542 | 4.89 | 3.80 |
| ASP 552 | 2.69 | 3.80 |
| ASP 598 | 3.40 | 3.80 |
| ASP 614 | 3.89 | 3.80 |
| ASP 635 | 2.78 | 3.80 |
| ASP 712 | 3.83 | 3.80 |
| ASP 718 | 3.80 | 3.80 |
| GLU 10 | 4.05 | 4.50 |
| GLU 22 | 4.12 | 4.50 |
| GLU 25 | 3.60 | 4.50 |
| GLU 29 | 4.26 | 4.50 |
| GLU 35 | 2.57 | 4.50 |
| GLU 49 | 3.85 | 4.50 |
| GLU 69 | 4.56 | 4.50 |
| GLU 81 | 4.38 | 4.50 |
| GLU 111 | 4.60 | 4.50 |
| GLU 130 | 4.51 | 4.50 |
| GLU 133 | 3.91 | 4.50 |
| GLU 134 | 4.91 | 4.50 |
| GLU 148 | 5.27 | 4.50 |
| GLU 150 | 5.08 | 4.50 |
| GLU 151 | 4.10 | 4.50 |
| GLU 167 | 4.42 | 4.50 |
| GLU 187 | 4.70 | 4.50 |
| GLU 189 | 3.57 | 4.50 |
| GLU 200 | 4.18 | 4.50 |
| GLU 224 | 4.29 | 4.50 |
| GLU 225 | 4.55 | 4.50 |
| GLU 238 | 4.49 | 4.50 |
| GLU 251 | 4.60 | 4.50 |
| GLU 276 | 4.43 | 4.50 |
| GLU 280 | 4.75 | 4.50 |
| GLU 288 | 3.94 | 4.50 |
| GLU 293 | 4.71 | 4.50 |
| GLU 294 | 3.67 | 4.50 |
| GLU 300 | 4.26 | 4.50 |
| GLU 303 | 4.59 | 4.50 |
| GLU 306 | 4.72 | 4.50 |
| GLU 314 | 5.00 | 4.50 |
| GLU 321 | 4.64 | 4.50 |
| GLU 325 | 4.87 | 4.50 |
| GLU 330 | 7.31 | 4.50 |
| GLU 354 | 5.67 | 4.50 |
| GLU 366 | 6.07 | 4.50 |
| GLU 374 | 4.64 | 4.50 |
| GLU 376 | 3.89 | 4.50 |
| GLU 391 | 4.65 | 4.50 |
| GLU 393 | 3.42 | 4.50 |
| GLU 426 | 4.46 | 4.50 |
| GLU 430 | 4.75 | 4.50 |
| GLU 436 | 4.54 | 4.50 |
| GLU 458 | 4.49 | 4.50 |
| GLU 459 | 3.84 | 4.50 |
| GLU 475 | 4.11 | 4.50 |
| GLU 508 | 4.65 | 4.50 |
| GLU 511 | 3.78 | 4.50 |
| GLU 519 | 4.91 | 4.50 |
| GLU 522 | 4.09 | 4.50 |
| GLU 527 | 2.97 | 4.50 |
| GLU 529 | 4.67 | 4.50 |
| GLU 530 | 4.53 | 4.50 |
| GLU 554 | 4.84 | 4.50 |
| GLU 562 | 4.46 | 4.50 |
| GLU 576 | 5.03 | 4.50 |
| GLU 578 | 3.64 | 4.50 |
| GLU 580 | 4.99 | 4.50 |
| GLU 599 | 5.35 | 4.50 |
| GLU 600 | 6.04 | 4.50 |
| GLU 609 | 5.62 | 4.50 |
| GLU 617 | 4.45 | 4.50 |
| GLU 621 | 4.96 | 4.50 |
| GLU 628 | 4.02 | 4.50 |
| GLU 637 | 5.22 | 4.50 |
| GLU 638 | 4.75 | 4.50 |
| GLU 645 | 4.50 | 4.50 |
| GLU 664 | 4.36 | 4.50 |
| GLU 719 | 4.28 | 4.50 |
| GLU 730 | 4.72 | 4.50 |
| GLU 734 | 4.98 | 4.50 |
| GLU 742 | 3.65 | 4.50 |
| C- 750 | 3.25 | 3.20 |
| HIS 59 | 6.13 | 6.50 |
| HIS 89 | 4.69 | 6.50 |
| HIS 103 | 7.00 | 6.50 |
| HIS 147 | 7.17 | 6.50 |
| HIS 257 | 4.01 | 6.50 |
| HIS 416 | 5.54 | 6.50 |
| HIS 439 | 6.77 | 6.50 |
| HIS 545 | 2.90 | 6.50 |
| HIS 633 | 6.96 | 6.50 |
| HIS 663 | 5.84 | 6.50 |
| HIS 679 | 6.64 | 6.50 |
| CYS 223 | 11.84 | 9.00 |
| CYS 428 | 99.99 | 99.99 |
| CYS 442 | 99.99 | 99.99 |
| CYS 506 | 99.99 | 99.99 |
| CYS 509 | 99.99 | 99.99 |
| TYR 7 | 10.59 | 10.00 |
| TYR 30 | 10.26 | 10.00 |
| TYR 37 | 17.23 | 10.00 |
| TYR 39 | 14.20 | 10.00 |
| TYR 86 | 10.20 | 10.00 |
| TYR 110 | 11.95 | 10.00 |
| TYR 112 | 10.49 | 10.00 |
| TYR 120 | 13.12 | 10.00 |
| TYR 146 | 11.21 | 10.00 |
| TYR 162 | 11.82 | 10.00 |
| TYR 180 | 11.47 | 10.00 |
| TYR 209 | 13.47 | 10.00 |
| TYR 218 | 11.91 | 10.00 |
| TYR 261 | 10.23 | 10.00 |
| TYR 273 | 9.77 | 10.00 |

TABLE 5-continued

Candidate amino acids for substitution in Therminator ™ DNA polymerase

| Amino Acid Residue | pKa (calc) | pKa (model) |
|---|---|---|
| TYR 279 | 11.96 | 10.00 |
| TYR 291 | 10.52 | 10.00 |
| TYR 311 | 14.21 | 10.00 |
| TYR 320 | 10.89 | 10.00 |
| TYR 362 | 11.49 | 10.00 |
| TYR 384 | 11.17 | 10.00 |
| TYR 388 | 12.23 | 10.00 |
| TYR 402 | 14.32 | 10.00 |
| TYR 409 | 14.74 | 10.00 |
| TYR 431 | 10.05 | 10.00 |
| TYR 481 | 10.52 | 10.00 |
| TYR 494 | 12.59 | 10.00 |
| TYR 496 | 16.00 | 10.00 |
| TYR 497 | 14.40 | 10.00 |
| TYR 499 | 11.49 | 10.00 |
| TYR 505 | 11.27 | 10.00 |
| TYR 520 | 11.38 | 10.00 |
| TYR 538 | 13.52 | 10.00 |
| TYR 566 | 11.47 | 10.00 |
| TYR 579 | 11.62 | 10.00 |
| TYR 583 | 11.55 | 10.00 |
| TYR 594 | 12.23 | 10.00 |
| TYR 701 | 14.24 | 10.00 |
| TYR 731 | 10.99 | 10.00 |
| TYR 732 | 11.88 | 10.00 |
| TYR 750 | 10.81 | 10.00 |
| LYS 13 | 10.18 | 10.50 |
| LYS 20 | 11.10 | 10.50 |
| LYS 21 | 10.56 | 10.50 |
| LYS 27 | 11.24 | 10.50 |
| LYS 43 | 10.25 | 10.50 |
| LYS 52 | 11.08 | 10.50 |
| LYS 53 | 10.63 | 10.50 |
| LYS 57 | 10.28 | 10.50 |
| LYS 64 | 10.26 | 10.50 |
| LYS 66 | 10.51 | 10.50 |
| LYS 70 | 11.41 | 10.50 |
| LYS 73 | 9.02 | 10.50 |
| LYS 74 | 10.47 | 10.50 |
| LYS 84 | 10.64 | 10.50 |
| LYS 118 | 10.50 | 10.50 |
| LYS 124 | 10.20 | 10.50 |
| LYS 174 | 10.01 | 10.50 |
| LYS 175 | 10.42 | 10.50 |
| LYS 188 | 10.15 | 10.50 |
| LYS 192 | 11.36 | 10.50 |
| LYS 201 | 12.01 | 10.50 |
| LYS 220 | 10.65 | 10.50 |
| LYS 221 | 10.80 | 10.50 |
| LYS 229 | 10.54 | 10.50 |
| LYS 240 | 10.09 | 10.50 |
| LYS 253 | 11.39 | 10.50 |
| LYS 285 | 10.22 | 10.50 |
| LYS 287 | 11.74 | 10.50 |
| LYS 289 | 9.16 | 10.50 |
| LYS 317 | 10.31 | 10.50 |
| LYS 360 | 8.91 | 10.50 |
| LYS 363 | 10.27 | 10.50 |
| LYS 371 | 9.91 | 10.50 |
| LYS 390 | 10.38 | 10.50 |
| LYS 429 | 10.64 | 10.50 |
| LYS 440 | 10.41 | 10.50 |
| LYS 443 | 10.92 | 10.50 |
| LYS 462 | 11.52 | 10.50 |
| LYS 464 | 8.83 | 10.50 |
| LYS 466 | 10.69 | 10.50 |
| LYS 468 | 10.07 | 10.50 |
| LYS 476 | 10.26 | 10.50 |
| LYS 477 | 10.91 | 10.50 |
| LYS 487 | 10.75 | 10.50 |
| LYS 501 | 10.22 | 10.50 |
| LYS 507 | 10.64 | 10.50 |
| LYS 531 | 11.77 | 10.50 |
| LYS 535 | 10.87 | 10.50 |
| LYS 557 | 10.51 | 10.50 |
| LYS 558 | 10.76 | 10.50 |
| LYS 559 | 10.31 | 10.50 |
| LYS 561 | 10.04 | 10.50 |
| LYS 565 | 10.25 | 10.50 |
| LYS 591 | 10.45 | 10.50 |
| LYS 592 | 10.20 | 10.50 |
| LYS 593 | 9.74 | 10.50 |
| LYS 602 | 10.54 | 10.50 |
| LYS 620 | 10.49 | 10.50 |
| LYS 632 | 10.36 | 10.50 |
| LYS 644 | 10.24 | 10.50 |
| LYS 684 | 10.40 | 10.50 |
| LYS 692 | 10.25 | 10.50 |
| LYS 705 | 9.57 | 10.50 |
| LYS 746 | 11.49 | 10.50 |
| ARG 17 | 12.25 | 12.50 |
| ARG 32 | 13.03 | 12.50 |
| ARG 58 | 12.29 | 12.50 |
| ARG 67 | 14.10 | 12.50 |
| ARG 78 | 12.36 | 12.50 |
| ARG 97 | 11.98 | 12.50 |
| ARG 99 | 12.16 | 12.50 |
| ARG 101 | 14.07 | 12.50 |
| ARG 119 | 16.80 | 12.50 |
| ARG 169 | 13.55 | 12.50 |
| ARG 193 | 12.78 | 12.50 |
| ARG 196 | 12.44 | 12.50 |
| ARG 199 | 12.34 | 12.50 |
| ARG 222 | 13.63 | 12.50 |
| ARG 234 | 12.80 | 12.50 |
| ARG 243 | 12.36 | 12.50 |
| ARG 247 | 12.27 | 12.50 |
| ARG 255 | 10.00 | 12.50 |
| ARG 265 | 13.14 | 12.50 |
| ARG 266 | 11.19 | 12.50 |
| ARG 307 | 12.83 | 12.50 |
| ARG 310 | 13.21 | 12.50 |
| ARG 324 | 12.66 | 12.50 |
| ARG 335 | 12.16 | 12.50 |
| ARG 346 | 13.10 | 12.50 |
| ARG 359 | 10.29 | 12.50 |
| ARG 364 | 11.85 | 12.50 |
| ARG 375 | 12.65 | 12.50 |
| ARG 379 | 12.22 | 12.50 |
| ARG 380 | 12.33 | 12.50 |
| ARG 381 | 12.44 | 12.50 |
| ARG 394 | 12.45 | 12.50 |
| ARG 406 | 12.99 | 12.50 |
| ARG 425 | 11.45 | 12.50 |
| ARG 460 | 11.44 | 12.50 |
| ARG 465 | 12.42 | 12.50 |
| ARG 482 | 10.68 | 12.50 |
| ARG 484 | 12.31 | 12.50 |
| ARG 503 | 13.11 | 12.50 |
| ARG 518 | 13.62 | 12.50 |
| ARG 526 | 12.48 | 12.50 |
| ARG 585 | 12.11 | 12.50 |
| ARG 606 | 13.59 | 12.50 |
| ARG 612 | 12.73 | 12.50 |
| ARG 613 | 12.46 | 12.50 |
| ARG 625 | 12.48 | 12.50 |
| ARG 641 | 12.85 | 12.50 |
| ARG 685 | 13.07 | 12.50 |
| ARG 689 | 13.04 | 12.50 |
| ARG 694 | 12.46 | 12.50 |
| ARG 713 | 12.20 | 12.50 |
| ARG 743 | 12.30 | 12.50 |
| N+ 1 | 7.38 | 8.00 |

TABLE 6

Candidate amino acids for substitution in KOD DNA polymerase

| Amino Acid Residue | pKa (calc) | pKa (model) |
|---|---|---|
| ASP 4 | 7.06 | 3.80 |
| ASP 6 | −1.72 | 3.80 |
| ASP 11 | 3.94 | 3.80 |
| ASP 31 | 1.79 | 3.80 |
| ASP 44 | 3.94 | 3.80 |
| ASP 45 | 2.58 | 3.80 |
| ASP 92 | 2.18 | 3.80 |
| ASP 98 | 3.41 | 3.80 |
| ASP 108 | 3.11 | 3.80 |
| ASP 113 | −0.42 | 3.80 |
| ASP 123 | 1.89 | 3.80 |
| ASP 132 | 3.23 | 3.80 |
| ASP 141 | 15.80 | 3.80 |
| ASP 164 | 3.36 | 3.80 |
| ASP 177 | 3.87 | 3.80 |
| ASP 182 | 3.31 | 3.80 |
| ASP 202 | −1.29 | 3.80 |
| ASP 204 | 1.17 | 3.80 |
| ASP 212 | −3.07 | 3.80 |
| ASP 215 | 4.76 | 3.80 |
| ASP 235 | −0.47 | 3.80 |
| ASP 246 | 4.01 | 3.80 |
| ASP 259 | 4.82 | 3.80 |
| ASP 315 | 3.17 | 3.80 |
| ASP 343 | 3.50 | 3.80 |
| ASP 373 | 2.82 | 3.80 |
| ASP 404 | 3.03 | 3.80 |
| ASP 421 | 3.55 | 3.80 |
| ASP 432 | 3.68 | 3.80 |
| ASP 444 | 3.15 | 3.80 |
| ASP 455 | 3.74 | 3.80 |
| ASP 472 | 2.98 | 3.80 |
| ASP 480 | 3.62 | 3.80 |
| ASP 540 | 3.09 | 3.80 |
| ASP 542 | 8.78 | 3.80 |
| ASP 552 | 3.53 | 3.80 |
| ASP 598 | 3.43 | 3.80 |
| ASP 614 | −1.00 | 3.80 |
| ASP 633 | 3.59 | 3.80 |
| ASP 635 | 3.18 | 3.80 |
| ASP 718 | −2.60 | 3.80 |
| ASP 721 | −4.20 | 3.80 |
| ASP 728 | −5.80 | 3.80 |
| ASP 754 | −7.40 | 3.80 |
| GLU 10 | 4.03 | 4.50 |
| GLU 22 | 3.47 | 4.50 |
| GLU 25 | 4.06 | 4.50 |
| GLU 29 | 3.91 | 4.50 |
| GLU 35 | 3.43 | 4.50 |
| GLU 49 | 3.79 | 4.50 |
| GLU 50 | 4.50 | 4.50 |
| GLU 57 | 4.71 | 4.50 |
| GLU 69 | 3.54 | 4.50 |
| GLU 81 | 3.98 | 4.50 |
| GLU 102 | 4.78 | 4.50 |
| GLU 111 | 2.22 | 4.50 |
| GLU 130 | 4.78 | 4.50 |
| GLU 133 | 4.36 | 4.50 |
| GLU 134 | 4.50 | 4.50 |
| GLU 143 | 9.42 | 4.50 |
| GLU 148 | 4.64 | 4.50 |
| GLU 150 | 5.76 | 4.50 |
| GLU 151 | 15.70 | 4.50 |
| GLU 154 | 4.10 | 4.50 |
| GLU 165 | 3.26 | 4.50 |
| GLU 166 | 4.35 | 4.50 |
| GLU 187 | 0.05 | 4.50 |
| GLU 189 | 4.21 | 4.50 |
| GLU 200 | 4.43 | 4.50 |
| GLU 224 | 4.64 | 4.50 |
| GLU 238 | 3.49 | 4.50 |
| GLU 251 | 4.31 | 4.50 |
| GLU 276 | 0.56 | 4.50 |
| GLU 280 | 4.78 | 4.50 |
| GLU 288 | 4.61 | 4.50 |
| GLU 293 | 4.50 | 4.50 |
| GLU 294 | 3.98 | 4.50 |
| GLU 300 | 4.85 | 4.50 |
| GLU 303 | 4.57 | 4.50 |
| GLU 306 | 4.69 | 4.50 |
| GLU 314 | 3.66 | 4.50 |
| GLU 321 | 3.37 | 4.50 |
| GLU 325 | 4.50 | 4.50 |
| GLU 330 | 6.95 | 4.50 |
| GLU 354 | 3.49 | 4.50 |
| GLU 363 | 1.46 | 4.50 |
| GLU 366 | 4.66 | 4.50 |
| GLU 374 | 4.36 | 4.50 |
| GLU 376 | 3.83 | 4.50 |
| GLU 385 | 4.50 | 4.50 |
| GLU 391 | 4.64 | 4.50 |
| GLU 393 | 3.84 | 4.50 |
| GLU 398 | 3.91 | 4.50 |
| GLU 426 | 2.90 | 4.50 |
| GLU 430 | 4.57 | 4.50 |
| GLU 458 | 4.50 | 4.50 |
| GLU 459 | 4.53 | 4.50 |
| GLU 475 | 4.54 | 4.50 |
| GLU 508 | 3.90 | 4.50 |
| GLU 511 | 4.19 | 4.50 |
| GLU 519 | 4.57 | 4.50 |
| GLU 527 | 4.04 | 4.50 |
| GLU 529 | 3.93 | 4.50 |
| GLU 530 | 4.05 | 4.50 |
| GLU 554 | 4.60 | 4.50 |
| GLU 562 | 4.64 | 4.50 |
| GLU 576 | 4.47 | 4.50 |
| GLU 578 | 5.53 | 4.50 |
| GLU 580 | 4.12 | 4.50 |
| GLU 599 | 4.05 | 4.50 |
| GLU 600 | 4.64 | 4.50 |
| GLU 609 | 14.10 | 4.50 |
| GLU 617 | 12.50 | 4.50 |
| GLU 621 | 10.90 | 4.50 |
| GLU 628 | 4.47 | 4.50 |
| GLU 637 | 4.50 | 4.50 |
| GLU 645 | 4.50 | 4.50 |
| GLU 648 | 4.50 | 4.50 |
| GLU 654 | 4.50 | 4.50 |
| GLU 658 | 3.94 | 4.50 |
| GLU 664 | 9.30 | 4.50 |
| GLU 719 | 7.70 | 4.50 |
| GLU 730 | 6.10 | 4.50 |
| GLU 734 | 4.50 | 4.50 |
| GLU 742 | 2.90 | 4.50 |
| GLU 753 | 1.30 | 4.50 |
| HIS 59 | 6.43 | 6.50 |
| HIS 89 | 4.54 | 6.50 |
| HIS 103 | 6.15 | 6.50 |
| HIS 147 | 6.36 | 6.50 |
| HIS 257 | 4.00 | 6.50 |
| HIS 416 | 2.74 | 6.50 |
| HIS 439 | 7.09 | 6.50 |
| HIS 663 | 6.50 | 6.50 |
| HIS 679 | 6.50 | 6.50 |
| HIS 725 | 6.50 | 6.50 |
| CYS 223 | 10.07 | 9.00 |
| CYS 428 | 99.99 | 9.00 |
| CYS 442 | 99.99 | 9.00 |
| CYS 506 | 6.50 | 9.00 |
| CYS 509 | 16.78 | 9.00 |
| TYR 7 | 10.67 | 10.00 |
| TYR 30 | 10.00 | 10.00 |
| TYR 37 | 17.98 | 10.00 |
| TYR 39 | 12.92 | 10.00 |
| TYR 86 | 13.65 | 10.00 |
| TYR 110 | 12.67 | 10.00 |
| TYR 112 | 10.84 | 10.00 |

TABLE 6-continued

Candidate amino acids for substitution in KOD DNA polymerase

| Amino Acid Residue | pKa (calc) | pKa (model) |
|---|---|---|
| TYR 120 | 13.53 | 10.00 |
| TYR 146 | 10.06 | 10.00 |
| TYR 162 | 10.41 | 10.00 |
| TYR 180 | 10.00 | 10.00 |
| TYR 209 | 11.28 | 10.00 |
| TYR 218 | 7.75 | 10.00 |
| TYR 261 | 9.34 | 10.00 |
| TYR 273 | 9.22 | 10.00 |
| TYR 279 | 13.15 | 10.00 |
| TYR 291 | 10.00 | 10.00 |
| TYR 311 | 16.84 | 10.00 |
| TYR 320 | 14.28 | 10.00 |
| TYR 362 | 12.68 | 10.00 |
| TYR 384 | 10.00 | 10.00 |
| TYR 388 | 10.00 | 10.00 |
| TYR 402 | 17.93 | 10.00 |
| TYR 409 | 12.25 | 10.00 |
| TYR 431 | 9.81 | 10.00 |
| TYR 481 | 11.76 | 10.00 |
| TYR 493 | 12.60 | 10.00 |
| TYR 494 | 9.46 | 10.00 |
| TYR 496 | 14.11 | 10.00 |
| TYR 497 | 15.66 | 10.00 |
| TYR 499 | 9.84 | 10.00 |
| TYR 505 | 8.20 | 10.00 |
| TYR 520 | 11.19 | 10.00 |
| TYR 532 | 11.04 | 10.00 |
| TYR 538 | 12.70 | 10.00 |
| TYR 566 | 13.34 | 10.00 |
| TYR 579 | 10.65 | 10.00 |
| TYR 583 | 13.57 | 10.00 |
| TYR 594 | 10.60 | 10.00 |
| TYR 653 | 9.87 | 10.00 |
| TYR 701 | 10.00 | 10.00 |
| TYR 750 | 10.24 | 10.00 |
| N+ | 17.37 | 8.00 |
| LYS 13 | 10.15 | 10.50 |
| LYS 20 | 10.22 | 10.50 |
| LYS 21 | 9.87 | 10.50 |
| LYS 27 | 10.36 | 10.50 |
| LYS 43 | 10.43 | 10.50 |
| LYS 52 | 10.08 | 10.50 |
| LYS 53 | 10.08 | 10.50 |
| LYS 66 | 10.01 | 10.50 |
| LYS 70 | 9.94 | 10.50 |
| LYS 73 | 10.06 | 10.50 |
| LYS 74 | 10.50 | 10.50 |
| LYS 84 | 9.60 | 10.50 |
| LYS 99 | 10.50 | 10.50 |
| LYS 118 | 11.22 | 10.50 |
| LYS 124 | 9.94 | 10.50 |
| LYS 174 | 10.43 | 10.50 |
| LYS 192 | 10.36 | 10.50 |
| LYS 199 | 8.13 | 10.50 |
| LYS 201 | 9.94 | 10.50 |
| LYS 220 | 10.29 | 10.50 |
| LYS 221 | 10.22 | 10.50 |
| LYS 225 | 10.50 | 10.50 |
| LYS 240 | 10.01 | 10.50 |
| LYS 253 | 12.95 | 10.50 |
| LYS 287 | 14.68 | 10.50 |
| LYS 289 | 11.48 | 10.50 |
| LYS 317 | 10.23 | 10.50 |
| LYS 324 | 10.08 | 10.50 |
| LYS 360 | 11.55 | 10.50 |
| LYS 371 | 9.51 | 10.50 |
| LYS 375 | 10.50 | 10.50 |
| LYS 429 | 10.50 | 10.50 |
| LYS 443 | 10.22 | 10.50 |
| LYS 462 | 10.50 | 10.50 |
| LYS 466 | 10.22 | 10.50 |
| LYS 468 | 10.29 | 10.50 |
| LYS 477 | 10.50 | 10.50 |
| LYS 487 | 10.24 | 10.50 |
| LYS 507 | 11.91 | 10.50 |
| LYS 526 | 10.22 | 10.50 |
| LYS 531 | 10.15 | 10.50 |
| LYS 535 | 10.36 | 10.50 |
| LYS 557 | 10.01 | 10.50 |
| LYS 565 | 10.50 | 10.50 |
| LYS 570 | 10.36 | 10.50 |
| LYS 592 | 10.50 | 10.50 |
| LYS 602 | 10.43 | 10.50 |
| LYS 632 | 10.36 | 10.50 |
| LYS 638 | 10.15 | 10.50 |
| LYS 726 | 9.87 | 10.50 |
| ARG 17 | 15.49 | 12.50 |
| ARG 32 | 12.15 | 12.50 |
| ARG 58 | 11.45 | 12.50 |
| ARG 67 | 11.73 | 12.50 |
| ARG 78 | 11.94 | 12.50 |
| ARG 97 | 12.43 | 12.50 |
| ARG 101 | 12.08 | 12.50 |
| ARG 119 | 17.00 | 12.50 |
| ARG 169 | 12.15 | 12.50 |
| ARG 188 | 11.94 | 12.50 |
| ARG 193 | 13.69 | 12.50 |
| ARG 196 | 12.29 | 12.50 |
| ARG 222 | 14.49 | 12.50 |
| ARG 234 | 14.17 | 12.50 |
| ARG 243 | 12.50 | 12.50 |
| ARG 247 | 12.01 | 12.50 |
| ARG 255 | 9.85 | 12.50 |
| ARG 265 | 12.01 | 12.50 |
| ARG 266 | 10.80 | 12.50 |
| ARG 307 | 12.15 | 12.50 |
| ARG 310 | 12.22 | 12.50 |
| ARG 335 | 8.74 | 12.50 |
| ARG 346 | 11.16 | 12.50 |
| ARG 359 | 9.85 | 12.50 |
| ARG 364 | 11.90 | 12.50 |
| ARG 379 | 12.08 | 12.50 |
| ARG 380 | 11.96 | 12.50 |
| ARG 381 | 12.15 | 12.50 |
| ARG 394 | 12.50 | 12.50 |
| ARG 406 | 12.39 | 12.50 |
| ARG 425 | 11.45 | 12.50 |
| ARG 440 | 12.50 | 12.50 |
| ARG 460 | 11.45 | 12.50 |
| ARG 476 | 12.22 | 12.50 |
| ARG 482 | 11.15 | 12.50 |
| ARG 484 | 12.22 | 12.50 |
| ARG 501 | 12.22 | 12.50 |
| ARG 503 | 13.21 | 12.50 |
| ARG 518 | 11.94 | 12.50 |
| ARG 585 | 11.66 | 12.50 |
| ARG 606 | 12.29 | 12.50 |
| ARG 612 | 12.50 | 12.50 |
| ARG 613 | 12.50 | 12.50 |
| ARG 625 | 12.29 | 12.50 |
| ARG 641 | 12.15 | 12.50 |
| ARG 685 | 12.50 | 12.50 |
| ARG 713 | 12.50 | 12.50 |
| ARG 743 | 12.50 | 12.50 |
| ARG 746 | 11.94 | 12.50 |
| ARG 751 | 12.50 | 12.50 |
| ARG 756 | 12.01 | 12.50 |

TABLE 7

Candidate amino acids for modification in B103-type polymerases

| Amino Acid Residue | Substituted Amino Acid | Amino Acid Residue | Substituted Amino Acid |
|---|---|---|---|
| H58 | R | E290 | A |
| H73 | R | E293 | A |
| H74 | R | E311 | A |
| H103 | R | E319 | A |
| H146 | R | E322 | A |
| H153 | R | E331 | A |
| H336 | R | E335 | A |
| H370 | R | E338 | A |
| H458 | R | E343 | A |
| H482 | R | E352 | A |
| E11 | A | | |
| E28 | A | E359 | A |
| E43 | A | E371 | A |
| E50 | A | E405 | A |
| E72 | A | E416 | A |
| E81 | A | E417 | A |
| E148 | A | E463 | A |
| E154 | A | E466 | A |
| E158 | A | E483 | A |
| E159 | A | E505 | A |
| E161 | A | E512 | A |
| E168 | A | E517 | A |
| E216 | A | C7 | S |
| E236 | A | C19 | S |
| E238 | A | C103 | S |
| E241 | A | C445 | S |
| E273 | A | C452 | S |
| E276 | A | C513 | S |
| E288 | A | C527 | S |

What is claimed:

1. A method of identifying a base at a position in a target nucleic acid, comprising:

a) incorporating a nucleotide at a terminus of an extension primer that is hybridized to the target nucleic acid, wherein a reaction mixture for incorporating the nucleotide includes:

a variant of a polymerase enzyme that has a reduced buffering capacity within a defined pH range relative to a corresponding unsubstituted polymerase;

at least one nucleotide, wherein a terminal phosphate of the at least one nucleotide includes a thiophosphate moiety;

a phosphatase enzyme selected for hydrolyzing a thio-pyrophosphate formed in the incorporation step, wherein the at least one nucleotide is resistant to hydrolysis by the phosphatase enzyme; and a chelation moiety configured to sequester by-products of the enzymatic hydrolysis of the thio-pyrophosphate; and b) identifying the nucleotide that is incorporated at the terminus of the extension primer by detecting a hydrogen ion produced by incorporating the nucleotide.

2. The method of claim 1, wherein the phosphatase enzyme is a pyrophosphatase enzyme, and wherein the at least one nucleotide is resistant to hydrolysis by the pyrophosphatase enzyme.

3. The method of claim 1, wherein the at least one nucleotide comprises a deoxyribonucleotide-5'-γ[gamma]-thio-triphosphate.

4. The method of claim 1, wherein the specific rate of incorporation of the nucleotide with the thiophosphate moiety is at least 95% of the specific rate of incorporation of the analogous nucleotide without the thiophosphate moiety.

5. The method of claim 1, wherein the incorporating the nucleotide is conducted in a reaction chamber that is operatively coupled to at least one ion sensor that detects hydrogen ions.

6. The method of claim 5, wherein the at least one ion sensor comprises an ISFET.

7. The method of claim 1, wherein the incorporating the nucleotide is conducted on an array of reaction chambers, wherein individual reaction chambers in the array are operatively coupled to at least one ion sensor that detects hydrogen ions.

8. The method of claim 7, wherein individual reaction chambers in the array are operatively coupled to at least one ISFET.

9. The method of claim 8, wherein the array of ISFET sensors is at least $10^7$ ISFET sensors.

10. The method of claim 1, wherein the defined pH range is about pH 5.5 to about pH 9.5.

11. The method of claim 1, wherein the defined pH range is about pH 7 to about pH 9.

12. The method of claim 1, wherein the polymerase enzyme variant is a variant of a Bst polymerase.

13. The method of claim 12, wherein the variant comprises an amino acid sequence at least 80% identical to SEQ ID NO: 22.

14. The method of claim 12, wherein the variant is SEQ ID NO: 23.

15. The method of claim 12, wherein the variant is SEQ ID NO: 24.

16. The method of claim 1, wherein the polymerase enzyme variant is a variant of a *Thermococcus* sp. 9° N-7 DNA polymerase.

17. The method of claim 1, wherein the polymerase enzyme variant is a variant of a KOD polymerase.

18. The method of claim 1, wherein the polymerase enzyme variant is a variant of a B103 polymerase.

19. The method of claim 1, wherein the phosphatase enzyme is an alkaline phosphatase enzyme.

* * * * *